US009918751B2

United States Patent
Jackson

(10) Patent No.: US 9,918,751 B2
(45) Date of Patent: *Mar. 20, 2018

(54) TOOL SYSTEM FOR DYNAMIC SPINAL IMPLANTS

(71) Applicant: Roger P. Jackson, Prairie Village, KS (US)

(72) Inventor: Roger P. Jackson, Prairie Village, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/901,672

(22) Filed: May 24, 2013

(65) Prior Publication Data

US 2013/0304130 A1 Nov. 14, 2013

Related U.S. Application Data

(63) Continuation of application No. 13/373,735, filed on Nov. 28, 2011, which is a continuation-in-part of (Continued)

(51) Int. Cl.
*A61B 17/70* (2006.01)
*A61B 90/00* (2016.01)

(52) U.S. Cl.
CPC ........ *A61B 17/7082* (2013.01); *A61B 17/702* (2013.01); *A61B 17/7008* (2013.01); (Continued)

(58) Field of Classification Search
CPC ............ A61B 17/7074; A61B 17/7076; A61B 17/7077; A61B 17/7079; A61B 17/708; (Continued)

(56) References Cited

U.S. PATENT DOCUMENTS

| 854,956 A | 5/1907 | Martin |
| 1,472,464 A | 10/1923 | Ellison |

(Continued)

FOREIGN PATENT DOCUMENTS

| AU | 2012203959 | 8/2012 |
| CA | 2577436 | 6/2006 |

(Continued)

OTHER PUBLICATIONS

Brochure of Tyco/Healthcare/Surgical Dynamics on Spiral Radius 90D, Publication Date: Sep. 2001, pp. 1-8.

(Continued)

*Primary Examiner* — Lynnsy Summitt
(74) *Attorney, Agent, or Firm* — Polsinelli PC

(57) ABSTRACT

A tool set for implanting bone screws in a human spine, followed by the implantation of a longitudinal connecting member into the bone screws includes a pair of independently mountable and manipulatable elongate guide tools that form a unitary tool guide when desired. Each guide tool includes attachment structure for independent operable connection of the guide tool to an arm of the bone screw. The bone screw/guide tool attachment includes an undercut and/or recess so as to resist separation of the guide tool member from an attached bone screw. Further tools include a removable stabilizer, a cooperating bone screw driver with an attached stabilizer, a closure starter/reduction tool, a closure driver and a counter torque tool.

7 Claims, 14 Drawing Sheets

Related U.S. Application Data application No. 11/999,689, filed on Dec. 6, 2007, now Pat. No. 8,066,739, which is a continuation-in-part of application No. 11/328,481, filed on Jan. 9, 2006, now Pat. No. 7,862,587, which is a continuation-in-part of application No. 11/272,508, filed on Nov. 10, 2005, which is a continuation-in-part of application No. 10/996,289, filed on Nov. 23, 2004, now Pat. No. 8,152,810, and a continuation-in-part of application No. 10/789,149, filed on Feb. 27, 2004, now Pat. No. 7,160,300.

(60) Provisional application No. 60/873,819, filed on Dec. 8, 2006, provisional application No. 60/736,112, filed on Nov. 10, 2005, provisional application No. 60/722,300, filed on Sep. 30, 2005, provisional application No. 60/728,912, filed on Oct. 21, 2005, provisional application No. 60/725,445, filed on Oct. 11, 2005, provisional application No. 60/630,536, filed on Nov. 23, 2004.

(52) U.S. Cl.
CPC ...... *A61B 17/7032* (2013.01); *A61B 17/7085* (2013.01); *A61B 17/7091* (2013.01); *A61B 17/701* (2013.01); *A61B 17/7037* (2013.01); *A61B 2090/037* (2016.02)

(58) Field of Classification Search
CPC ............ A61B 17/7082; A61B 17/7083; A61B 17/7085; A61B 17/7086; A61B 17/7088; A61B 17/7089; A61B 17/7091
USPC ........................................ 606/279, 86 A, 104
See application file for complete search history.

(56) References Cited

U.S. PATENT DOCUMENTS

| | | |
|---|---|---|
| 2,243,717 A | 5/1941 | Moreira |
| 2,346,346 A | 4/1944 | Anderson |
| 2,362,999 A | 11/1944 | Elmer |
| 2,524,095 A | 10/1950 | Williams |
| 2,531,892 A | 11/1950 | Reese |
| 2,532,972 A | 12/1950 | Vertin |
| 2,579,438 A | 12/1951 | Longfellow |
| 2,669,896 A | 2/1954 | Clough |
| 2,813,450 A | 11/1957 | Dzus |
| 3,013,244 A | 12/1961 | Rudy |
| 3,236,275 A | 2/1966 | Smith |
| 3,604,487 A | 9/1971 | Gilbert |
| 3,640,416 A | 2/1972 | Temple |
| 3,997,138 A | 12/1976 | Crock et al. |
| 4,033,139 A | 7/1977 | Frederick |
| 4,041,939 A | 8/1977 | Hall |
| 4,190,091 A | 2/1980 | Colognori |
| 4,269,178 A | 5/1981 | Keene |
| 4,347,845 A | 9/1982 | Mayfield |
| 4,373,754 A | 2/1983 | Bollfrass et al. |
| 4,409,968 A | 10/1983 | Drummond |
| 4,448,191 A | 5/1984 | Rodnyansky et al. |
| 4,484,570 A | 11/1984 | Sutter et al. |
| 4,600,224 A | 7/1986 | Blose |
| 4,653,486 A | 3/1987 | Coker |
| 4,703,954 A | 11/1987 | Ortloff et al. |
| 4,707,001 A | 11/1987 | Johnson |
| 4,743,260 A | 5/1988 | Burton |
| 4,748,260 A | 5/1988 | Marlett |
| 4,759,672 A | 7/1988 | Nilsen et al. |
| 4,790,297 A | 12/1988 | Luque |
| 4,836,196 A | 6/1989 | Park et al. |
| 4,838,264 A | 6/1989 | Bremer et al. |
| 4,877,020 A | 10/1989 | Vich |
| 4,887,596 A | 12/1989 | Sherman |
| 4,946,458 A | 8/1990 | Harms et al. |
| 4,950,269 A | 8/1990 | Gaines, Jr. |
| 4,961,740 A | 10/1990 | Ray et al. |
| 5,005,562 A | 4/1991 | Cotrel |
| 5,015,247 A | 5/1991 | Michelson |
| 5,019,080 A | 5/1991 | Hemer |
| 5,020,519 A | 6/1991 | Hayes et al. |
| 5,022,791 A | 6/1991 | Isler |
| 5,034,011 A | 7/1991 | Howland |
| 5,067,955 A | 11/1991 | Cotrel |
| 5,084,048 A | 1/1992 | Jacob et al. |
| 5,092,635 A | 3/1992 | DeLange et al. |
| 5,092,866 A | 3/1992 | Breard et al. |
| 5,102,412 A | 4/1992 | Rogozinski |
| 5,129,388 A | 7/1992 | Vignaud et al. |
| 5,147,363 A | 7/1992 | Harle |
| 5,154,719 A | 10/1992 | Cotrel |
| 5,176,483 A | 1/1993 | Baumann et al. |
| 5,176,678 A | 1/1993 | Tsou |
| 5,176,680 A | 1/1993 | Vignaud et al. |
| 5,180,393 A | 1/1993 | Commarmond |
| 5,207,678 A | 5/1993 | Harms et al. |
| 5,217,497 A | 6/1993 | Mehdian |
| 5,257,993 A | 11/1993 | Asher et al. |
| 5,261,907 A | 11/1993 | Vignaud et al. |
| 5,261,912 A | 11/1993 | Frigg |
| 5,275,601 A | 1/1994 | Gogolewski et al. |
| 5,282,862 A | 2/1994 | Barker et al. |
| 5,282,863 A | 2/1994 | Burton |
| D346,217 S | 4/1994 | Sparker et al. |
| 5,306,275 A | 4/1994 | Bryan |
| 5,312,404 A | 5/1994 | Asher et al. |
| 5,321,901 A | 6/1994 | Kelly |
| 5,330,472 A | 7/1994 | Metz-Stavenhagen |
| 5,334,203 A | 8/1994 | Wagner |
| 5,346,493 A | 9/1994 | Stahurski et al. |
| 5,354,292 A | 10/1994 | Braeuer et al. |
| 5,358,289 A | 10/1994 | Banker et al. |
| 5,360,431 A | 11/1994 | Puno et al. |
| 5,375,823 A | 12/1994 | Navas |
| 5,385,583 A | 1/1995 | Cotrel |
| 5,395,371 A | 3/1995 | Miller et al. |
| 5,409,489 A | 4/1995 | Sioufi |
| 5,415,661 A | 5/1995 | Holmes |
| 5,423,816 A | 6/1995 | Lin |
| 5,427,418 A | 6/1995 | Watts |
| 5,429,639 A | 7/1995 | Judet |
| 5,443,467 A | 8/1995 | Biedermann et al. |
| 5,466,237 A | 11/1995 | Byrd, III et al. |
| 5,468,241 A | 11/1995 | Metz-Stavenhagen et al. |
| 5,474,555 A | 12/1995 | Puno et al. |
| 5,476,462 A | 12/1995 | Allard et al. |
| 5,476,464 A | 12/1995 | Metz-Stavenhagen et al. |
| 5,480,401 A | 1/1996 | Navas |
| 5,484,437 A | 1/1996 | Michelson |
| 5,484,440 A | 1/1996 | Allard |
| 5,487,742 A | 1/1996 | Cotrel |
| 5,489,307 A | 2/1996 | Kuslich et al. |
| 5,490,750 A | 2/1996 | Gundy |
| 5,496,321 A | 3/1996 | Puno et al. |
| 5,499,892 A | 3/1996 | Reed |
| 5,505,731 A | 4/1996 | Tornier |
| 5,507,745 A | 4/1996 | Logroscino et al. |
| 5,534,001 A | 7/1996 | Schlapfer et al. |
| 5,540,688 A | 7/1996 | Navas |
| 5,545,165 A | 8/1996 | Biedermann et al. |
| 5,549,607 A | 8/1996 | Olson et al. |
| 5,554,157 A | 9/1996 | Errico et al. |
| 5,562,660 A | 10/1996 | Grob |
| 5,562,663 A | 10/1996 | Wisnewski et al. |
| 5,569,247 A | 10/1996 | Morrison |
| 5,569,251 A | 10/1996 | Baker et al. |
| 5,584,834 A | 12/1996 | Errico et al. |
| 5,586,984 A | 12/1996 | Errico et al. |
| 5,591,166 A | 1/1997 | Bernhardt et al. |
| 5,601,553 A | 2/1997 | Trebing et al. |
| 5,607,304 A | 3/1997 | Bailey et al. |
| 5,607,425 A | 3/1997 | Rogozinski |
| 5,607,426 A | 3/1997 | Ralph et al. |

(56) References Cited

U.S. PATENT DOCUMENTS

| | | |
|---|---|---|
| 5,607,428 A | 3/1997 | Lin |
| 5,611,800 A | 3/1997 | Davis et al. |
| 5,628,740 A | 5/1997 | Mullane |
| 5,630,817 A | 5/1997 | Rokegem |
| 5,641,256 A | 6/1997 | Gundy |
| 5,643,260 A | 7/1997 | Doherty |
| 5,643,261 A | 7/1997 | Schafer et al. |
| 5,647,873 A | 7/1997 | Errico et al. |
| 5,662,652 A | 9/1997 | Schafer et al. |
| 5,662,653 A | 9/1997 | Songer et al. |
| 5,669,909 A | 9/1997 | Zdeblick et al. |
| 5,669,911 A | 9/1997 | Errico et al. |
| 5,672,175 A | 9/1997 | Martin |
| 5,672,176 A | 9/1997 | Biedermann et al. |
| 5,676,703 A | 10/1997 | Gelbard |
| 5,681,319 A | 10/1997 | Biedermann et al. |
| 5,683,390 A | 11/1997 | Metz-Stavenhagen et al. |
| 5,683,391 A | 11/1997 | Boyd |
| 5,683,392 A | 11/1997 | Richelsoph |
| 5,690,630 A | 11/1997 | Errico et al. |
| 5,697,929 A | 12/1997 | Mellinger |
| 5,711,709 A | 1/1998 | McCoy |
| 5,713,898 A | 2/1998 | Stucker et al. |
| 5,716,356 A | 2/1998 | Biedermann et al. |
| 5,720,751 A | 2/1998 | Jackson |
| 5,723,013 A | 3/1998 | Jeanson et al. |
| 5,725,527 A | 3/1998 | Biedermann et al. |
| 5,725,528 A | 3/1998 | Errico et al. |
| 5,728,098 A | 3/1998 | Sherman et al. |
| 5,733,286 A | 3/1998 | Errico et al. |
| 5,738,685 A | 4/1998 | Halm et al. |
| 5,741,254 A | 4/1998 | Henry et al. |
| 5,752,957 A | 5/1998 | Ralph et al. |
| 5,782,830 A | 7/1998 | Farris |
| 5,782,833 A | 7/1998 | Haider |
| 5,792,044 A | 8/1998 | Foley et al. |
| 5,797,911 A | 8/1998 | Sherman et al. |
| 5,800,435 A | 9/1998 | Errico et al. |
| 5,800,547 A | 9/1998 | Schafer et al. |
| 5,810,816 A | 9/1998 | Roussouly et al. |
| 5,817,094 A | 10/1998 | Errico et al. |
| 5,855,151 A | 1/1999 | Habermehl |
| 5,863,293 A | 1/1999 | Richelsoph |
| 5,865,487 A | 2/1999 | Gore et al. |
| 5,873,878 A | 2/1999 | Harms et al. |
| 5,876,402 A | 3/1999 | Errico et al. |
| 5,879,350 A | 3/1999 | Sherman et al. |
| 5,879,351 A | 3/1999 | Viart |
| 5,882,350 A | 3/1999 | Ralph et al. |
| 5,885,286 A | 3/1999 | Sherman et al. |
| 5,891,145 A | 4/1999 | Morrison et al. |
| 5,902,231 A | 5/1999 | Foley et al. |
| RE36,221 E | 6/1999 | Breard et al. |
| 5,910,141 A | 6/1999 | Morrison et al. |
| 5,938,663 A | 8/1999 | Petreto |
| 5,944,465 A | 8/1999 | Janitzki |
| 5,951,553 A | 9/1999 | Betz |
| 5,954,725 A | 9/1999 | Sherman et al. |
| 5,961,517 A | 10/1999 | Biedermann et al. |
| 5,964,760 A | 10/1999 | Richelsoph |
| 6,001,098 A | 12/1999 | Metz-Stavenhagen et al. |
| 6,004,349 A | 12/1999 | Jackson |
| 6,010,503 A | 1/2000 | Richelsoph et al. |
| 6,019,759 A | 2/2000 | Rogozinski |
| 6,022,350 A | 2/2000 | Ganem |
| 6,053,917 A | 4/2000 | Sherman et al. |
| 6,059,786 A | 5/2000 | Jackson |
| 6,063,088 A | 5/2000 | Winslow |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,102,912 A | 8/2000 | Cazin et al. |
| 6,102,913 A | 8/2000 | Jackson |
| 6,110,172 A | 8/2000 | Jackson |
| 6,113,601 A | 9/2000 | Tatar |
| 6,117,137 A | 9/2000 | Halm et al. |
| 6,132,431 A | 10/2000 | Nilsson et al. |
| 6,132,432 A | 10/2000 | Richelsoph |
| 6,132,434 A | 10/2000 | Sherman et al. |
| 6,136,002 A | 10/2000 | Shih et al. |
| 6,139,549 A | 10/2000 | Keller |
| 6,143,032 A | 11/2000 | Schafer et al. |
| 6,146,383 A | 11/2000 | Studer et al. |
| 6,183,472 B1 | 2/2001 | Lutz |
| 6,186,718 B1 | 2/2001 | Fogard |
| 6,187,005 B1 | 2/2001 | Brace et al. |
| 6,189,422 B1 | 2/2001 | Stihl |
| 6,193,720 B1 | 2/2001 | Yuan et al. |
| 6,214,012 B1 | 4/2001 | Karpman et al. |
| RE37,161 E | 5/2001 | Michelson et al. |
| 6,224,596 B1 | 5/2001 | Jackson |
| 6,224,598 B1 | 5/2001 | Jackson |
| 6,235,028 B1 | 5/2001 | Brumfield et al. |
| 6,235,034 B1 | 5/2001 | Bray |
| 6,241,730 B1 | 6/2001 | Alby |
| 6,248,105 B1 | 6/2001 | Schlapfer et al. |
| 6,248,107 B1 | 6/2001 | Foley et al. |
| 6,251,112 B1 | 6/2001 | Jackson |
| 6,254,146 B1 | 7/2001 | Church |
| 6,254,602 B1 | 7/2001 | Justis |
| 6,267,764 B1 | 7/2001 | Elberg |
| 6,267,765 B1 | 7/2001 | Taylor et al. |
| 6,273,888 B1 | 8/2001 | Justis |
| 6,277,122 B1 | 8/2001 | McGahan et al. |
| 6,280,442 B1 | 8/2001 | Barker et al. |
| 6,280,445 B1 | 8/2001 | Morrison et al. |
| 6,287,308 B1 | 9/2001 | Betz et al. |
| 6,287,311 B1 | 9/2001 | Sherman et al. |
| 6,290,700 B1 | 9/2001 | Schmotzer |
| 6,296,642 B1 | 10/2001 | Morrison et al. |
| 6,296,643 B1 | 10/2001 | Hopf et al. |
| 6,299,613 B1 | 10/2001 | Ogilvie et al. |
| 6,299,616 B1 | 10/2001 | Berger |
| 6,302,888 B1 | 10/2001 | Mellinger et al. |
| 6,309,391 B1 | 10/2001 | Crandall et al. |
| 6,315,564 B1 | 11/2001 | Levisman |
| 6,315,779 B1 | 11/2001 | Morrison et al. |
| 6,331,179 B1 | 12/2001 | Freid et al. |
| 6,355,040 B1 | 3/2002 | Richelsoph et al. |
| RE37,665 E | 4/2002 | Ralph et al. |
| 6,368,321 B1 | 4/2002 | Jackson |
| 6,371,957 B1 | 4/2002 | Amrein et al. |
| 6,379,356 B1 | 4/2002 | Jackson |
| 6,402,752 B2 | 6/2002 | Schaffler-Wachter et al. |
| 6,402,757 B1 | 6/2002 | Moore et al. |
| 6,440,133 B1 | 8/2002 | Beale et al. |
| 6,440,137 B1 | 8/2002 | Horvath et al. |
| 6,443,956 B1 | 9/2002 | Ray |
| 6,451,021 B1 | 9/2002 | Ralph et al. |
| 6,471,703 B1 | 10/2002 | Ashman |
| 6,471,705 B1 | 10/2002 | Biedermann et al. |
| 6,478,798 B1 | 11/2002 | Howland |
| 6,478,800 B1 | 11/2002 | Fraser et al. |
| 6,478,801 B1 | 11/2002 | Ralph et al. |
| 6,485,491 B1 | 11/2002 | Farris et al. |
| 6,485,492 B1 | 11/2002 | Halm et al. |
| 6,485,494 B1 | 11/2002 | Haider |
| 6,488,681 B2 | 12/2002 | Martin et al. |
| 6,508,818 B2 | 1/2003 | Steiner et al. |
| 6,511,484 B2 | 1/2003 | Torode et al. |
| 6,520,962 B1 | 2/2003 | Taylor et al. |
| 6,527,804 B1 | 3/2003 | Gauchet et al. |
| 6,530,929 B1 | 3/2003 | Justis et al. |
| 6,533,786 B1 | 3/2003 | Needham et al. |
| 6,539,826 B2 | 4/2003 | Oesterle et al. |
| 6,540,749 B2 | 4/2003 | Schafer et al. |
| 6,547,790 B2 | 4/2003 | Harkey, III et al. |
| 6,551,320 B2 | 4/2003 | Liebermann |
| 6,551,323 B2 | 4/2003 | Doubler et al. |
| 6,554,831 B1 | 4/2003 | Rivard et al. |

(56) References Cited

U.S. PATENT DOCUMENTS

| | | |
|---|---|---|
| 6,554,832 B2 | 4/2003 | Shluzas |
| 6,554,834 B1 | 4/2003 | Crozet et al. |
| 6,558,387 B2 | 5/2003 | Errico et al. |
| 6,562,038 B1 | 5/2003 | Morrison |
| 6,562,040 B1 | 5/2003 | Wagner |
| 6,565,565 B1 | 5/2003 | Yuan et al. |
| 6,565,567 B1 | 5/2003 | Haider |
| 6,572,618 B1 | 6/2003 | Morrison |
| 6,582,436 B2 | 6/2003 | Schlapfer et al. |
| 6,582,466 B1 | 6/2003 | Gauchet |
| 6,585,740 B2 | 7/2003 | Schlapfer et al. |
| 6,595,992 B1 | 7/2003 | Wagner et al. |
| 6,595,993 B2 | 7/2003 | Donno et al. |
| 6,599,294 B2 | 7/2003 | Fuss et al. |
| 6,602,255 B1 | 8/2003 | Campbell et al. |
| 6,610,063 B2 | 8/2003 | Kumar et al. |
| 6,613,050 B1 | 9/2003 | Wagner et al. |
| 6,616,667 B1 | 9/2003 | Steiger et al. |
| 6,616,669 B2 | 9/2003 | Ogilvie |
| 6,623,484 B2 | 9/2003 | Betz |
| 6,623,485 B2 | 9/2003 | Doubler et al. |
| 6,626,347 B2 | 9/2003 | Ng |
| 6,626,907 B2 | 9/2003 | Campbell et al. |
| 6,626,908 B2 | 9/2003 | Cooper et al. |
| 6,635,059 B2 | 10/2003 | Randall et al. |
| 6,635,060 B2 | 10/2003 | Hanson et al. |
| 6,648,885 B1 | 11/2003 | Friesem |
| 6,648,887 B2 | 11/2003 | Ashman |
| 6,648,888 B1 * | 11/2003 | Shluzas ............ 606/86 A |
| 6,652,526 B1 | 11/2003 | Arafiles |
| 6,652,765 B1 | 11/2003 | Beaty |
| 6,656,179 B1 | 12/2003 | Schaefer et al. |
| 6,656,181 B2 | 12/2003 | Dixon et al. |
| 6,660,004 B2 | 12/2003 | Barker et al. |
| 6,660,006 B2 | 12/2003 | Markworth et al. |
| 6,663,632 B1 | 12/2003 | Frigg |
| 6,663,635 B2 | 12/2003 | Frigg et al. |
| 6,673,073 B1 | 1/2004 | Schafer |
| 6,676,661 B1 | 1/2004 | Martin Benlloch et al. |
| 6,679,833 B2 | 1/2004 | Smith et al. |
| 6,682,529 B1 | 1/2004 | Stahurski |
| 6,682,530 B2 | 1/2004 | Dixon et al. |
| 6,689,133 B2 | 2/2004 | Morrison et al. |
| 6,689,134 B2 | 2/2004 | Ralph et al. |
| 6,695,843 B2 | 2/2004 | Biedermann et al. |
| 6,695,851 B2 | 2/2004 | Zdeblick et al. |
| 6,699,248 B2 | 3/2004 | Jackson |
| 6,699,249 B2 | 3/2004 | Schlapfer et al. |
| 6,706,045 B2 | 3/2004 | Lin et al. |
| 6,712,818 B1 | 3/2004 | Michelson |
| 6,716,213 B2 | 4/2004 | Shitoto |
| 6,716,214 B1 | 4/2004 | Jackson |
| 6,716,247 B2 | 4/2004 | Michelson |
| 6,723,100 B2 | 4/2004 | Biedermann et al. |
| 6,726,687 B2 | 4/2004 | Jackson |
| 6,730,089 B2 | 5/2004 | Jackson |
| 6,730,093 B2 | 5/2004 | Saint Martin |
| 6,730,127 B2 | 5/2004 | Michelson |
| 6,733,502 B2 | 5/2004 | Altarac et al. |
| 6,736,816 B2 | 5/2004 | Ritland |
| 6,736,820 B2 | 5/2004 | Bieeermann et al. |
| 6,740,086 B2 | 5/2004 | Richelsoph |
| 6,740,089 B2 | 5/2004 | Haider |
| 6,743,231 B1 | 6/2004 | Gray et al. |
| 6,746,449 B2 | 6/2004 | Jones et al. |
| 6,746,454 B2 | 6/2004 | Winterbottom et al. |
| 6,755,829 B1 | 6/2004 | Bono et al. |
| 6,755,835 B2 | 6/2004 | Schultheiss et al. |
| 6,755,836 B1 | 6/2004 | Lewis |
| 6,761,719 B2 | 7/2004 | Justis et al. |
| 6,761,723 B2 | 7/2004 | Butterman et al. |
| 6,767,351 B2 | 7/2004 | Orbay et al. |
| 6,770,075 B2 | 8/2004 | Howland |
| 6,778,861 B1 | 8/2004 | Liebrecht et al. |
| 6,780,186 B2 | 8/2004 | Errico et al. |
| 6,783,527 B2 | 8/2004 | Drewry et al. |
| 6,790,208 B2 | 9/2004 | Oribe et al. |
| 6,790,209 B2 | 9/2004 | Beale et al. |
| 6,802,844 B2 | 10/2004 | Ferree |
| 6,827,719 B2 | 12/2004 | Ralph et al. |
| 6,830,571 B2 | 12/2004 | Lenke et al. |
| 6,835,196 B2 | 12/2004 | Biedermann et al. |
| 6,835,205 B2 | 12/2004 | Atkinson et al. |
| 6,837,889 B2 | 1/2005 | Shluzas |
| 6,840,940 B2 | 1/2005 | Ralph et al. |
| 6,843,791 B2 | 1/2005 | Serhan |
| 6,857,343 B1 | 2/2005 | Easterbrooks et al. |
| 6,858,031 B2 | 2/2005 | Morrison et al. |
| 6,869,432 B2 | 3/2005 | Schlapfer et al. |
| 6,869,433 B2 | 3/2005 | Glascott |
| 6,872,208 B1 | 3/2005 | McBride et al. |
| 6,896,676 B2 | 5/2005 | Zubok et al. |
| 6,896,677 B1 | 5/2005 | Lin |
| 6,911,030 B1 | 6/2005 | Vanacker et al. |
| 6,932,817 B2 | 8/2005 | Baynham et al. |
| 6,932,820 B2 | 8/2005 | Osman |
| 6,932,822 B2 | 8/2005 | Oribe et al. |
| 6,945,972 B2 | 9/2005 | Frigg et al. |
| 6,953,462 B2 | 10/2005 | Liebermann |
| 6,955,677 B2 | 10/2005 | Dahners |
| 6,958,065 B2 | 10/2005 | Ueyama et al. |
| 6,964,664 B2 | 11/2005 | Freid et al. |
| 6,964,665 B2 | 11/2005 | Thomas et al. |
| 6,964,667 B2 | 11/2005 | Shaolian et al. |
| 6,966,910 B2 | 11/2005 | Ritland |
| 6,974,460 B2 | 12/2005 | Carbone et al. |
| 6,979,334 B2 | 12/2005 | Dalton |
| 6,981,973 B2 | 1/2006 | McKinley |
| 6,986,771 B2 | 1/2006 | Paul et al. |
| 6,989,011 B2 | 1/2006 | Paul et al. |
| 6,991,632 B2 | 1/2006 | Ritland |
| RE39,035 E | 3/2006 | Finn et al. |
| 7,008,422 B2 | 3/2006 | Foley et al. |
| 7,008,424 B2 | 3/2006 | Teitelbaum |
| 7,011,660 B2 | 3/2006 | Sherman et al. |
| 7,018,378 B2 | 3/2006 | Biedermann et al. |
| 7,018,379 B2 | 3/2006 | Drewry et al. |
| 7,022,122 B2 | 4/2006 | Amrein et al. |
| 7,029,475 B2 | 4/2006 | Panjabi |
| RE39,089 E | 5/2006 | Ralph et al. |
| 7,044,947 B2 | 5/2006 | de la Torre et al. |
| 7,052,497 B2 | 5/2006 | Sherman et al. |
| 7,056,321 B2 | 6/2006 | Pagliuca et al. |
| 7,066,062 B2 | 6/2006 | Flesher |
| 7,066,937 B2 | 6/2006 | Shulzas |
| 7,081,116 B1 | 7/2006 | Carly |
| 7,083,621 B2 | 8/2006 | Shaolian et al. |
| 7,087,057 B2 | 8/2006 | Konieczynski et al. |
| 7,090,674 B2 | 8/2006 | Doubler et al. |
| 7,090,679 B2 | 8/2006 | Saint-Martin et al. |
| 7,090,680 B2 | 8/2006 | Bonati et al. |
| 7,094,242 B2 | 8/2006 | Ralph et al. |
| 7,118,576 B2 | 10/2006 | Gitis et al. |
| 7,121,755 B2 | 10/2006 | Schlapfer et al. |
| 7,125,410 B2 | 10/2006 | Freudiger |
| 7,125,426 B2 | 10/2006 | Moumene et al. |
| 7,128,743 B2 | 10/2006 | Metz-Stavenhagen |
| 7,137,985 B2 | 11/2006 | Jahng |
| 7,141,051 B2 | 11/2006 | Janowski et al. |
| 7,144,396 B2 | 12/2006 | Shluzas |
| 7,160,300 B2 | 1/2007 | Jackson |
| 7,163,538 B2 | 1/2007 | Altarac et al. |
| 7,163,539 B2 | 1/2007 | Abdelgany et al. |
| 7,166,108 B2 | 1/2007 | Mazda et al. |
| 7,179,261 B2 | 2/2007 | Sicvol et al. |
| 7,186,255 B2 | 3/2007 | Baynham et al. |
| 7,188,626 B2 | 3/2007 | Foley et al. |
| 7,207,991 B2 | 4/2007 | Michelson |
| 7,207,992 B2 | 4/2007 | Ritland |
| 7,211,085 B2 | 5/2007 | Michelson |
| 7,211,086 B2 | 5/2007 | Biedermann et al. |
| 7,211,087 B2 | 5/2007 | Young |
| 7,214,227 B2 | 5/2007 | Colleran et al. |
| 7,223,268 B2 | 5/2007 | Biedermann |

(56) References Cited

U.S. PATENT DOCUMENTS

| | | |
|---|---|---|
| 7,229,441 B2 | 6/2007 | Trieu et al. |
| 7,250,052 B2 | 7/2007 | Landry et al. |
| 7,264,621 B2 | 9/2007 | Coates et al. |
| 7,270,665 B2 | 9/2007 | Morrison et al. |
| 7,282,064 B2 | 10/2007 | Chin |
| 7,290,347 B2 | 11/2007 | Augostino |
| 7,291,151 B2 | 11/2007 | Alvarez |
| 7,291,153 B2 | 11/2007 | Glascott |
| 7,294,127 B2 | 11/2007 | Hawkins et al. |
| 7,294,128 B2 | 11/2007 | Alleyne et al. |
| 7,294,129 B2 | 11/2007 | Hawkins et al. |
| 7,306,603 B2 | 12/2007 | Boehm et al. |
| 7,306,604 B2 | 12/2007 | Carli |
| 7,306,606 B2 | 12/2007 | Sasing |
| 7,314,467 B2 | 1/2008 | Howland |
| 7,316,684 B1 | 1/2008 | Baccelli et al. |
| 7,322,979 B2 | 1/2008 | Crandall et al. |
| 7,329,258 B2 | 2/2008 | Studer |
| 7,335,201 B2 | 2/2008 | Doubler et al. |
| 7,335,202 B2 | 2/2008 | Matthis et al. |
| 7,338,490 B2 | 3/2008 | Ogilvie et al. |
| 7,338,491 B2 | 3/2008 | Baker et al. |
| 7,361,196 B2 | 4/2008 | Fallin et al. |
| 7,377,921 B2 | 5/2008 | Studer et al. |
| 7,377,922 B2 | 5/2008 | Barker |
| 7,377,923 B2 | 5/2008 | Purcell et al. |
| 7,445,627 B2 | 11/2008 | Hawkes et al. |
| 7,476,228 B2 | 1/2009 | Abdou |
| 7,476,238 B2 | 1/2009 | Panjabi |
| 7,479,156 B2 | 1/2009 | Lourdel et al. |
| 7,491,208 B2 | 2/2009 | Pond, Jr. et al. |
| 7,491,218 B2 | 2/2009 | Landry et al. |
| 7,491,221 B2 | 2/2009 | David |
| 7,503,918 B2 | 3/2009 | Baccelli et al. |
| 7,503,924 B2 | 3/2009 | Lee et al. |
| 7,524,323 B2 | 4/2009 | Malandain |
| 7,527,638 B2 | 5/2009 | Anderson et al. |
| 7,527,640 B2 | 5/2009 | Ziolo et al. |
| 7,530,992 B2 | 5/2009 | Biedermann et al. |
| 7,556,639 B2 | 7/2009 | Rothman et al. |
| 7,559,942 B2 | 7/2009 | Paul et al. |
| 7,559,943 B2 | 7/2009 | Mjuwid |
| 7,563,264 B2 | 7/2009 | Landry et al. |
| 7,563,274 B2 | 7/2009 | Justis et al. |
| 7,563,275 B2 | 7/2009 | Falahee et al. |
| 7,563,283 B2 | 7/2009 | Kwak |
| 7,569,061 B2 | 8/2009 | Colleran |
| 7,572,279 B2 | 8/2009 | Jackson |
| 7,572,280 B2 | 8/2009 | Dickinson et al. |
| 7,575,587 B2 | 8/2009 | Rezach et al. |
| 7,588,575 B2 | 8/2009 | Colleran et al. |
| 7,588,588 B2 | 9/2009 | Spitler et al. |
| 7,588,589 B2 | 9/2009 | Falahee |
| 7,588,593 B2 | 9/2009 | Aferzon |
| 7,591,839 B2 | 9/2009 | Biedermann et al. |
| 7,601,166 B2 | 10/2009 | Biedermann et al. |
| 7,601,171 B2 | 10/2009 | Ainsworth |
| 7,604,653 B2 | 10/2009 | Kitchen |
| 7,604,654 B2 | 10/2009 | Fallin et al. |
| 7,604,655 B2 | 10/2009 | Warnick |
| 7,604,656 B2 | 10/2009 | Shluzas |
| 7,611,518 B2 | 11/2009 | Walder et al. |
| 7,615,068 B2 | 11/2009 | Timm et al. |
| 7,618,443 B2 | 11/2009 | Abdou |
| 7,621,912 B2 | 11/2009 | Harms et al. |
| 7,621,918 B2 | 11/2009 | Jackson |
| 7,621,940 B2 | 11/2009 | Harms et al. |
| 7,621,941 B2 | 11/2009 | Schlapfer et al. |
| 7,625,393 B2 | 12/2009 | Fallin et al. |
| 7,625,394 B2 | 12/2009 | Molz, IV et al. |
| 7,632,292 B2 | 12/2009 | Sengupta et al. |
| 7,641,673 B2 | 1/2010 | LeCouedic et al. |
| 7,641,674 B2 | 1/2010 | Young |
| 7,645,294 B2 | 1/2010 | Kalfasetd |
| 7,648,522 B2 | 1/2010 | David |
| 7,651,502 B2 | 1/2010 | Jackson |
| 7,651,515 B2 | 1/2010 | Mack et al. |
| 7,655,026 B2 | 2/2010 | Justis et al. |
| 7,658,739 B2 | 2/2010 | Shluzas |
| 7,658,752 B2 | 2/2010 | Labrom et al. |
| 7,674,277 B2 | 3/2010 | Burd et al. |
| 7,678,136 B2 | 3/2010 | Doubler et al. |
| 7,678,139 B2 | 3/2010 | Garamszegi et al. |
| 7,682,375 B2 | 3/2010 | Ritland |
| 7,682,377 B2 | 3/2010 | Konieczynski et al. |
| 7,686,833 B1 | 3/2010 | Muhanna et al. |
| 7,686,834 B2 | 3/2010 | Saint Martin |
| 7,686,835 B2 | 3/2010 | Warnick |
| 7,691,129 B2 | 4/2010 | Felix |
| 7,691,131 B2 | 4/2010 | Graf |
| 7,691,132 B2 | 4/2010 | Landry et al. |
| 7,695,475 B2 | 4/2010 | Justis et al. |
| 7,695,496 B2 | 4/2010 | Labrom et al. |
| 7,695,497 B2 | 4/2010 | Cordaro et al. |
| 7,695,498 B2 | 4/2010 | Ritland |
| 7,695,514 B2 | 4/2010 | Kwak |
| 7,699,872 B2 | 4/2010 | Farris et al. |
| 7,699,875 B2 | 4/2010 | Timm |
| 7,699,876 B2 | 4/2010 | Barry et al. |
| 7,704,271 B2 | 4/2010 | Abdou |
| 7,708,763 B2 | 5/2010 | Selover et al. |
| 7,713,288 B2 | 5/2010 | Timm et al. |
| 7,717,941 B2 | 5/2010 | Petit |
| 7,717,942 B2 | 5/2010 | Schumacher |
| 7,717,943 B2 | 5/2010 | Kirschman |
| 7,722,646 B2 | 5/2010 | Ralph et al. |
| 7,722,649 B2 | 5/2010 | Biedermann et al. |
| 7,722,651 B2 | 5/2010 | Kwak et al. |
| 7,722,652 B2 | 5/2010 | Justis et al. |
| 7,722,654 B2 | 5/2010 | Taylor et al. |
| 7,727,260 B2 | 6/2010 | Albert et al. |
| 7,727,261 B2 | 6/2010 | Barker et al. |
| 7,731,736 B2 | 6/2010 | Guenther et al. |
| 7,731,749 B2 | 6/2010 | Biedermann et al. |
| 7,749,258 B2 | 7/2010 | Biedermann et al. |
| 7,758,618 B2 | 7/2010 | Walder et al. |
| 7,763,052 B2 | 7/2010 | Jahng |
| 7,763,057 B2 | 7/2010 | Abdelgany et al. |
| 7,766,915 B2 | 8/2010 | Jackson |
| 7,766,943 B1 | 8/2010 | Fallin et al. |
| 7,766,944 B2 | 8/2010 | Metz-Stavenhagen |
| 7,766,945 B2 | 8/2010 | Nilsson et al. |
| 7,766,946 B2 | 8/2010 | Bailly |
| 7,776,067 B2 | 8/2010 | Jackson |
| 7,780,706 B2 | 8/2010 | Marino et al. |
| 7,785,351 B2 | 8/2010 | Gordon et al. |
| 7,785,354 B2 | 8/2010 | Biedermann et al. |
| 7,789,900 B2 | 9/2010 | Levy et al. |
| 7,794,477 B2 | 9/2010 | Melkent et al. |
| 7,794,480 B2 | 9/2010 | Gordon et al. |
| 7,806,913 B2 | 10/2010 | Fanger et al. |
| 7,811,288 B2 | 10/2010 | Jones et al. |
| 7,811,310 B2 | 10/2010 | Baker et al. |
| 7,815,665 B2 | 10/2010 | Jahng et al. |
| 7,819,902 B2 | 10/2010 | Abdelgany et al. |
| 7,824,430 B2 | 11/2010 | Allard et al. |
| 7,833,250 B2 | 11/2010 | Jackson |
| 7,833,252 B2 | 11/2010 | Justis et al. |
| 7,846,190 B2 | 12/2010 | Ball |
| 7,850,715 B2 | 12/2010 | Banouskou et al. |
| 7,862,587 B2 * | 1/2011 | Jackson ............ 606/246 |
| 7,862,588 B2 | 1/2011 | Abdou |
| 7,896,902 B2 | 3/2011 | Jeon et al. |
| 7,901,436 B2 | 3/2011 | Baccelli |
| 7,901,437 B2 | 3/2011 | Jackson |
| 7,947,064 B2 | 5/2011 | Bergeron et al. |
| 7,951,170 B2 | 5/2011 | Jackson |
| 7,955,358 B2 | 6/2011 | Albert |
| 7,967,848 B2 | 6/2011 | Abdelgany |
| 7,985,242 B2 | 7/2011 | Forton et al. |
| 7,988,694 B2 | 8/2011 | Barrus et al. |
| 8,034,083 B2 | 10/2011 | Abdelgany et al. |
| 8,034,084 B2 | 10/2011 | Landry et al. |
| 8,055,487 B2 | 11/2011 | James |

(56) References Cited

U.S. PATENT DOCUMENTS

| | | |
|---|---|---|
| 8,062,340 B2 | 11/2011 | Berrevoets et al. |
| 8,066,739 B2 | 11/2011 | Jackson |
| 8,075,592 B2 | 12/2011 | Landry et al. |
| 8,075,599 B2 | 12/2011 | Johnson et al. |
| 8,083,776 B2 | 12/2011 | Alvarez |
| 8,100,915 B2 | 1/2012 | Jackson |
| 8,152,837 B2 | 4/2012 | Altarac et al. |
| 8,162,948 B2 | 4/2012 | Jackson |
| 8,172,876 B2 | 5/2012 | Janowski et al. |
| 8,197,517 B1 | 6/2012 | Lab et al. |
| 8,211,110 B1 | 7/2012 | Corin et al. |
| 8,226,690 B2 | 7/2012 | Altarac et al. |
| 8,262,704 B2 * | 9/2012 | Matthis et al. ............... 606/264 |
| 8,267,969 B2 | 9/2012 | Altarac et al. |
| 8,292,926 B2 | 10/2012 | Jackson |
| 8,292,934 B2 | 10/2012 | Justis et al. |
| 8,343,165 B2 | 1/2013 | Berrevoets |
| 8,377,067 B2 | 2/2013 | Jackson |
| 8,377,100 B2 | 2/2013 | Jackson |
| 8,377,101 B2 | 2/2013 | Barrus et al. |
| 8,398,683 B2 | 3/2013 | Berrevoets et al. |
| 8,409,256 B2 | 4/2013 | Arnold et al. |
| 9,050,148 B2 | 6/2015 | Jackson |
| 9,101,415 B2 | 8/2015 | Jackson |
| 9,173,682 B2 | 11/2015 | Jackson |
| 9,216,039 B2 | 12/2015 | Jackson |
| 9,265,534 B2 | 2/2016 | Jackson |
| 9,265,535 B2 | 2/2016 | Jackson |
| 9,265,536 B2 | 2/2016 | Jackson |
| 9,265,537 B2 | 2/2016 | Jackson |
| 9,271,767 B2 | 3/2016 | Jackson |
| 9,532,815 B2 | 1/2017 | Jackson |
| 2001/0001119 A1 | 5/2001 | Lombardo |
| 2001/0010000 A1 | 7/2001 | Gertzbein |
| 2001/0012937 A1 | 8/2001 | Schaffler et al. |
| 2001/0023350 A1 | 9/2001 | Choi |
| 2001/0025553 A1 | 10/2001 | Oesterle et al. |
| 2001/0027318 A1 | 10/2001 | Oribe et al. |
| 2001/0029375 A1 | 10/2001 | Betz |
| 2001/0037111 A1 | 11/2001 | Dixon et al. |
| 2001/0041894 A1 | 11/2001 | Campbell et al. |
| 2001/0047173 A1 | 11/2001 | Schlapfer et al. |
| 2001/0047174 A1 | 11/2001 | Donno et al. |
| 2001/0047175 A1 | 11/2001 | Doubler et al. |
| 2002/0004683 A1 | 1/2002 | Michelson |
| 2002/0007184 A1 | 1/2002 | Ogilvie et al. |
| 2002/0010467 A1 | 1/2002 | Cooper et al. |
| 2002/0013586 A1 | 1/2002 | Justis et al. |
| 2002/0016594 A1 | 2/2002 | Schlapfer et al. |
| 2002/0022764 A1 | 2/2002 | Smith et al. |
| 2002/0022842 A1 | 2/2002 | Horvath et al. |
| 2002/0026193 A1 | 2/2002 | Barker et al. |
| 2002/0029040 A1 | 3/2002 | Morrison et al. |
| 2002/0035360 A1 | 3/2002 | Walder et al. |
| 2002/0035365 A1 | 3/2002 | Kumar et al. |
| 2002/0035366 A1 | 3/2002 | Walder et al. |
| 2002/0035367 A1 | 3/2002 | Ritland |
| 2002/0045898 A1 | 4/2002 | Freid et al. |
| 2002/0045899 A1 | 4/2002 | Errico et al. |
| 2002/0045904 A1 | 4/2002 | Fuss et al. |
| 2002/0049446 A1 | 4/2002 | Harkey, III et al. |
| 2002/0055740 A1 | 5/2002 | Liebermann |
| 2002/0055741 A1 | 5/2002 | Schlapfer et al. |
| 2002/0058942 A1 | 5/2002 | Biedermann et al. |
| 2002/0058950 A1 | 5/2002 | Winterbottom et al. |
| 2002/0068941 A1 | 6/2002 | Hanson et al. |
| 2002/0068975 A1 | 6/2002 | Teitelbaum et al. |
| 2002/0072751 A1 | 6/2002 | Jackson |
| 2002/0077701 A1 | 6/2002 | Kuslich |
| 2002/0082602 A1 | 6/2002 | Biedermann et al. |
| 2002/0082603 A1 | 6/2002 | Dixon et al. |
| 2002/0087159 A1 | 7/2002 | Thomas et al. |
| 2002/0087161 A1 | 7/2002 | Randall et al. |
| 2002/0091386 A1 | 7/2002 | Martin et al. |
| 2002/0091390 A1 | 7/2002 | Michelson |
| 2002/0095153 A1 | 7/2002 | Jones et al. |
| 2002/0103487 A1 | 8/2002 | Errico et al. |
| 2002/0111626 A1 | 8/2002 | Ralph et al. |
| 2002/0111628 A1 | 8/2002 | Ralph et al. |
| 2002/0116001 A1 | 8/2002 | Schaefer et al. |
| 2002/0120270 A1 | 8/2002 | Trieu et al. |
| 2002/0123752 A1 | 9/2002 | Schultheiss et al. |
| 2002/0133154 A1 | 9/2002 | Saint Martin |
| 2002/0133158 A1 | 9/2002 | Saint Martin |
| 2002/0133159 A1 | 9/2002 | Jackson |
| 2002/0138076 A1 | 9/2002 | Biedermann et al. |
| 2002/0138077 A1 | 9/2002 | Ferree |
| 2002/0143330 A1 | 10/2002 | Shluzas |
| 2002/0143332 A1 | 10/2002 | Lin et al. |
| 2002/0143338 A1 | 10/2002 | Orbay et al. |
| 2002/0143341 A1 | 10/2002 | Biedermann et al. |
| 2002/0161368 A1 | 10/2002 | Foley et al. |
| 2002/0161370 A1 | 10/2002 | Frigg et al. |
| 2002/0173789 A1 | 11/2002 | Howland |
| 2002/0173791 A1 | 11/2002 | Howland |
| 2002/0193795 A1 | 12/2002 | Gertzbein et al. |
| 2002/0198526 A1 | 12/2002 | Serhan |
| 2003/0004519 A1 | 1/2003 | Torode et al. |
| 2003/0023240 A1 | 1/2003 | Amrein et al. |
| 2003/0023243 A1 | 1/2003 | Biedermann et al. |
| 2003/0026529 A1 | 2/2003 | Durkin et al. |
| 2003/0055426 A1 | 3/2003 | Carbone et al. |
| 2003/0060826 A1 | 3/2003 | Foley et al. |
| 2003/0073996 A1 | 4/2003 | Doubler et al. |
| 2003/0073998 A1 | 4/2003 | Pagliuca et al. |
| 2003/0078580 A1 | 4/2003 | Shitoto |
| 2003/0083657 A1 | 5/2003 | Drewry et al. |
| 2003/0083667 A1 | 5/2003 | Ralph et al. |
| 2003/0093077 A1 | 5/2003 | Schlapfer et al. |
| 2003/0093078 A1 | 5/2003 | Ritland |
| 2003/0100896 A1 | 5/2003 | Biedermann et al. |
| 2003/0100897 A1 | 5/2003 | Metz-Stavenhagen |
| 2003/0100904 A1 | 5/2003 | Biedermann |
| 2003/0105460 A1 | 6/2003 | Crandall et al. |
| 2003/0109880 A1 | 6/2003 | Shirado et al. |
| 2003/0114852 A1 | 6/2003 | Biedermann et al. |
| 2003/0120275 A1 | 6/2003 | Lenke et al. |
| 2003/0125741 A1 | 7/2003 | Biedermann et al. |
| 2003/0125749 A1 | 7/2003 | Yuan et al. |
| 2003/0130659 A1 | 7/2003 | Haider |
| 2003/0130661 A1 | 7/2003 | Osman |
| 2003/0135210 A1 | 7/2003 | Dixon et al. |
| 2003/0135217 A1 | 7/2003 | Butterman et al. |
| 2003/0149432 A1 | 8/2003 | Frigg et al. |
| 2003/0150897 A1 | 8/2003 | Ng |
| 2003/0153911 A1 | 8/2003 | Shluzas |
| 2003/0153912 A1 | 8/2003 | Graf |
| 2003/0153920 A1 | 8/2003 | Ralph et al. |
| 2003/0163133 A1 | 8/2003 | Altarac et al. |
| 2003/0167058 A1 | 9/2003 | Shluzas |
| 2003/0171749 A1 | 9/2003 | Le Couedic et al. |
| 2003/0176862 A1 | 9/2003 | Taylor et al. |
| 2003/0176863 A1 | 9/2003 | Ueyama et al. |
| 2003/0181913 A1 | 9/2003 | Liebermann |
| 2003/0191469 A1 | 10/2003 | Ralph et al. |
| 2003/0191470 A1 | 10/2003 | Ritland |
| 2003/0199872 A1 | 10/2003 | Markworth et al. |
| 2003/0199873 A1 | 10/2003 | Richelsoph |
| 2003/0199874 A1 | 10/2003 | Michelson |
| 2003/0208203 A1 | 11/2003 | Lim et al. |
| 2003/0208204 A1 | 11/2003 | Bailey et al. |
| 2003/0208275 A1 | 11/2003 | Michelson |
| 2003/0212398 A1 | 11/2003 | Jackson |
| 2003/0216735 A1 | 11/2003 | Altarac et al. |
| 2003/0216748 A1 | 11/2003 | Gitis et al. |
| 2003/0220642 A1 | 11/2003 | Freudiger |
| 2003/0220643 A1 | 11/2003 | Ferree |
| 2003/0225408 A1 | 12/2003 | Nichols et al. |
| 2003/0229345 A1 | 12/2003 | Stahurski |
| 2003/0229347 A1 | 12/2003 | Sherman et al. |
| 2003/0236529 A1 | 12/2003 | Shluzas |
| 2004/0002708 A1 | 1/2004 | Ritland |
| 2004/0006342 A1 | 1/2004 | Altarac et al. |
| 2004/0034351 A1 | 2/2004 | Sherman et al. |

(56) References Cited

U.S. PATENT DOCUMENTS

| | | |
|---|---|---|
| 2004/0039384 A1 | 2/2004 | Boehm, Jr. et al. |
| 2004/0039385 A1 | 2/2004 | Mazda et al. |
| 2004/0044335 A1 | 3/2004 | Kazuaki et al. |
| 2004/0049189 A1 | 3/2004 | Le Couudic et al. |
| 2004/0049190 A1 | 3/2004 | Biedermann et al. |
| 2004/0073215 A1 | 4/2004 | Carli |
| 2004/0073218 A1 | 4/2004 | Dahners |
| 2004/0078051 A1 | 4/2004 | Davison et al. |
| 2004/0078082 A1 | 4/2004 | Lange |
| 2004/0220671 A1 | 4/2004 | Ralph et al. |
| 2004/0087949 A1 | 5/2004 | Bono et al. |
| 2004/0087950 A1 | 5/2004 | Teitelbaum |
| 2004/0087952 A1 | 5/2004 | Borgstrom et al. |
| 2004/0092934 A1 | 5/2004 | Howland |
| 2004/0092938 A1 | 5/2004 | Carli |
| 2004/0097933 A1 | 5/2004 | Lourdel et al. |
| 2004/0106925 A1 | 6/2004 | Culbert |
| 2004/0111091 A1 | 6/2004 | Ogilvie et al. |
| 2004/0116929 A1 | 6/2004 | Barker et al. |
| 2004/0122442 A1 | 6/2004 | Lewis |
| 2004/0133207 A1 | 7/2004 | Abdou |
| 2004/0138662 A1 | 7/2004 | Landry et al. |
| 2004/0143265 A1* | 7/2004 | Landry ............ A61B 17/1604 606/86 A |
| 2004/0147928 A1 | 7/2004 | Landry et al. |
| 2004/0147929 A1 | 7/2004 | Biedermann et al. |
| 2004/0158245 A1 | 8/2004 | Chin |
| 2004/0158247 A1 | 8/2004 | Sitiso et al. |
| 2004/0158258 A1 | 8/2004 | Bonati et al. |
| 2004/0162560 A1 | 8/2004 | Raynor et al. |
| 2004/0167525 A1* | 8/2004 | Jackson ........................ 606/73 |
| 2004/0172022 A1* | 9/2004 | Landry et al. ................. 606/61 |
| 2004/0172025 A1 | 9/2004 | Drewry et al. |
| 2004/0172031 A1 | 9/2004 | Rubecamp et al. |
| 2004/0176766 A1 | 9/2004 | Shluzas |
| 2004/0186473 A1 | 9/2004 | Cournoyer et al. |
| 2004/0186474 A1 | 9/2004 | Matthis et al. |
| 2004/0186475 A1 | 9/2004 | Falahee |
| 2004/0186776 A1 | 9/2004 | Zubok et al. |
| 2004/0210216 A1 | 10/2004 | Farris et al. |
| 2004/0215190 A1 | 10/2004 | Nguyen et al. |
| 2004/0215191 A1 | 10/2004 | Kitchen |
| 2004/0220567 A1 | 11/2004 | Eisermann et al. |
| 2004/0225289 A1 | 11/2004 | Biedermann et al. |
| 2004/0230100 A1 | 11/2004 | Shluzas |
| 2004/0236327 A1 | 11/2004 | Paul et al. |
| 2004/0236328 A1 | 11/2004 | Paul et al. |
| 2004/0236329 A1 | 11/2004 | Panjabi |
| 2004/0236330 A1 | 11/2004 | Purcell et al. |
| 2004/0249378 A1 | 12/2004 | Saint Martin et al. |
| 2004/0249380 A1 | 12/2004 | Glascott |
| 2004/0254574 A1 | 12/2004 | Morrison et al. |
| 2004/0267260 A1 | 12/2004 | Mack et al. |
| 2004/0267264 A1 | 12/2004 | Konieczynski et al. |
| 2005/0010219 A1 | 1/2005 | Dalton |
| 2005/0015439 A1 | 1/2005 | Balaji et al. |
| 2005/0027296 A1 | 2/2005 | Thramann et al. |
| 2005/0033298 A1 | 2/2005 | Hawkes et al. |
| 2005/0033436 A1 | 2/2005 | Schlapfer et al. |
| 2005/0033439 A1 | 2/2005 | Gordon et al. |
| 2005/0038430 A1 | 2/2005 | McKinley |
| 2005/0038432 A1 | 2/2005 | Shaolian et al. |
| 2005/0038433 A1 | 2/2005 | Young |
| 2005/0049708 A1 | 3/2005 | Atkinson et al. |
| 2005/0055026 A1 | 3/2005 | Biedermann et al. |
| 2005/0065514 A1 | 3/2005 | Studer |
| 2005/0065515 A1 | 3/2005 | Jahng |
| 2005/0065516 A1 | 3/2005 | Jahng |
| 2005/0065517 A1 | 3/2005 | Chin |
| 2005/0070899 A1 | 3/2005 | Doubler et al. |
| 2005/0070901 A1 | 3/2005 | David |
| 2005/0080415 A1 | 4/2005 | Keyer et al. |
| 2005/0085812 A1 | 4/2005 | Sherman |
| 2005/0085813 A1 | 4/2005 | Spitler et al. |
| 2005/0085815 A1 | 4/2005 | Harms et al. |
| 2005/0085816 A1 | 4/2005 | Michelson |
| 2005/0096652 A1 | 5/2005 | Burton |
| 2005/0096653 A1 | 5/2005 | Doubler et al. |
| 2005/0096654 A1 | 5/2005 | Lin |
| 2005/0107788 A1 | 5/2005 | Beaurain et al. |
| 2005/0113927 A1 | 5/2005 | Malek |
| 2005/0119658 A1 | 6/2005 | Ralph et al. |
| 2005/0124991 A1 | 6/2005 | Jahng |
| 2005/0131404 A1 | 6/2005 | Mazda et al. |
| 2005/0131405 A1 | 6/2005 | Molz, IV et al. |
| 2005/0131406 A1 | 6/2005 | Reiley et al. |
| 2005/0131407 A1 | 6/2005 | Sicvol et al. |
| 2005/0131408 A1* | 6/2005 | Sicvol et al. .................. 606/61 |
| 2005/0131413 A1 | 6/2005 | O'Driscoll et al. |
| 2005/0131419 A1 | 6/2005 | McCord et al. |
| 2005/0137593 A1 | 6/2005 | Gray et al. |
| 2005/0137594 A1 | 6/2005 | Doubler et al. |
| 2005/0137597 A1 | 6/2005 | Buller et al. |
| 2005/0141986 A1 | 6/2005 | Flesher |
| 2005/0143737 A1 | 6/2005 | Pafford et al. |
| 2005/0143823 A1 | 6/2005 | Boyd et al. |
| 2005/0149020 A1 | 7/2005 | Jahng |
| 2005/0149023 A1 | 7/2005 | Ritland |
| 2005/0149036 A1* | 7/2005 | Varieur ............ A61B 17/7091 606/86 R |
| 2005/0149053 A1 | 7/2005 | Varieur |
| 2005/0154389 A1 | 7/2005 | Selover et al. |
| 2005/0154390 A1 | 7/2005 | Biedermann et al. |
| 2005/0154391 A1 | 7/2005 | Doherty et al. |
| 2005/0159750 A1 | 7/2005 | Doherty |
| 2005/0165400 A1 | 7/2005 | Fernandez |
| 2005/0171540 A1 | 8/2005 | Lim et al. |
| 2005/0171542 A1 | 8/2005 | Biedermann et al. |
| 2005/0171543 A1 | 8/2005 | Timm et al. |
| 2005/0177154 A1 | 8/2005 | Moumene et al. |
| 2005/0177157 A1 | 8/2005 | Jahng |
| 2005/0177166 A1 | 8/2005 | Timm et al. |
| 2005/0182401 A1 | 8/2005 | Timm et al. |
| 2005/0182410 A1 | 8/2005 | Jackson |
| 2005/0187548 A1 | 8/2005 | Butler et al. |
| 2005/0187555 A1 | 8/2005 | Beidermann et al. |
| 2005/0192571 A1 | 9/2005 | Abdelgany |
| 2005/0192573 A1 | 9/2005 | Abdelgany et al. |
| 2005/0192580 A1 | 9/2005 | Dalton |
| 2005/0192589 A1 | 9/2005 | Raymond |
| 2005/0203511 A1 | 9/2005 | Wilson-MacDonald et al. |
| 2005/0203513 A1 | 9/2005 | Jahng et al. |
| 2005/0203514 A1 | 9/2005 | Jahng et al. |
| 2005/0203516 A1 | 9/2005 | Biedermann et al. |
| 2005/0203517 A1 | 9/2005 | Jahng et al. |
| 2005/0203518 A1 | 9/2005 | Beidermann et al. |
| 2005/0203519 A1 | 9/2005 | David |
| 2005/0215999 A1 | 9/2005 | Birkmeyer et al. |
| 2005/0216000 A1 | 9/2005 | Colleran et al. |
| 2005/0216001 A1 | 9/2005 | David |
| 2005/0216003 A1 | 9/2005 | Beidermann et al. |
| 2005/0228326 A1 | 10/2005 | Kalfasetd |
| 2005/0228385 A1 | 10/2005 | Lee et al. |
| 2005/0228400 A1 | 10/2005 | Chao |
| 2005/0228501 A1 | 10/2005 | Miller et al. |
| 2005/0234450 A1 | 10/2005 | Barker |
| 2005/0234451 A1 | 10/2005 | Markworth |
| 2005/0234452 A1 | 10/2005 | Malandain |
| 2005/0234453 A1 | 10/2005 | Shaolian et al. |
| 2005/0234454 A1 | 10/2005 | Chin |
| 2005/0234456 A1 | 10/2005 | Malandain |
| 2005/0234459 A1 | 10/2005 | Falahee et al. |
| 2005/0240181 A1 | 10/2005 | Boomer et al. |
| 2005/0240183 A1 | 10/2005 | Vaughan |
| 2005/0245930 A1 | 11/2005 | Timm et al. |
| 2005/0251137 A1 | 11/2005 | Ball |
| 2005/0251139 A1 | 11/2005 | Roh |
| 2005/0251140 A1 | 11/2005 | Shaolian et al. |
| 2005/0251141 A1 | 11/2005 | Frigg et al. |
| 2005/0260058 A1 | 11/2005 | Casagne, III |
| 2005/0261685 A1 | 11/2005 | Fortin et al. |
| 2005/0261687 A1 | 11/2005 | Garamszegi et al. |
| 2005/0267470 A1 | 12/2005 | McBride |
| 2005/0267471 A1 | 12/2005 | Biedermann et al. |

(56) References Cited

U.S. PATENT DOCUMENTS

| | | |
|---|---|---|
| 2005/0267472 A1 | 12/2005 | Biedermann et al. |
| 2005/0267474 A1 | 12/2005 | Dalton |
| 2005/0267477 A1 | 12/2005 | Jackson |
| 2005/0273099 A1 | 12/2005 | Baccelli et al. |
| 2005/0273101 A1 | 12/2005 | Schumacher |
| 2005/0277919 A1 | 12/2005 | Slivka et al. |
| 2005/0277922 A1 | 12/2005 | Trieu et al. |
| 2005/0277923 A1 | 12/2005 | Sweeney |
| 2005/0277925 A1 | 12/2005 | Mujwid |
| 2005/0277927 A1 | 12/2005 | Guenther et al. |
| 2005/0277928 A1 | 12/2005 | Boschert |
| 2005/0277931 A1 | 12/2005 | Sweeney et al. |
| 2005/0277934 A1 | 12/2005 | Vardiman |
| 2005/0278023 A1 | 12/2005 | Zwirkowski |
| 2005/0283152 A1 | 12/2005 | Lindemann et al. |
| 2005/0283157 A1 | 12/2005 | Coates et al. |
| 2005/0283238 A1 | 12/2005 | Reiley |
| 2005/0283244 A1 | 12/2005 | Gordon et al. |
| 2005/0288669 A1 | 12/2005 | Abdou |
| 2005/0288670 A1 | 12/2005 | Panjabi et al. |
| 2005/0288671 A1 | 12/2005 | Yuan et al. |
| 2005/0288672 A1 | 12/2005 | Ferree |
| 2005/0288673 A1 | 12/2005 | Catbagan et al. |
| 2006/0004357 A1 | 1/2006 | Lee et al. |
| 2006/0004359 A1 | 1/2006 | Kramer et al. |
| 2006/0004360 A1 | 1/2006 | Kramer et al. |
| 2006/0004363 A1 | 1/2006 | Brockmeyer et al. |
| 2006/0009767 A1 | 1/2006 | Kiester |
| 2006/0009768 A1 | 1/2006 | Ritland |
| 2006/0009769 A1 | 1/2006 | Lieberman |
| 2006/0009770 A1 | 1/2006 | Speirs et al. |
| 2006/0009775 A1 | 1/2006 | Dec et al. |
| 2006/0009780 A1 | 1/2006 | Foley et al. |
| 2006/0009846 A1 | 1/2006 | Trieu et al. |
| 2006/0015099 A1 | 1/2006 | Cannon et al. |
| 2006/0015104 A1 | 1/2006 | Dalton |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0030850 A1 | 2/2006 | Keegan et al. |
| 2006/0036240 A1 | 2/2006 | Colleran et al. |
| 2006/0036242 A1 | 2/2006 | Nilsson et al. |
| 2006/0036244 A1 | 2/2006 | Spitler et al. |
| 2006/0036246 A1 | 2/2006 | Carl et al. |
| 2006/0036252 A1 | 2/2006 | Baynham et al. |
| 2006/0036254 A1 | 2/2006 | Lim |
| 2006/0036255 A1 | 2/2006 | Pond |
| 2006/0036256 A1 | 2/2006 | Carl et al. |
| 2006/0036259 A1 | 2/2006 | Carl et al. |
| 2006/0036260 A1 | 2/2006 | Runco et al. |
| 2006/0036323 A1 | 2/2006 | Carl et al. |
| 2006/0036324 A1 | 2/2006 | Sachs et al. |
| 2006/0041259 A1 | 2/2006 | Paul et al. |
| 2006/0052780 A1 | 3/2006 | Errico et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058788 A1 | 3/2006 | Hammer et al. |
| 2006/0058790 A1 | 3/2006 | Carl et al. |
| 2006/0064090 A1 | 3/2006 | Park |
| 2006/0064091 A1 | 3/2006 | Ludwig et al. |
| 2006/0064092 A1 | 3/2006 | Howland |
| 2006/0069390 A1 | 3/2006 | Frigg |
| 2006/0074419 A1 | 4/2006 | Taylor et al. |
| 2006/0079894 A1 | 4/2006 | Colleran et al. |
| 2006/0079895 A1 | 4/2006 | McLeer |
| 2006/0079896 A1 | 4/2006 | Kwak |
| 2006/0079898 A1 | 4/2006 | Ainsworth |
| 2006/0079899 A1 | 4/2006 | Ritland |
| 2006/0079909 A1* | 4/2006 | Runco ............... A61B 17/7076 606/99 |
| 2006/0084977 A1 | 4/2006 | Liebermann |
| 2006/0084980 A1 | 4/2006 | Melkent et al. |
| 2006/0084981 A1 | 4/2006 | Shluzas |
| 2006/0084982 A1 | 4/2006 | Kim |
| 2006/0084983 A1 | 4/2006 | Kim |
| 2006/0084984 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0084989 A1 | 4/2006 | Dickinson et al. |
| 2006/0084991 A1 | 4/2006 | Borgstrom |
| 2006/0084993 A1 | 4/2006 | Landry et al. |
| 2006/0084995 A1 | 4/2006 | Biedermann et al. |
| 2006/0085069 A1 | 4/2006 | Kim |
| 2006/0085070 A1 | 4/2006 | Kim |
| 2006/0089643 A1 | 4/2006 | Mujwid |
| 2006/0089644 A1 | 4/2006 | Felix |
| 2006/0089645 A1 | 4/2006 | Eckman |
| 2006/0095035 A1 | 5/2006 | Jones et al. |
| 2006/0095037 A1 | 5/2006 | Jones et al. |
| 2006/0106380 A1 | 5/2006 | Colleran et al. |
| 2006/0106381 A1 | 5/2006 | Ferree |
| 2006/0106383 A1 | 5/2006 | Biedermann et al. |
| 2006/0106394 A1 | 5/2006 | Colleran |
| 2006/0111714 A1 | 5/2006 | Foley |
| 2006/0111715 A1 | 5/2006 | Jackson |
| 2006/0116677 A1 | 6/2006 | Burd et al. |
| 2006/0122597 A1 | 6/2006 | Jojnes et al. |
| 2006/0122599 A1 | 6/2006 | Drewry |
| 2006/0129147 A1 | 6/2006 | Biedermann et al. |
| 2006/0129149 A1 | 6/2006 | Iott et al. |
| 2006/0129239 A1 | 6/2006 | Kwak |
| 2006/0142758 A1 | 6/2006 | Petit |
| 2006/0142760 A1 | 6/2006 | McDonnell |
| 2006/0142761 A1 | 6/2006 | Landry et al. |
| 2006/0149228 A1 | 7/2006 | Schlapfer |
| 2006/0149229 A1 | 7/2006 | Kwak |
| 2006/0149232 A1 | 7/2006 | Sasing |
| 2006/0149238 A1 | 7/2006 | Sherman et al. |
| 2006/0149241 A1 | 7/2006 | Richelsoph et al. |
| 2006/0149244 A1 | 7/2006 | Amrein et al. |
| 2006/0149251 A1 | 7/2006 | Ziolo et al. |
| 2006/0155277 A1 | 7/2006 | Metz-Stavenhagen |
| 2006/0155278 A1 | 7/2006 | Warnick |
| 2006/0161152 A1 | 7/2006 | Ensign et al. |
| 2006/0166535 A1 | 7/2006 | Brumfield et al. |
| 2006/0167454 A1 | 7/2006 | Ludwig et al. |
| 2006/0167455 A1 | 7/2006 | Clement et al. |
| 2006/0173454 A1* | 8/2006 | Spitler et al. .............. 606/61 |
| 2006/0173456 A1 | 8/2006 | Hawkes et al. |
| 2006/0184171 A1 | 8/2006 | Biedermann |
| 2006/0184180 A1 | 8/2006 | Augostino |
| 2006/0189983 A1 | 8/2006 | Falin |
| 2006/0189984 A1 | 8/2006 | Fallin |
| 2006/0189985 A1 | 8/2006 | Lewis |
| 2006/0195090 A1 | 8/2006 | Suddaby |
| 2006/0195093 A1 | 8/2006 | Jahng |
| 2006/0195198 A1 | 8/2006 | Schumacher |
| 2006/0200023 A1 | 9/2006 | Melkent et al. |
| 2006/0200123 A1 | 9/2006 | Mueller |
| 2006/0200130 A1 | 9/2006 | Hawkins |
| 2006/0200131 A1 | 9/2006 | Chao et al. |
| 2006/0200132 A1 | 9/2006 | Chao et al. |
| 2006/0200135 A1 | 9/2006 | Sherman et al. |
| 2006/0200138 A1 | 9/2006 | Michelson |
| 2006/0200139 A1 | 9/2006 | Michelson |
| 2006/0200149 A1 | 9/2006 | Hoy et al. |
| 2006/0210494 A1 | 9/2006 | Rabiei et al. |
| 2006/0212033 A1 | 9/2006 | Rothman |
| 2006/0212034 A1 | 9/2006 | Triplett et al. |
| 2006/0217713 A1 | 9/2006 | Serhan et al. |
| 2006/0217714 A1 | 9/2006 | Serhan et al. |
| 2006/0217715 A1 | 9/2006 | Albert et al. |
| 2006/0217716 A1 | 9/2006 | Baker et al. |
| 2006/0229608 A1 | 10/2006 | Foster |
| 2006/0229609 A1 | 10/2006 | Wang |
| 2006/0229612 A1 | 10/2006 | Rothman |
| 2006/0229613 A1 | 10/2006 | Timm |
| 2006/0229614 A1 | 10/2006 | Foley et al. |
| 2006/0229615 A1 | 10/2006 | Abdou |
| 2006/0235389 A1 | 10/2006 | Albert et al. |
| 2006/0235392 A1 | 10/2006 | Hammer et al. |
| 2006/0235393 A1 | 10/2006 | Bono et al. |

(56) References Cited

U.S. PATENT DOCUMENTS

| | | |
|---|---|---|
| 2006/0241593 A1 | 10/2006 | Sherman et al. |
| 2006/0241595 A1 | 10/2006 | Molz, IV et al. |
| 2006/0241599 A1 | 10/2006 | Konieczynski et al. |
| 2006/0241600 A1 | 10/2006 | Ensign et al. |
| 2006/0241601 A1 | 10/2006 | Trautwein et al. |
| 2006/0241769 A1 | 10/2006 | Gordon |
| 2006/0241771 A1 | 10/2006 | Gordon |
| 2006/0247624 A1 | 11/2006 | Banouskou et al. |
| 2006/0247630 A1 | 11/2006 | Iott et al. |
| 2006/0247631 A1 | 11/2006 | Ahn et al. |
| 2006/0247632 A1 | 11/2006 | Winslow |
| 2006/0247633 A1 | 11/2006 | Winslow |
| 2006/0247635 A1 | 11/2006 | Gordon |
| 2006/0247636 A1 | 11/2006 | Yuan et al. |
| 2006/0247637 A1 | 11/2006 | Colleran |
| 2006/0247658 A1* | 11/2006 | Pond, Jr. ............ A61B 17/7091 606/104 |
| 2006/0247779 A1 | 11/2006 | Gordon |
| 2006/0264933 A1 | 11/2006 | Baker et al. |
| 2006/0264934 A1 | 11/2006 | Fallin |
| 2006/0264935 A1 | 11/2006 | White |
| 2006/0264936 A1 | 11/2006 | Partin et al. |
| 2006/0264937 A1 | 11/2006 | White |
| 2006/0264940 A1 | 11/2006 | Hartmannt |
| 2006/0264942 A1 | 11/2006 | Lim et al. |
| 2006/0264962 A1 | 11/2006 | Chin et al. |
| 2006/0269940 A1 | 11/2006 | Harman |
| 2006/0276787 A1 | 12/2006 | Zubok et al. |
| 2006/0276789 A1 | 12/2006 | Jackson |
| 2006/0276791 A1 | 12/2006 | Shluzas |
| 2006/0276792 A1 | 12/2006 | Ensign et al. |
| 2006/0282074 A1 | 12/2006 | Renaud et al. |
| 2006/0282075 A1 | 12/2006 | Labrom |
| 2006/0282076 A1 | 12/2006 | Labrom |
| 2006/0282077 A1 | 12/2006 | Labrom |
| 2006/0282078 A1 | 12/2006 | Labrom |
| 2006/0282079 A1 | 12/2006 | Labrom |
| 2006/0282080 A1 | 12/2006 | Albert |
| 2006/0293657 A1 | 12/2006 | Hartmann |
| 2006/0293659 A1 | 12/2006 | Alvarez |
| 2006/0293663 A1 | 12/2006 | Walkenhorst |
| 2006/0293665 A1 | 12/2006 | Shluzas |
| 2006/0293666 A1* | 12/2006 | Matthis et al. ................. 606/61 |
| 2006/0293693 A1* | 12/2006 | Farr ................... A61B 17/7085 606/104 |
| 2007/0005062 A1 | 1/2007 | Lange |
| 2007/0005063 A1 | 1/2007 | Bruneau |
| 2007/0005137 A1 | 1/2007 | Kwak |
| 2007/0016188 A1 | 1/2007 | Boehm, Jr. et al. |
| 2007/0016190 A1 | 1/2007 | Martinez |
| 2007/0016193 A1 | 1/2007 | Ritland |
| 2007/0016194 A1 | 1/2007 | Shaolian et al. |
| 2007/0016198 A1 | 1/2007 | Boehm, Jr. et al. |
| 2007/0016199 A1 | 1/2007 | Boehm, Jr. et al. |
| 2007/0021750 A1 | 1/2007 | Shluzas et al. |
| 2007/0032123 A1 | 2/2007 | Timm et al. |
| 2007/0043355 A1 | 2/2007 | Bette et al. |
| 2007/0043356 A1 | 2/2007 | Timm |
| 2007/0043357 A1 | 2/2007 | Kirschman |
| 2007/0043358 A1 | 2/2007 | Molz, IV et al. |
| 2007/0043359 A1 | 2/2007 | Altarac et al. |
| 2007/0043364 A1 | 2/2007 | Cawley et al. |
| 2007/0049931 A1 | 3/2007 | Justis et al. |
| 2007/0049933 A1 | 3/2007 | Ahn et al. |
| 2007/0049936 A1 | 3/2007 | Colleran |
| 2007/0055235 A1 | 3/2007 | Janowski et al. |
| 2007/0055236 A1 | 3/2007 | Hudgins |
| 2007/0055238 A1 | 3/2007 | Biedermann et al. |
| 2007/0055239 A1 | 3/2007 | Sweeney et al. |
| 2007/0055240 A1 | 3/2007 | Matthis et al. |
| 2007/0055241 A1 | 3/2007 | Matthis et al. |
| 2007/0055242 A1 | 3/2007 | Bailly |
| 2007/0055244 A1 | 3/2007 | Jackson |
| 2007/0055247 A1 | 3/2007 | Jahng |
| 2007/0073289 A1 | 3/2007 | Kwak |
| 2007/0073290 A1 | 3/2007 | Boehm, Jr. |
| 2007/0073291 A1 | 3/2007 | Cordaro et al. |
| 2007/0073293 A1 | 3/2007 | Martz |
| 2007/0073294 A1 | 3/2007 | Chin et al. |
| 2007/0073405 A1 | 3/2007 | Chin et al. |
| 2007/0078460 A1 | 4/2007 | Frigg et al. |
| 2007/0078461 A1 | 4/2007 | Shluzas |
| 2007/0083199 A1 | 4/2007 | Baccelli |
| 2007/0088357 A1 | 4/2007 | Johnson et al. |
| 2007/0088359 A1 | 4/2007 | Woods et al. |
| 2007/0093813 A1 | 4/2007 | Callahan, II et al. |
| 2007/0093814 A1 | 4/2007 | Callahan, II et al. |
| 2007/0093815 A1 | 4/2007 | Callahan, II et al. |
| 2007/0093817 A1 | 4/2007 | Barrus et al. |
| 2007/0093818 A1 | 4/2007 | Biedermann et al. |
| 2007/0093819 A1 | 4/2007 | Albert |
| 2007/0093824 A1 | 4/2007 | Hestad et al. |
| 2007/0093826 A1 | 4/2007 | Hawkes et al. |
| 2007/0093827 A1 | 4/2007 | Warnick |
| 2007/0093828 A1 | 4/2007 | Abdou |
| 2007/0093831 A1 | 4/2007 | Abdelgany et al. |
| 2007/0093833 A1 | 4/2007 | Kuiper et al. |
| 2007/0100341 A1 | 5/2007 | Reglos et al. |
| 2007/0118117 A1 | 5/2007 | Altarac et al. |
| 2007/0118118 A1 | 5/2007 | Kwak et al. |
| 2007/0118119 A1 | 5/2007 | Hestad |
| 2007/0118122 A1 | 5/2007 | Butler et al. |
| 2007/0118123 A1 | 5/2007 | Strausbaugh et al. |
| 2007/0118124 A1 | 5/2007 | Biedermann et al. |
| 2007/0123720 A1 | 5/2007 | Fabrice et al. |
| 2007/0123862 A1 | 5/2007 | Warnick |
| 2007/0123864 A1 | 5/2007 | Walder et al. |
| 2007/0123865 A1 | 5/2007 | Schlapfer et al. |
| 2007/0123866 A1 | 5/2007 | Gerbec et al. |
| 2007/0123867 A1 | 5/2007 | Kirschman |
| 2007/0123870 A1 | 5/2007 | Jeon et al. |
| 2007/0123871 A1 | 5/2007 | Jahng |
| 2007/0124249 A1 | 5/2007 | Aerrabotu et al. |
| 2007/0129729 A1 | 6/2007 | Petit et al. |
| 2007/0135815 A1 | 6/2007 | Gerbec et al. |
| 2007/0156142 A1 | 7/2007 | Rezach et al. |
| 2007/0156237 A1 | 7/2007 | Kwak |
| 2007/0161986 A1 | 7/2007 | Levy |
| 2007/0161991 A1 | 7/2007 | Altarac et al. |
| 2007/0161994 A1 | 7/2007 | Lowrey et al. |
| 2007/0161995 A1 | 7/2007 | Trautwein et al. |
| 2007/0161996 A1 | 7/2007 | Biedermann et al. |
| 2007/0161997 A1 | 7/2007 | Thramann et al. |
| 2007/0161999 A1 | 7/2007 | Biedermann et al. |
| 2007/0167948 A1 | 7/2007 | Abdou |
| 2007/0167949 A1 | 7/2007 | Altarac et al. |
| 2007/0173818 A1 | 7/2007 | Hestad et al. |
| 2007/0173819 A1 | 7/2007 | Sandlin |
| 2007/0173820 A1 | 7/2007 | Trieu |
| 2007/0173822 A1 | 7/2007 | Bruneau et al. |
| 2007/0173828 A1 | 7/2007 | Firkins et al. |
| 2007/0173832 A1 | 7/2007 | Tebbe et al. |
| 2007/0191839 A1 | 8/2007 | Justis et al. |
| 2007/0191841 A1 | 8/2007 | Justis et al. |
| 2007/0191846 A1 | 8/2007 | Bruneau et al. |
| 2007/0198014 A1 | 8/2007 | Graf et al. |
| 2007/0208344 A1 | 9/2007 | Young |
| 2007/0213720 A1 | 9/2007 | Gordon et al. |
| 2007/0225707 A1 | 9/2007 | Wisnewski et al. |
| 2007/0225708 A1 | 9/2007 | Biedermann et al. |
| 2007/0225710 A1 | 9/2007 | Jahng et al. |
| 2007/0225711 A1 | 9/2007 | Ensign |
| 2007/0233064 A1 | 10/2007 | Holt |
| 2007/0233073 A1 | 10/2007 | Wisnewski et al. |
| 2007/0233075 A1 | 10/2007 | Dawson |
| 2007/0233078 A1 | 10/2007 | Justis et al. |
| 2007/0233079 A1* | 10/2007 | Fallin ................. A61B 17/7085 606/86 A |
| 2007/0233080 A1 | 10/2007 | Na et al. |
| 2007/0233085 A1 | 10/2007 | Biedermann et al. |
| 2007/0233086 A1 | 10/2007 | Harms et al. |
| 2007/0233087 A1 | 10/2007 | Schlapfer |
| 2007/0233092 A1 | 10/2007 | Falahee |
| 2007/0233094 A1 | 10/2007 | Colleran et al. |

(56) References Cited

U.S. PATENT DOCUMENTS

| | | |
|---|---|---|
| 2007/0233095 A1 | 10/2007 | Schlaepfer |
| 2007/0233155 A1 | 10/2007 | Lovell |
| 2007/0244481 A1 | 10/2007 | Timm |
| 2007/0250061 A1 | 10/2007 | Chin et al. |
| 2007/0260243 A1 | 11/2007 | Biedermann |
| 2007/0270806 A1 | 11/2007 | Foley et al. |
| 2007/0270807 A1 | 11/2007 | Armstrong et al. |
| 2007/0270810 A1 | 11/2007 | Sanders |
| 2007/0270813 A1 | 11/2007 | Garamszegi |
| 2007/0270814 A1 | 11/2007 | Lim et al. |
| 2007/0270815 A1 | 11/2007 | Johnson et al. |
| 2007/0270821 A1 | 11/2007 | Trieu et al. |
| 2007/0270830 A1 | 11/2007 | Morrison |
| 2007/0270831 A1 | 11/2007 | Dewey et al. |
| 2007/0270832 A1 | 11/2007 | Moore |
| 2007/0270835 A1 | 11/2007 | Wisnewski |
| 2007/0270837 A1 | 11/2007 | Eckhardt et al. |
| 2007/0270838 A1 | 11/2007 | Bruneau et al. |
| 2007/0270839 A1 | 11/2007 | Jeon et al. |
| 2007/0270843 A1 | 11/2007 | Matthis et al. |
| 2007/0270869 A1 | 11/2007 | Young et al. |
| 2007/0276379 A1 | 11/2007 | Miller et al. |
| 2007/0276380 A1 | 11/2007 | Jahng et al. |
| 2007/0288004 A1 | 12/2007 | Alvarez |
| 2007/0288008 A1 | 12/2007 | Park |
| 2007/0288009 A1 | 12/2007 | Logan |
| 2007/0288011 A1 | 12/2007 | Logan |
| 2007/0288012 A1 | 12/2007 | Colleran et al. |
| 2008/0009862 A1 | 1/2008 | Hoffman |
| 2008/0009864 A1 | 1/2008 | Forton et al. |
| 2008/0015578 A1 | 1/2008 | Erickson et al. |
| 2008/0015579 A1 | 1/2008 | Whipple |
| 2008/0015580 A1 | 1/2008 | Chao |
| 2008/0015584 A1 | 1/2008 | Richelsoph |
| 2008/0015586 A1 | 1/2008 | Krishna et al. |
| 2008/0021454 A1 | 1/2008 | Chao et al. |
| 2008/0021455 A1 | 1/2008 | Chao et al. |
| 2008/0021458 A1 | 1/2008 | Lim |
| 2008/0021459 A1 | 1/2008 | Lim |
| 2008/0021462 A1 | 1/2008 | Trieu |
| 2008/0021464 A1 | 1/2008 | Norin et al. |
| 2008/0021465 A1 | 1/2008 | Shadduck et al. |
| 2008/0021466 A1 | 1/2008 | Shadduck et al. |
| 2008/0021473 A1 | 1/2008 | Butler et al. |
| 2008/0027432 A1 | 1/2008 | Strauss et al. |
| 2008/0033435 A1 | 2/2008 | Studer et al. |
| 2008/0039838 A1 | 2/2008 | Landry et al. |
| 2008/0039843 A1 | 2/2008 | Abdou |
| 2008/0045951 A1 | 2/2008 | Fanger et al. |
| 2008/0045955 A1 | 2/2008 | Berrevoets et al. |
| 2008/0045957 A1 | 2/2008 | Landry et al. |
| 2008/0051780 A1 | 2/2008 | Vaidya et al. |
| 2008/0051787 A1 | 2/2008 | Remington et al. |
| 2008/0058811 A1 | 3/2008 | Alleyne et al. |
| 2008/0058812 A1 | 3/2008 | Zehnder |
| 2008/0065071 A1 | 3/2008 | Park |
| 2008/0065073 A1 | 3/2008 | Perriello et al. |
| 2008/0065075 A1 | 3/2008 | Dant |
| 2008/0065077 A1 | 3/2008 | Ferree |
| 2008/0065079 A1 | 3/2008 | Bruneau et al. |
| 2008/0071273 A1 | 3/2008 | Hawkes et al. |
| 2008/0071274 A1 | 3/2008 | Ensign |
| 2008/0071277 A1 | 3/2008 | Warnick |
| 2008/0077136 A1 | 3/2008 | Triplett et al. |
| 2008/0077138 A1 | 3/2008 | Cohen et al. |
| 2008/0077139 A1 | 3/2008 | Landry et al. |
| 2008/0077143 A1 | 3/2008 | Shluzas |
| 2008/0086131 A1 | 4/2008 | Daly et al. |
| 2008/0086132 A1 | 4/2008 | Biedermann et al. |
| 2008/0091214 A1 | 4/2008 | Richelsoph |
| 2008/0097431 A1 | 4/2008 | Vessa |
| 2008/0097434 A1 | 4/2008 | Moumene et al. |
| 2008/0097441 A1 | 4/2008 | Hayes et al. |
| 2008/0097457 A1 | 4/2008 | Warnick |
| 2008/0108992 A1 | 5/2008 | Barry et al. |
| 2008/0114403 A1 | 5/2008 | Kuester et al. |
| 2008/0119849 A1 | 5/2008 | Beardsley et al. |
| 2008/0119850 A1 | 5/2008 | Beardsley et al. |
| 2008/0119857 A1 | 5/2008 | Potash et al. |
| 2008/0119858 A1 | 5/2008 | Potash |
| 2008/0125777 A1 | 5/2008 | Veldman et al. |
| 2008/0125787 A1 | 5/2008 | Doubler et al. |
| 2008/0132952 A1 | 6/2008 | Malandain et al. |
| 2008/0132957 A1 | 6/2008 | Matthis et al. |
| 2008/0140075 A1 | 6/2008 | Ensign et al. |
| 2008/0140076 A1 | 6/2008 | Jackson |
| 2008/0140133 A1 | 6/2008 | Allard et al. |
| 2008/0147122 A1 | 6/2008 | Jackson |
| 2008/0154279 A1 | 6/2008 | Schumaker et al. |
| 2008/0154307 A1 | 6/2008 | Colleran et al. |
| 2008/0234744 A1 | 6/2008 | Zylber et al. |
| 2008/0161854 A1 | 7/2008 | Bae et al. |
| 2008/0161857 A1* | 7/2008 | Hestad et al. ............... 606/264 |
| 2008/0161859 A1 | 7/2008 | Nilsson |
| 2008/0161863 A1 | 7/2008 | Arnold et al. |
| 2008/0167687 A1 | 7/2008 | Colleran et al. |
| 2008/0172090 A1 | 7/2008 | Molz |
| 2008/0172091 A1 | 7/2008 | Anderson |
| 2008/0172096 A1 | 7/2008 | Hawkins |
| 2008/0177316 A1 | 7/2008 | Bergeronk et al. |
| 2008/0177317 A1 | 7/2008 | Jackson |
| 2008/0177319 A1 | 7/2008 | Schwab |
| 2008/0177321 A1 | 7/2008 | Drewry et al. |
| 2008/0177322 A1 | 7/2008 | Davis et al. |
| 2008/0177327 A1 | 7/2008 | Malandain et al. |
| 2008/0177332 A1 | 7/2008 | Reiley et al. |
| 2008/0183212 A1 | 7/2008 | Veldman et al. |
| 2008/0183213 A1 | 7/2008 | Veldman et al. |
| 2008/0183215 A1 | 7/2008 | Altarac et al. |
| 2008/0183216 A1 | 7/2008 | Jackson |
| 2008/0183219 A1 | 7/2008 | Jackson |
| 2008/0183223 A1 | 7/2008 | Jeon et al. |
| 2008/0195100 A1 | 8/2008 | Capote et al. |
| 2008/0195153 A1 | 8/2008 | Thompson |
| 2008/0195155 A1 | 8/2008 | Hoffman et al. |
| 2008/0195159 A1 | 8/2008 | Kloss et al. |
| 2008/0200918 A1 | 8/2008 | Spitler et al. |
| 2008/0200956 A1 | 8/2008 | Beckwith et al. |
| 2008/0215095 A1 | 9/2008 | Biedermann et al. |
| 2008/0221620 A1 | 9/2008 | Krause |
| 2008/0221692 A1 | 9/2008 | Zucherman et al. |
| 2008/0228184 A1 | 9/2008 | Hestad |
| 2008/0228227 A1 | 9/2008 | Brown et al. |
| 2008/0228228 A1* | 9/2008 | Hestad et al. ............... 606/246 |
| 2008/0228229 A1 | 9/2008 | Walder et al. |
| 2008/0234691 A1 | 9/2008 | Schwab |
| 2008/0234734 A1 | 9/2008 | Wabler et al. |
| 2008/0234736 A1 | 9/2008 | Trieu et al. |
| 2008/0234737 A1 | 9/2008 | Bosehert |
| 2008/0234738 A1 | 9/2008 | Zylber et al. |
| 2008/0234739 A1 | 9/2008 | Hudgins et al. |
| 2008/0234746 A1 | 9/2008 | Jahng et al. |
| 2008/0234756 A1 | 9/2008 | Sutcliffe et al. |
| 2008/0234759 A1 | 9/2008 | Marino |
| 2008/0243052 A1 | 10/2008 | Pond et al. |
| 2008/0243185 A1 | 10/2008 | Felix et al. |
| 2008/0243188 A1 | 10/2008 | Walder |
| 2008/0243194 A1 | 10/2008 | Lotz et al. |
| 2008/0249570 A1 | 10/2008 | Carson et al. |
| 2008/0249576 A1 | 10/2008 | Wawkes et al. |
| 2008/0255617 A1 | 10/2008 | Cho et al. |
| 2008/0262546 A1 | 10/2008 | Calvosa et al. |
| 2008/0262548 A1 | 10/2008 | Lange et al. |
| 2008/0262551 A1 | 10/2008 | Rice et al. |
| 2008/0262552 A1 | 10/2008 | Kim |
| 2008/0262554 A1 | 10/2008 | Hayes et al. |
| 2008/0262556 A1 | 10/2008 | Jacofsky et al. |
| 2008/0269742 A1 | 10/2008 | Levy et al. |
| 2008/0269804 A1 | 10/2008 | Holt |
| 2008/0269805 A1 | 10/2008 | Dekutoski et al. |
| 2008/0269809 A1 | 10/2008 | Garamszegi |
| 2008/0275456 A1 | 11/2008 | Vonwiller et al. |
| 2008/0275504 A1 | 11/2008 | Bonin et al. |
| 2008/0287994 A1 | 11/2008 | Perez-Cruet et al. |

(56) References Cited

U.S. PATENT DOCUMENTS

| | | |
|---|---|---|
| 2008/0288002 A1 | 11/2008 | Crall et al. |
| 2008/0300630 A1 | 12/2008 | Bohnema et al. |
| 2008/0300633 A1 | 12/2008 | Jackson |
| 2008/0306513 A1 | 12/2008 | Winslow et al. |
| 2008/0306525 A1 | 12/2008 | Winslow et al. |
| 2008/0306528 A1 | 12/2008 | Winslow et al. |
| 2008/0306533 A1 | 12/2008 | Winslow et al. |
| 2008/0306536 A1 | 12/2008 | Frig et al. |
| 2008/0306539 A1 | 12/2008 | Cain et al. |
| 2008/0306540 A1 | 12/2008 | Mitchell et al. |
| 2008/0306543 A1 | 12/2008 | Cain et al. |
| 2008/0306545 A1 | 12/2008 | Winslow |
| 2008/0312655 A1 | 12/2008 | Kirschman et al. |
| 2008/0312692 A1 | 12/2008 | Brennan et al. |
| 2008/0312694 A1 | 12/2008 | Peterman et al. |
| 2008/0312696 A1 | 12/2008 | Battlers et al. |
| 2008/0312701 A1 | 12/2008 | Batters et al. |
| 2008/0312703 A1 | 12/2008 | Hestad et al. |
| 2008/0312704 A1 | 12/2008 | Hestad et al. |
| 2009/0005787 A1 | 1/2009 | Crall et al. |
| 2009/0005813 A1 | 1/2009 | Crall et al. |
| 2009/0005814 A1 | 1/2009 | Miller et al. |
| 2009/0005817 A1 | 1/2009 | Friedrich et al. |
| 2009/0012567 A1 | 1/2009 | Biedermann et al. |
| 2009/0018583 A1 | 1/2009 | Song et al. |
| 2009/0018591 A1 | 1/2009 | Hawkes et al. |
| 2009/0024165 A1 | 1/2009 | Ferree |
| 2009/0024169 A1 | 1/2009 | Triplett et al. |
| 2009/0030457 A1 | 1/2009 | Janowski et al. |
| 2009/0030464 A1 | 1/2009 | Hestad et al. |
| 2009/0030465 A1 | 1/2009 | Altarac et al. |
| 2009/0036929 A1 | 2/2009 | Reglos et al. |
| 2009/0036932 A1 | 2/2009 | Rouyer et al. |
| 2009/0036934 A1 | 2/2009 | Biedermann et al. |
| 2009/0048601 A1 | 2/2009 | Forton et al. |
| 2009/0048631 A1 | 2/2009 | Bhatnagar et al. |
| 2009/0054932 A1 | 2/2009 | Butler et al. |
| 2009/0062860 A1 | 3/2009 | Fraiser et al. |
| 2009/0062865 A1 | 3/2009 | Schumacher |
| 2009/0062867 A1 | 3/2009 | Schumacher |
| 2009/0062914 A1 | 3/2009 | Marino |
| 2009/0069849 A1 | 3/2009 | Oh et al. |
| 2009/0069852 A1 | 3/2009 | Farris et al. |
| 2009/0069853 A1 | 3/2009 | Schumacher |
| 2009/0076550 A1 | 3/2009 | Bernhardt, Jr. et al. |
| 2009/0076552 A1 | 3/2009 | Tornier |
| 2009/0082809 A1 | 3/2009 | Nguyen et al. |
| 2009/0082812 A1 | 3/2009 | Lewis |
| 2009/0082815 A1 | 3/2009 | Zylber et al. |
| 2009/0082819 A1 | 3/2009 | Blain et al. |
| 2009/0088782 A1 | 4/2009 | Moumene et al. |
| 2009/0088799 A1 | 4/2009 | Yeh |
| 2009/0088803 A1 | 4/2009 | Justis et al. |
| 2009/0088807 A1 | 4/2009 | Castaneda et al. |
| 2009/0093820 A1 | 4/2009 | Trieu et al. |
| 2009/0093843 A1 | 4/2009 | Lemoine et al. |
| 2009/0093845 A1 | 4/2009 | Hestad et al. |
| 2009/0093846 A1 | 4/2009 | Hestad et al. |
| 2009/0099606 A1 | 4/2009 | Hestad et al. |
| 2009/0099607 A1 | 4/2009 | Fallin et al. |
| 2009/0099608 A1 | 4/2009 | Szczesny |
| 2009/0105760 A1 | 4/2009 | Frey |
| 2009/0105769 A1* | 4/2009 | Rock et al. .................. 606/308 |
| 2009/0105770 A1 | 4/2009 | Berrevoets et al. |
| 2009/0105771 A1 | 4/2009 | Lei et al. |
| 2009/0112265 A1 | 4/2009 | Hudgins et al. |
| 2009/0112266 A1 | 4/2009 | Weng et al. |
| 2009/0112267 A1 | 4/2009 | Atkinson et al. |
| 2009/0118767 A1 | 5/2009 | Hestad et al. |
| 2009/0118772 A1 | 5/2009 | Diederich et al. |
| 2009/0125063 A1 | 5/2009 | Panjabi |
| 2009/0131981 A1 | 5/2009 | White |
| 2009/0131983 A1 | 5/2009 | Biedermann |
| 2009/0138044 A1 | 5/2009 | Bergeron et al. |
| 2009/0138052 A1 | 5/2009 | Biedermann et al. |
| 2009/0143827 A1 | 6/2009 | Levy et al. |
| 2009/0143828 A1 | 6/2009 | Stad et al. |
| 2009/0143829 A1 | 6/2009 | Shluzas |
| 2009/0149885 A1 | 6/2009 | Durwood et al. |
| 2009/0149887 A1 | 6/2009 | Schlaepfer et al. |
| 2009/0149892 A1 | 6/2009 | Stad et al. |
| 2009/0163901 A1 | 6/2009 | Fisher et al. |
| 2009/0163953 A1 | 6/2009 | Biedermann et al. |
| 2009/0163954 A1 | 6/2009 | Kwak |
| 2009/0163955 A1 | 6/2009 | Moumene et al. |
| 2009/0163956 A1 | 6/2009 | Biedermann et al. |
| 2009/0163961 A1 | 6/2009 | Kirschman |
| 2009/0163963 A1 | 6/2009 | Berrevoets |
| 2009/0171392 A1 | 7/2009 | Garcia-Bengochea et al. |
| 2009/0171395 A1 | 7/2009 | Jeon et al. |
| 2009/0177232 A1 | 7/2009 | Kiester |
| 2009/0182380 A1 | 7/2009 | Abdelgany |
| 2009/0192548 A1 | 7/2009 | Jeon et al. |
| 2009/0192551 A1 | 7/2009 | Cianfrani et al. |
| 2009/0198280 A1 | 8/2009 | Spratt et al. |
| 2009/0198281 A1 | 8/2009 | Rice et al. |
| 2009/0198289 A1 | 8/2009 | Manderson |
| 2009/0198291 A1 | 8/2009 | Kevin et al. |
| 2009/0204155 A1 | 8/2009 | Aschmann |
| 2009/0216280 A1 | 8/2009 | Hutchinson |
| 2009/0221877 A1 | 9/2009 | Woods |
| 2009/0228045 A1 | 9/2009 | Hayes et al. |
| 2009/0240286 A1 | 9/2009 | Friedrich et al. |
| 2009/0240287 A1 | 9/2009 | Cunliffe et al. |
| 2009/0240292 A1 | 9/2009 | Butler et al. |
| 2009/0248030 A1 | 10/2009 | Butler et al. |
| 2009/0248075 A1 | 10/2009 | Ogilvie et al. |
| 2009/0248077 A1 | 10/2009 | Johns |
| 2009/0248081 A1 | 10/2009 | LeHuec et al. |
| 2009/0248083 A1 | 10/2009 | Patterson et al. |
| 2009/0248088 A1 | 10/2009 | Biedermann |
| 2009/0254123 A1 | 10/2009 | Pafford et al. |
| 2009/0254125 A1 | 10/2009 | Predick |
| 2009/0259254 A1 | 10/2009 | Pisharodi |
| 2009/0259257 A1 | 10/2009 | Prevost |
| 2009/0259258 A1 | 10/2009 | Perez-Cruet et al. |
| 2009/0264895 A1 | 10/2009 | Gasperut et al. |
| 2009/0264896 A1 | 10/2009 | Biedermann et al. |
| 2009/0264930 A1 | 10/2009 | McBride |
| 2009/0264933 A1 | 10/2009 | Carls et al. |
| 2009/0270916 A1 | 10/2009 | Ramsay et al. |
| 2009/0270917 A1 | 10/2009 | Boehm |
| 2009/0270920 A1 | 10/2009 | Douget et al. |
| 2009/0270921 A1 | 10/2009 | Krause |
| 2009/0270922 A1 | 10/2009 | Biedermann et al. |
| 2009/0275981 A1 | 11/2009 | Abdelgany et al. |
| 2009/0275983 A1 | 11/2009 | Veldman et al. |
| 2009/0275986 A1 | 11/2009 | Prevost et al. |
| 2009/0281571 A1 | 11/2009 | Weaver et al. |
| 2009/0281572 A1 | 11/2009 | White |
| 2009/0281573 A1 | 11/2009 | Biedermann et al. |
| 2009/0287250 A1 | 11/2009 | Molz, IV et al. |
| 2009/0287251 A1 | 11/2009 | Bae et al. |
| 2009/0287252 A1 | 11/2009 | Marik et al. |
| 2009/0287253 A1 | 11/2009 | Felix et al. |
| 2009/0299411 A1 | 12/2009 | Laskowitz et al. |
| 2009/0299415 A1 | 12/2009 | Pimenta |
| 2009/0306719 A1 | 12/2009 | Meyer, III et al. |
| 2009/0306720 A1 | 12/2009 | Doubler et al. |
| 2009/0312804 A1 | 12/2009 | Gamache et al. |
| 2009/0318968 A1 | 12/2009 | Duggal et al. |
| 2009/0326582 A1 | 12/2009 | Songer et al. |
| 2009/0326583 A1 | 12/2009 | Moumene et al. |
| 2009/0326586 A1 | 12/2009 | Duarte |
| 2009/0326587 A1 | 12/2009 | Matthis et al. |
| 2010/0004692 A1 | 1/2010 | Biedermann et al. |
| 2010/0004695 A1 | 1/2010 | Stad et al. |
| 2010/0010540 A1 | 1/2010 | Park |
| 2010/0010544 A1 | 1/2010 | Fallin et al. |
| 2010/0016898 A1 | 1/2010 | Shluzas |
| 2010/0023061 A1 | 1/2010 | Randol et al. |
| 2010/0030224 A1 | 2/2010 | Winslow et al. |
| 2010/0030271 A1 | 2/2010 | Winslow et al. |
| 2010/0030283 A1 | 2/2010 | King et al. |

(56) References Cited

U.S. PATENT DOCUMENTS

| | | |
|---|---|---|
| 2010/0036420 A1 | 2/2010 | Kalfas et al. |
| 2010/0036422 A1 | 2/2010 | Flynn et al. |
| 2010/0036423 A1 | 2/2010 | Hayes et al. |
| 2010/0036424 A1 | 2/2010 | Fielding et al. |
| 2010/0036425 A1 | 2/2010 | Barrus et al. |
| 2010/0036443 A1 | 2/2010 | Hutton et al. |
| 2010/0042149 A1 | 2/2010 | Chao et al. |
| 2010/0042152 A1 | 2/2010 | Semier et al. |
| 2010/0042155 A1 | 2/2010 | Biedermann et al. |
| 2010/0042156 A1 | 2/2010 | Harms et al. |
| 2010/0049254 A1 | 2/2010 | Biedermann et al. |
| 2010/0057125 A1 | 3/2010 | Viker |
| 2010/0057126 A1 | 3/2010 | Hestad |
| 2010/0063544 A1 | 3/2010 | Butler |
| 2010/0063545 A1 | 3/2010 | Richelsoph |
| 2010/0063547 A1 | 3/2010 | Morin et al. |
| 2010/0063550 A1 | 3/2010 | Felix et al. |
| 2010/0063551 A1 | 3/2010 | Richelsoph |
| 2010/0063552 A1 | 3/2010 | Chin et al. |
| 2010/0063553 A1 | 3/2010 | Warnick |
| 2010/0069919 A1 | 3/2010 | Carls et al. |
| 2010/0069963 A1 | 3/2010 | Eckman |
| 2010/0069964 A1 | 3/2010 | Lechmann |
| 2010/0069969 A1 | 3/2010 | Ampuero et al. |
| 2010/0087858 A1 | 4/2010 | Abdou |
| 2010/0087861 A1 | 4/2010 | Lechmann et al. |
| 2010/0087862 A1 | 4/2010 | Biedermann et al. |
| 2010/0087863 A1 | 4/2010 | Biedermann et al. |
| 2010/0087864 A1 | 4/2010 | Klein et al. |
| 2010/0087865 A1 | 4/2010 | Biedermann et al. |
| 2010/0088782 A1 | 4/2010 | Moumene et al. |
| 2010/0094343 A1 | 4/2010 | Pham et al. |
| 2010/0094345 A1 | 4/2010 | Saidha et al. |
| 2010/0094348 A1 | 4/2010 | Biedermann et al. |
| 2010/0094349 A1 | 4/2010 | Hammer et al. |
| 2010/0094352 A1 | 4/2010 | Iott et al. |
| 2010/0094353 A1 | 4/2010 | Shim et al. |
| 2010/0100136 A1 | 4/2010 | Won et al. |
| 2010/0100137 A1 | 4/2010 | Justis et al. |
| 2010/0106189 A1 | 4/2010 | Miller |
| 2010/0114170 A1 | 5/2010 | Barrus et al. |
| 2010/0114171 A1 | 5/2010 | Boachie-Adjei et al. |
| 2010/0114179 A1 | 5/2010 | Moore et al. |
| 2010/0114180 A1 | 5/2010 | Rock et al. |
| 2010/0114182 A1 | 5/2010 | Wilcox et al. |
| 2010/0121385 A1 | 5/2010 | Blain et al. |
| 2010/0121386 A1 | 5/2010 | Peultier et al. |
| 2010/0125302 A1 | 5/2010 | Hammill, Sr. et al. |
| 2010/0131017 A1 | 5/2010 | Farris et al. |
| 2010/0131018 A1 | 5/2010 | Konieczynski et al. |
| 2010/0137918 A1 | 6/2010 | Wilcox et al. |
| 2010/0137920 A1 | 6/2010 | Hammill, Sr. et al. |
| 2010/0145390 A1 | 6/2010 | McCarthy et al. |
| 2010/0152776 A1 | 6/2010 | Keyer et al. |
| 2010/0152785 A1 | 6/2010 | Forton et al. |
| 2010/0152787 A1 | 6/2010 | Walsh et al. |
| 2010/0152788 A1 | 6/2010 | Warnick |
| 2010/0160965 A1 | 6/2010 | Viker |
| 2010/0160974 A1 | 6/2010 | Viker |
| 2010/0160980 A1 | 6/2010 | Walsh et al. |
| 2010/0168796 A1 | 7/2010 | Eliasen et al. |
| 2010/0168800 A1 | 7/2010 | Biedermann et al. |
| 2010/0168801 A1 | 7/2010 | Biedermann et al. |
| 2010/0168803 A1 | 7/2010 | Hestad et al. |
| 2010/0174322 A1 | 7/2010 | Abdelgany et al. |
| 2010/0179602 A1 | 7/2010 | Dauster et al. |
| 2010/0179603 A1 | 7/2010 | Warnick |
| 2010/0185247 A1 | 7/2010 | Richelsoph |
| 2010/0191290 A1 | 7/2010 | Felix |
| 2010/0198269 A1 | 8/2010 | Taylor et al. |
| 2010/0198270 A1 | 8/2010 | Barker et al. |
| 2010/0198272 A1 | 8/2010 | Keyer et al. |
| 2010/0204735 A1 | 8/2010 | Gephart et al. |
| 2010/0204736 A1 | 8/2010 | Biedermann et al. |
| 2010/0222822 A1 | 9/2010 | Farris et al. |
| 2010/0222828 A1 | 9/2010 | Stad et al. |
| 2010/0228293 A1 | 9/2010 | Courtney et al. |
| 2010/0234891 A1 | 9/2010 | Freeman et al. |
| 2010/0241170 A1 | 9/2010 | Cammisa et al. |
| 2010/0249846 A1 | 9/2010 | Simonson |
| 2010/0249856 A1 | 9/2010 | Iott et al. |
| 2010/0256681 A1 | 10/2010 | Hammer et al. |
| 2010/0256682 A1 | 10/2010 | Fallin et al. |
| 2010/0262196 A1 | 10/2010 | Barrus et al. |
| 2011/0007941 A1 | 1/2011 | Chen et al. |
| 2011/0046683 A1 | 2/2011 | Biedermann et al. |
| 2011/0093015 A1 | 4/2011 | Ramsay et al. |
| 2011/0166610 A1 | 7/2011 | Altarac et al. |
| 2011/0178560 A1 | 7/2011 | Butler et al. |
| 2011/0184469 A1 | 7/2011 | Ballard et al. |
| 2011/0184471 A1 | 7/2011 | Foley et al. |
| 2011/0190822 A1 | 8/2011 | Spitler et al. |
| 2011/0202094 A1 | 8/2011 | Pereira et al. |
| 2011/0202095 A1 | 8/2011 | Semler et al. |
| 2011/0313460 A1 | 12/2011 | Mclean et al. |
| 2012/0071886 A1* | 3/2012 | Jackson ................ 606/104 |
| 2014/0222090 A1 | 8/2014 | Jackson |
| 2015/0080974 A1 | 3/2015 | Jackson |
| 2015/0142060 A1 | 5/2015 | Jackson |
| 2015/0182258 A1 | 7/2015 | Jackson |
| 2015/0265322 A1 | 9/2015 | Jackson |
| 2015/0272631 A1 | 10/2015 | Jaclson |
| 2016/0015433 A1 | 1/2016 | Jackson |
| 2016/0074077 A1 | 3/2016 | Jackson |
| 2017/0181775 A1 | 6/2017 | Jackson |

FOREIGN PATENT DOCUMENTS

| | | |
|---|---|---|
| DE | 4239716 | 8/1994 |
| DE | 4425392 | 11/1995 |
| DE | 19507141 | 9/1996 |
| DE | 19509141 | 9/1996 |
| DE | 19509331 | 9/1996 |
| DE | 29806563 | 7/1998 |
| DE | 29810798 | 12/1999 |
| DE | 19951145 | 5/2001 |
| DE | 20207850 | 10/2002 |
| DE | 10236691 | 2/2004 |
| DE | 102007055745 | 7/2008 |
| EP | 0667127 | 8/1995 |
| EP | 0669109 | 8/1995 |
| EP | 0677277 | 10/1995 |
| EP | 0885598 | 12/1998 |
| EP | 1121902 | 8/2001 |
| EP | 1190678 | 3/2002 |
| EP | 1210914 | 6/2002 |
| EP | 1570795 | 2/2005 |
| EP | 1579816 | 9/2005 |
| EP | 1634537 | 3/2006 |
| EP | 1925263 | 5/2008 |
| EP | 2082709 | 7/2009 |
| ES | 2000325358 | 3/2000 |
| FR | 2717370 | 9/1995 |
| FR | 2718946 | 10/1995 |
| FR | 2729291 | 7/1996 |
| FR | 2796545 | 1/2001 |
| FR | 2799949 | 4/2001 |
| FR | 2814936 | 4/2002 |
| FR | 2856578 | 6/2003 |
| FR | 2865373 | 1/2004 |
| FR | 2865375 | 1/2004 |
| FR | 2865377 | 1/2004 |
| FR | 2846223 | 4/2004 |
| FR | 2857850 | 4/2004 |
| FR | 2865378 | 10/2004 |
| FR | 2925288 | 6/2009 |
| GB | 1519139 | 7/1978 |
| GB | 9202745.8 | 4/1992 |
| GB | 2365345 | 2/2002 |
| GB | 2382304 | 5/2003 |
| JP | 10277070 | 10/1998 |
| SU | 313538 | 10/1971 |
| WO | 8912431 | 12/1989 |
| WO | 9116020 | 10/1991 |

(56) References Cited

FOREIGN PATENT DOCUMENTS

| | | |
|---|---|---|
| WO | WO92/03100 | 3/1992 |
| WO | 9321848 | 11/1993 |
| WO | 9410944 | 5/1994 |
| WO | WO94/10927 | 5/1994 |
| WO | WO94/26191 | 11/1994 |
| WO | 9428824 | 12/1994 |
| WO | WO 95/013755 | 5/1995 |
| WO | 9531947 | 11/1995 |
| WO | 9606576 | 3/1996 |
| WO | 9621396 | 7/1996 |
| WO | 9628105 | 9/1996 |
| WO | 9628118 | 9/1996 |
| WO | WO96/41582 | 12/1996 |
| WO | 9714368 | 4/1997 |
| WO | 9727812 | 8/1997 |
| WO | 9801091 | 1/1998 |
| WO | 9815233 | 4/1998 |
| WO | 9825534 | 6/1998 |
| WO | 9832386 | 7/1998 |
| WO | 9834554 | 8/1998 |
| WO | 9838924 | 9/1998 |
| WO | 9905980 | 2/1999 |
| WO | 9938463 | 8/1999 |
| WO | 9947083 | 9/1999 |
| WO | 2000022997 | 4/2000 |
| WO | 2000027297 | 5/2000 |
| WO | 2000065268 | 11/2000 |
| WO | 2000066045 | 11/2000 |
| WO | WO2001/010317 | 2/2001 |
| WO | 2001015612 | 3/2001 |
| WO | 2001028435 | 4/2001 |
| WO | WO2001/028436 | 4/2001 |
| WO | WO01/45576 | 6/2001 |
| WO | 2001049191 | 7/2001 |
| WO | 2001067972 | 9/2001 |
| WO | 2001067974 | 9/2001 |
| WO | 2002034150 | 5/2002 |
| WO | WO2002/054966 | 7/2002 |
| WO | WO2002/102259 | 12/2002 |
| WO | 2003007828 | 1/2003 |
| WO | WO03/026523 | 4/2003 |
| WO | 2003047442 | 6/2003 |
| WO | WO2003/068088 | 8/2003 |
| WO | 2004022108 | 3/2004 |
| WO | 2004041100 | 5/2004 |
| WO | WO2004/041100 | 5/2004 |
| WO | WO2004/075778 | 9/2004 |
| WO | WO2004/089245 | 10/2004 |
| WO | 2004098452 | 11/2004 |
| WO | WO2004/107997 | 12/2004 |
| WO | WO2005/000136 | 1/2005 |
| WO | WO2005/000137 | 1/2005 |
| WO | 2005018466 | 3/2005 |
| WO | WO2005/020829 | 3/2005 |
| WO | 2005030068 | 4/2005 |
| WO | WO2005/065374 | 7/2005 |
| WO | WO2005/065375 | 7/2005 |
| WO | 2005087121 | 9/2005 |
| WO | WO2005/082262 | 9/2005 |
| WO | WO2005/099400 | 10/2005 |
| WO | 2005102195 | 11/2005 |
| WO | WO2005/104969 | 11/2005 |
| WO | WO2006/005198 | 1/2006 |
| WO | WO2006/012088 | 2/2006 |
| WO | WO2006/017616 | 2/2006 |
| WO | WO2006/020530 | 2/2006 |
| WO | WO2006/028537 | 3/2006 |
| WO | 2006042188 | 4/2006 |
| WO | WO2006/045094 | 4/2006 |
| WO | 2006047711 | 5/2006 |
| WO | 2006079531 | 8/2006 |
| WO | WO2006/086537 | 8/2006 |
| WO | 2006096240 | 9/2006 |
| WO | 2006096351 | 9/2006 |
| WO | 2006104874 | 10/2006 |
| WO | 2006110463 | 10/2006 |
| WO | 2006119447 | 11/2006 |
| WO | WO-2006/116662 | 11/2006 |
| WO | WO2006/119241 | 11/2006 |
| WO | WO2007/002409 | 1/2007 |
| WO | 2007038350 | 4/2007 |
| WO | 2007040750 | 4/2007 |
| WO | 2007040888 | 4/2007 |
| WO | 2007041702 | 4/2007 |
| WO | 2007044705 | 4/2007 |
| WO | 2007053566 | 5/2007 |
| WO | 2007060534 | 5/2007 |
| WO | 2007075454 | 7/2007 |
| WO | 2007087628 | 8/2007 |
| WO | 2007090021 | 8/2007 |
| WO | 2007092056 | 8/2007 |
| WO | 2007092870 | 8/2007 |
| WO | 2007097905 | 8/2007 |
| WO | 2007121271 | 10/2007 |
| WO | WO2007/118045 | 10/2007 |
| WO | 2007123920 | 11/2007 |
| WO | 2007124249 | 11/2007 |
| WO | 2007127595 | 11/2007 |
| WO | 2007127604 | 11/2007 |
| WO | WO2007/124222 | 11/2007 |
| WO | WO2007/130835 | 11/2007 |
| WO | WO2007/130840 | 11/2007 |
| WO | WO2007/130941 | 11/2007 |
| WO | 2007138270 | 12/2007 |
| WO | 2007146032 | 12/2007 |
| WO | 2008005740 | 1/2008 |
| WO | 2008006098 | 1/2008 |
| WO | 2008036975 | 3/2008 |
| WO | 2008039777 | 4/2008 |
| WO | 2008042948 | 4/2008 |
| WO | 2008048923 | 4/2008 |
| WO | WO2008/045210 | 4/2008 |
| WO | 2008070716 | 6/2008 |
| WO | WO2008/069420 | 6/2008 |
| WO | 2008078163 | 7/2008 |
| WO | 2008082737 | 7/2008 |
| WO | WO2008/088731 | 7/2008 |
| WO | WO2008/088990 | 7/2008 |
| WO | WO2008/089075 | 7/2008 |
| WO | 2008100590 | 8/2008 |
| WO | 2008118295 | 10/2008 |
| WO | 2008119006 | 10/2008 |
| WO | 2008124772 | 10/2008 |
| WO | 2008134703 | 11/2008 |
| WO | WO2008/140756 | 11/2008 |
| WO | 2008157589 | 12/2008 |
| WO | 2009006225 | 1/2009 |
| WO | 2009011845 | 1/2009 |
| WO | WO2009/015100 | 1/2009 |
| WO | WO2005/013839 | 2/2009 |
| WO | 2009029928 | 3/2009 |
| WO | WO2009/036541 | 3/2009 |
| WO | 2009055407 | 4/2009 |
| WO | 2009155360 | 12/2009 |
| WO | WO2010/018316 | 2/2010 |
| WO | WO2010/018317 | 2/2010 |
| WO | WO2010/019704 | 2/2010 |
| WO | WO2010/019857 | 2/2010 |
| WO | 2010030916 | 3/2010 |
| WO | 2010045383 | 4/2010 |
| WO | 2010065648 | 6/2010 |

OTHER PUBLICATIONS

CD Horizon M8 Multi Axial Screw Spinal System Brochure, Medtronic Sofamor Danek, no publish date.
Claris Instrumentation Brochure, G Med, pub. 1997.
Contour Spinal System Brochure, Ortho Development, no publish date.
EBI Omega 21 Brochure, EBI Spine Systems, pub. 1999.
SDRS Surgical Dynamics Rod System Brochure, Surgical Dynamics, pub. 1998-99.

(56) References Cited

OTHER PUBLICATIONS

Silhouette Spinal Fixation System Brochure, SulzerMedica Spine-Tech, no publish date.
Spine, Lipcott, Williams & Wilkins, Inc. vol. 24, No. 15, p. 1495.
The Moss Miami 6.0mm System Advertisement, author unknown, no publish date.
The Rod Plate System Brochure, Stryker HowmedicaOsteonics, pub. Oct. 1999.
The Strength of Innovation Advertisement, Blackstone Medical Inc., no publish date.
Versalok Low Back Fixation System Brochure, Wright Medical Technology, Inc., pub. 1997.
VLS System Variable Locking Screw Brochure, Interpore Cross International, 1999.
Xia Spinal System Brochure, Stryker HowmedicaOsteonics, no publish date.
Brochure of Sofamor Danek the Spine Specialist, TSRH, Pedicle Screw Spinal System, Publication Date: Jan. 23, 1995.
Brochure of Spinal Concepts, InCompass, Thoracolumbar Fixation System, Publication Date: Oct. 2003.
Brochure of Spinal Concepts, Pathfinder, Minimally Invasive Pedicle Fixation System, Publication Date: May 2003.
Brochure of Spinal Concepts, Surgical Technique, InCompass, Thoracolumbar Fixation System, Publication Date: Oct. 2003.
Brochure of SpineLine, Current Concepts, Minimally Invasive Posterior Spinal Decompression and Fusion Procedures, Publication Date: Sep./Oct. 2003.
European Search Report, EP14189707.4, dated Feb. 25, 2015.

\* cited by examiner

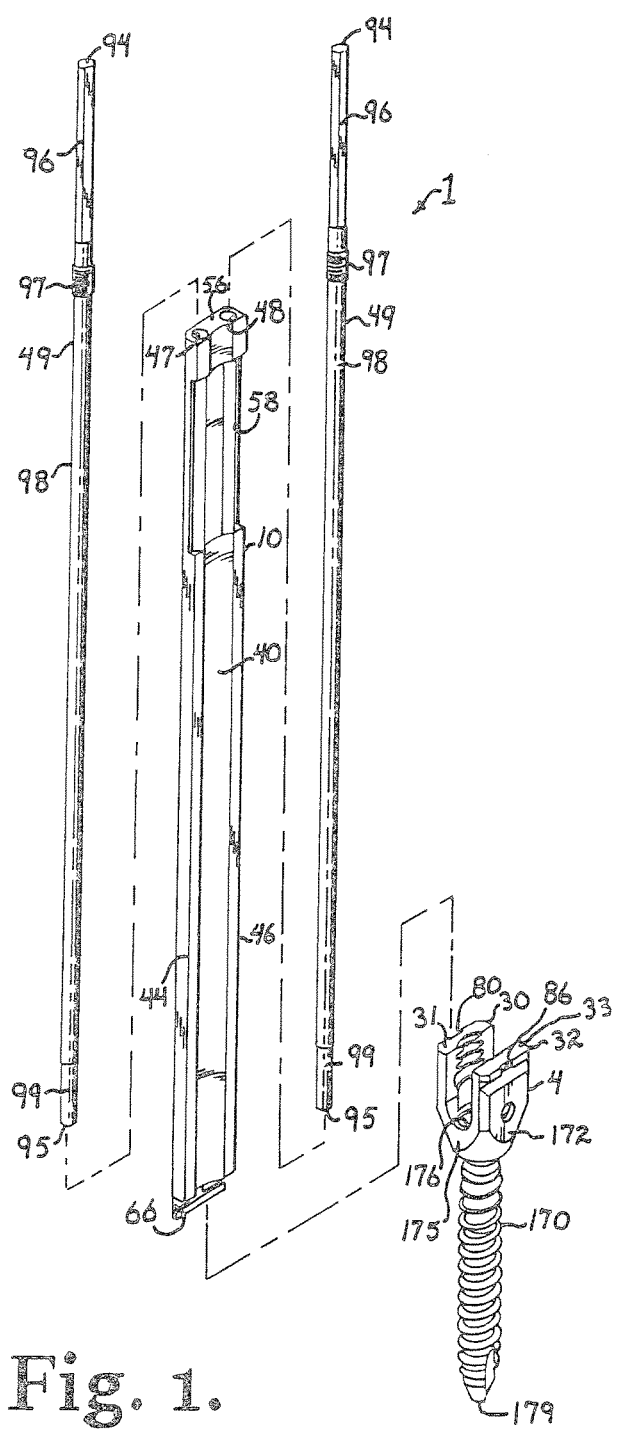
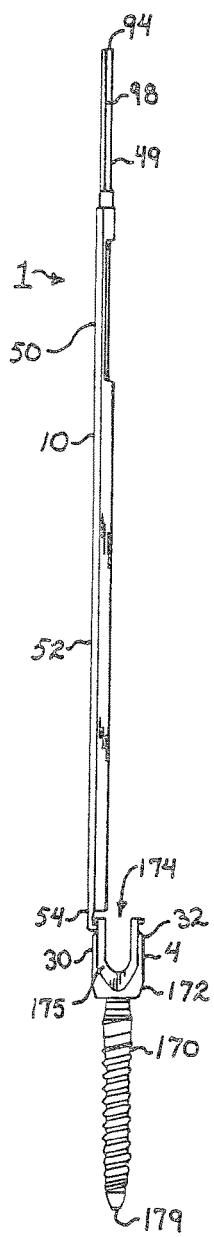
Fig. 1.
Fig. 2.

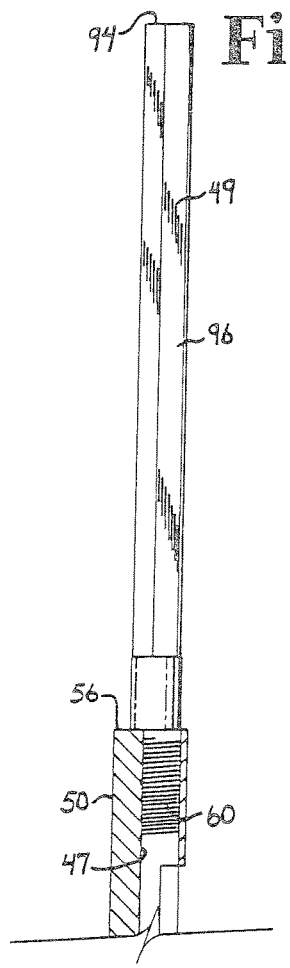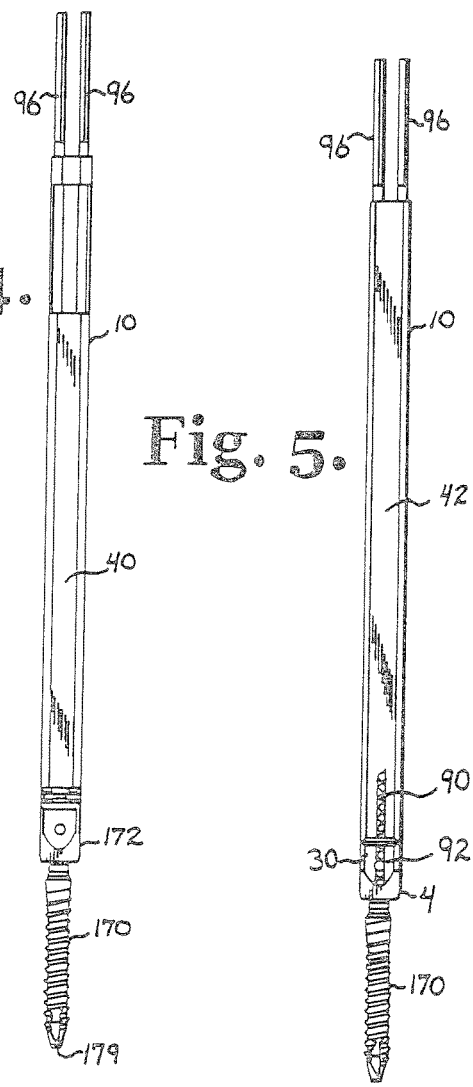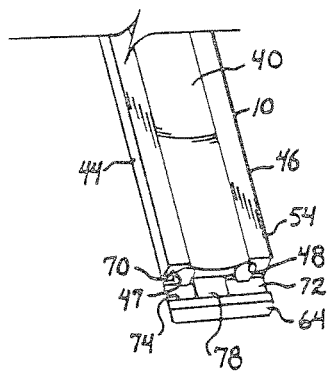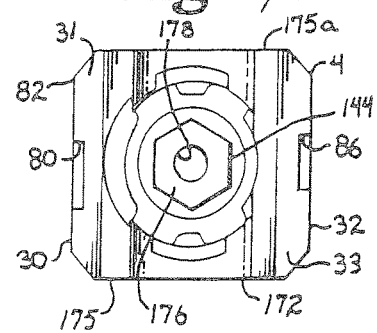

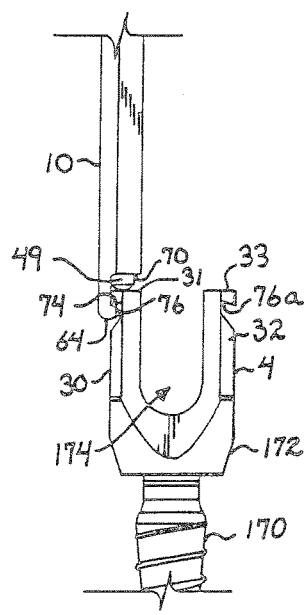
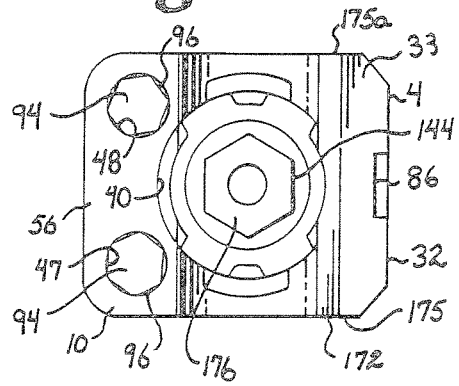
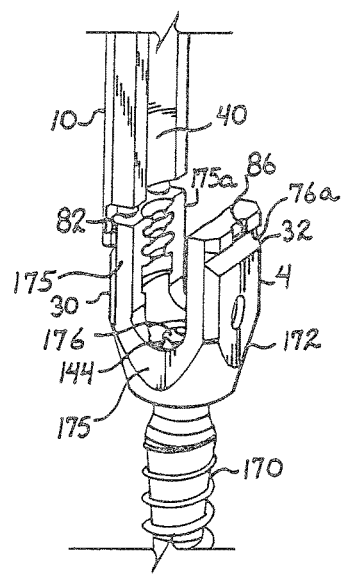

Fig. 11.
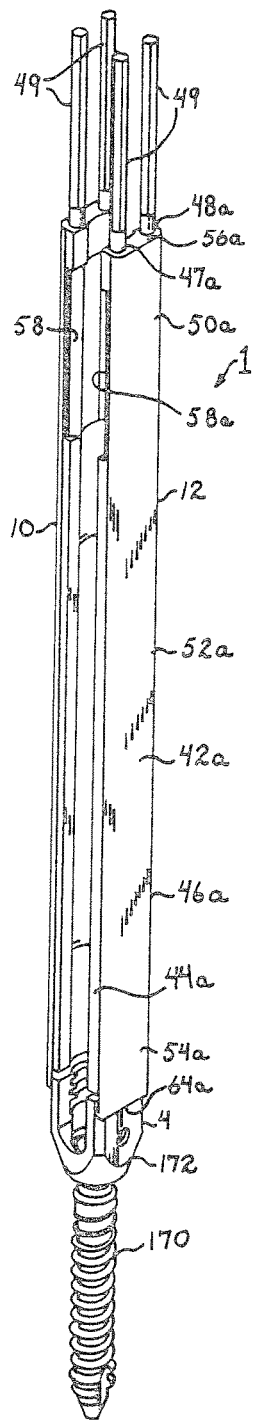
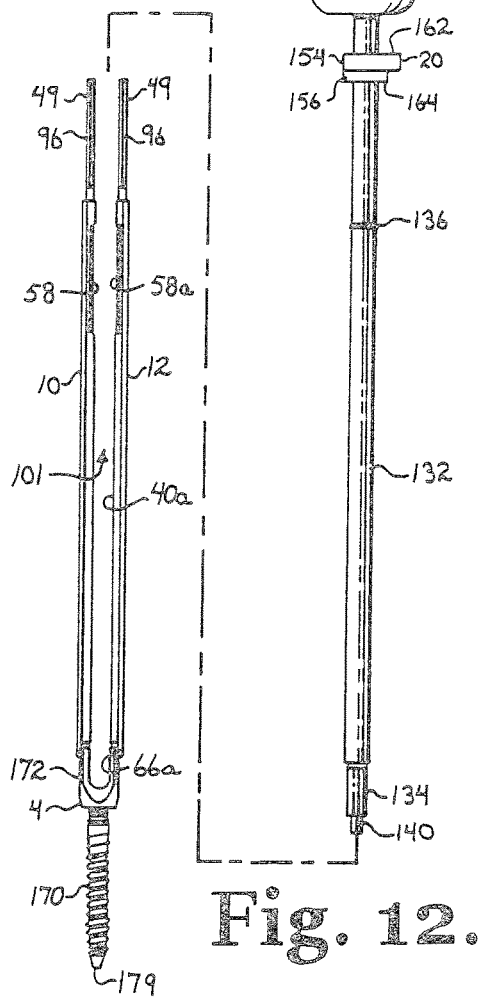
Fig. 12.

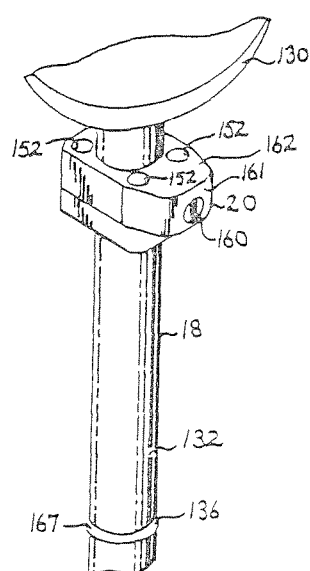
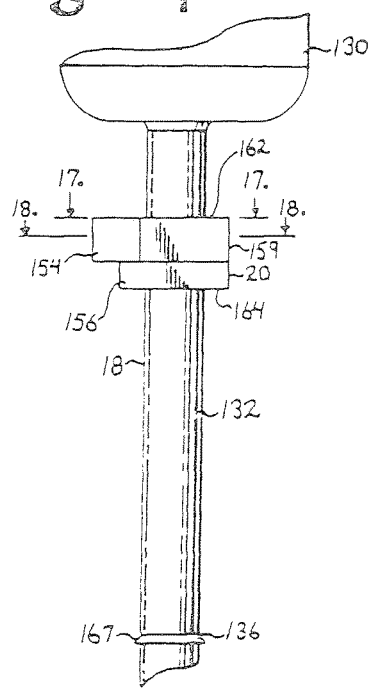
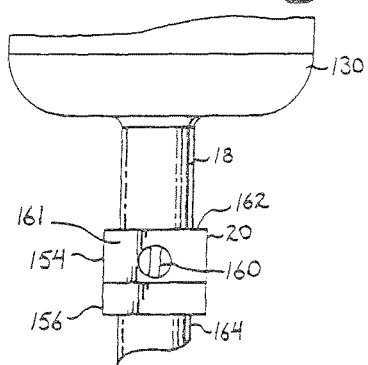
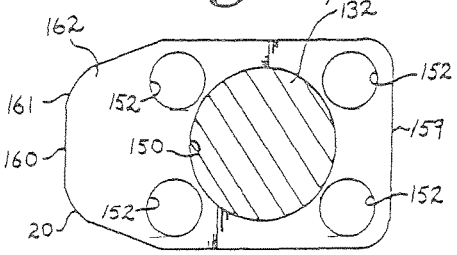
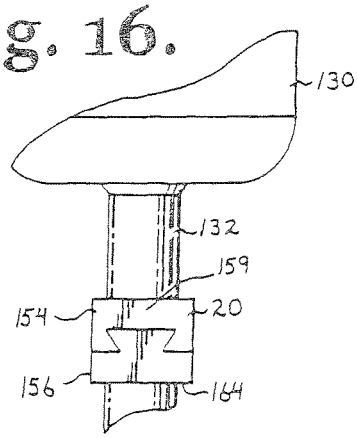
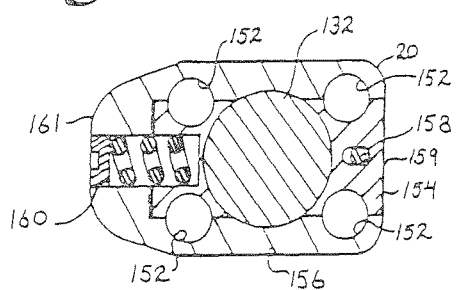

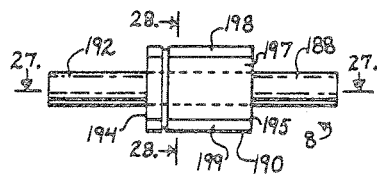
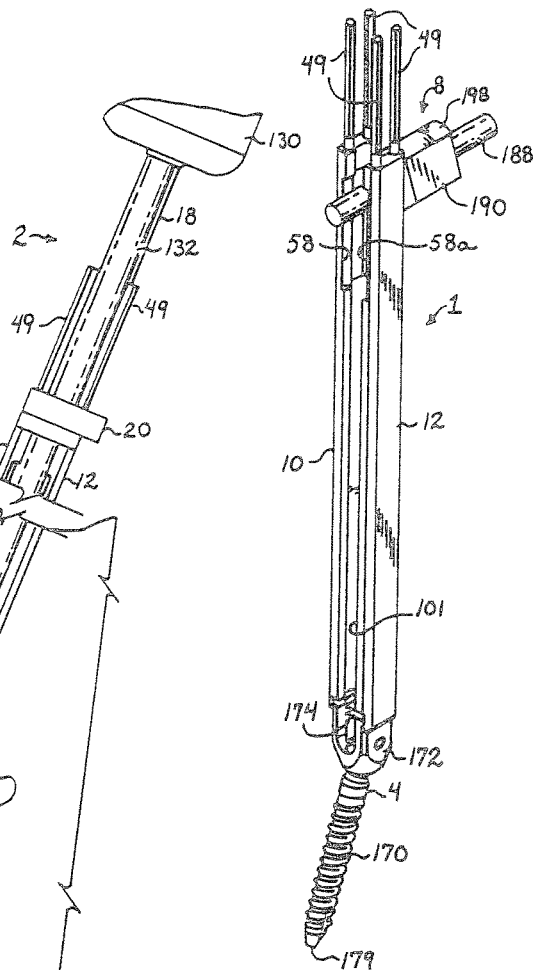
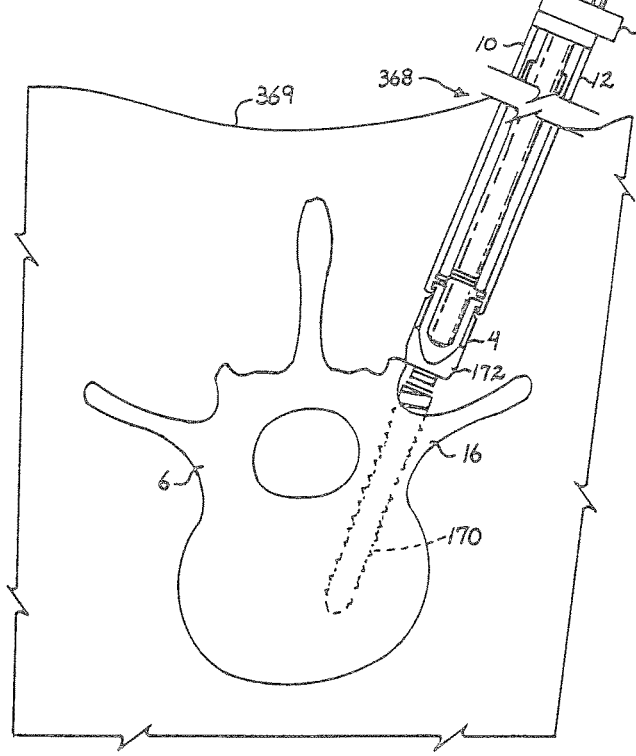

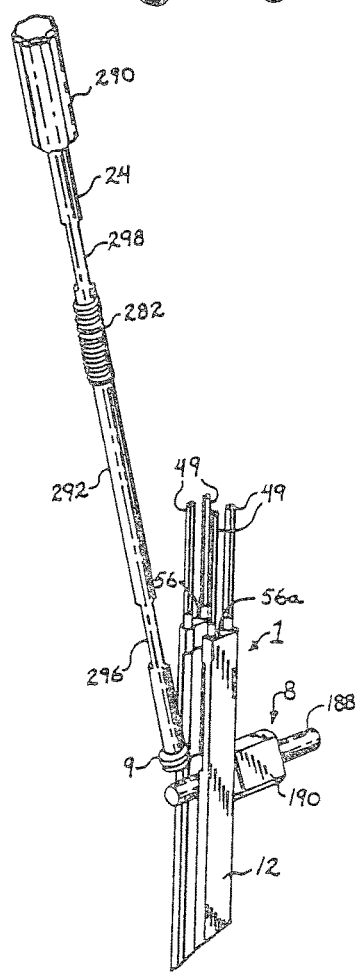
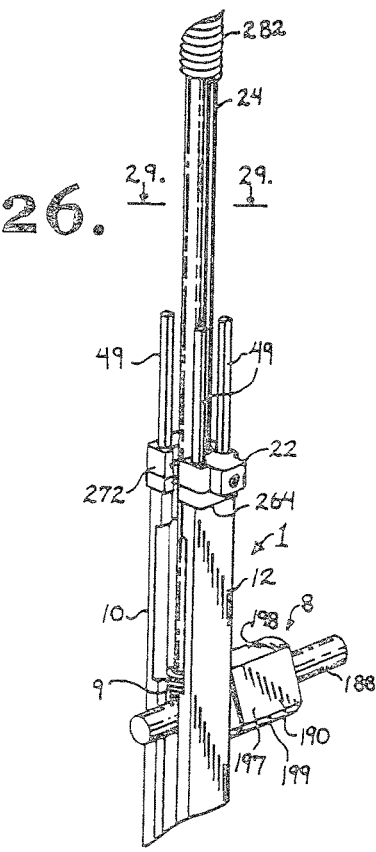
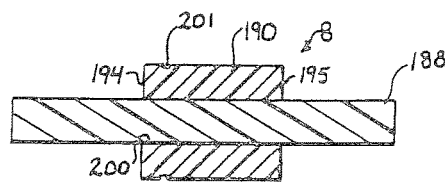
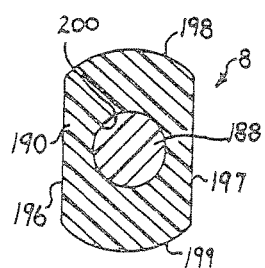

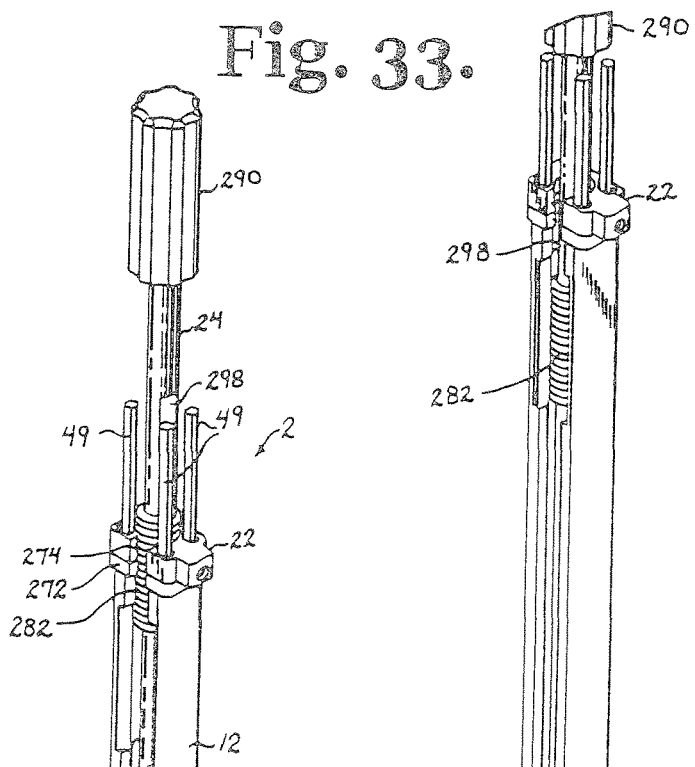
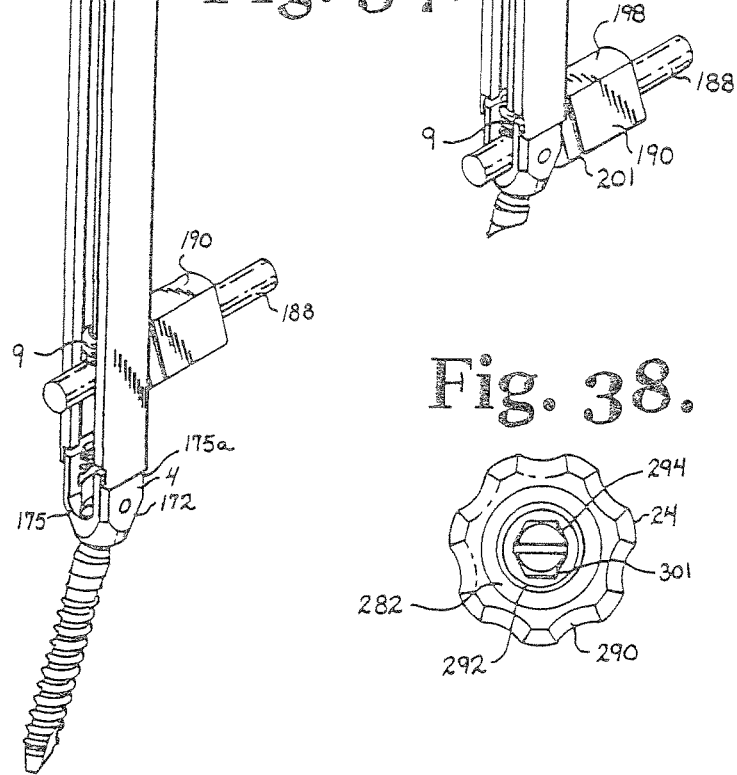
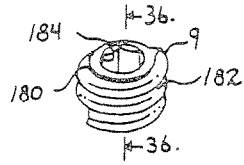
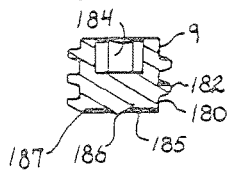
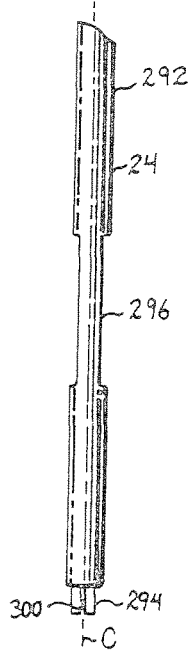
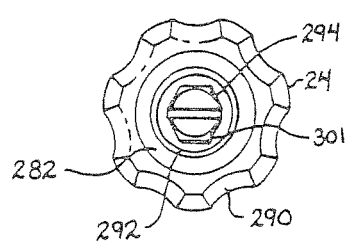

TOOL SYSTEM FOR DYNAMIC SPINAL IMPLANTS

CROSS REFERENCE TO RELATED APPLICATIONS

This application is a continuation of U.S. patent application Ser. No. 13/373,735 filed Nov. 28, 2011, which is a continuation of U.S. patent application Ser. No. 11/999,689 filed Dec. 6, 2007 that claimed the benefit of U.S. Provisional Application No. 60/873,819 filed Dec. 8, 2006 and which was a continuation-in-part of U.S. patent application Ser. No. 11/328,481 filed Jan. 9, 2006 that is a continuation in part of U.S. patent application Ser. No. 11/272,508 filed Nov. 10, 2005 and a continuation-in-part of U.S. patent application Ser. No. 10/789,149, filed Feb. 27, 2004, now U.S. Pat. No. 7,160,300, all of which are incorporated herein by reference. U.S. patent application Ser. No. 11/328,481 is also a continuation-in-part of U.S. patent application Ser. No. 10/996,289 filed Nov. 23, 2004, also incorporated by reference herein. U.S. patent application Ser. No. 11/328,481 claimed benefit of U.S. Provisional Application No. 60/725,445 filed Oct. 11, 2005 and incorporated its disclosure therein by reference, and this application also claims benefit of the 60/725,445 application.

BACKGROUND OF THE INVENTION

The present invention relates to apparatuses and methods for use in performing spinal surgery using minimally or less invasive techniques and, in particular, to tools and methods of using such tools, especially for implanting and manipulating spinal screws and for implanting flexible or otherwise dynamic longitudinal connecting members for spinal support and alignment to create, as much as possible, a more normal or natural loading pattern between the vertebrae in flexion, extension, distraction, compression, side bending and torsion.

For many years, spinal osteosynthesis apparatuses have been utilized to correct spinal deformities, injuries or disease. In such procedures, substantially rigid longitudinal connecting members, for example, elongate solid rods, are surgically attached to vertebrae of the spine to provide support and/or to realign or reposition certain vertebrae. The longitudinal connecting members are typically secured to vertebrae utilizing bone screws and other spinal implants. In order to reduce the impact of such surgery on the patient, a desirable approach is to insert such implants percutaneously or with surgical techniques that are less invasive to the body of the patient. In order to provide for protected motion with more normal or natural spinal flexibility, more flexible or dynamic longitudinal connecting members may be chosen over solid rigid rods.

Problems arise when implant deployment and insertion tools designed for traditional open surgery that is more invasive are utilized in percutaneous or less invasive surgery or with dynamic stabilization longitudinal connecting members. The tools may be bulky, oversized or have irregular surfaces or protrusions that can catch and traumatize tissues. A projecting actuator arm or fastening member may be useful with respect to the spinal screw implantation process or the rod reduction process, but there may be insufficient clearance to use such structure and/or such structure may produce additional unwanted trauma which the percutaneous surgery is attempting to avoid.

A percutaneous or less invasive procedure also presents a problem with implantation of elongate connecting members that have historically required a long incision and open wound in order to provide for the length of the connecting member and the space required for the surgeon's hands as well as the tools needed to manipulate the rod. Such problems are then compounded by the implants and insertion tools used with the connecting member.

Consequently, it is desirable to develop apparatuses and techniques that allow for the insertion of bone screws or other bone attachment structures, the insertion and reduction of longitudinal connecting members into the bone screws and the securing of the connecting member to the bone screws with significantly less invasion into the body of the patient.

Historically, it also has been common to fuse adjacent vertebrae that are placed in fixed relation by the installation therealong of bone screws or other bone anchors and cooperating longitudinal connecting members or other elongate members. Fusion results in the permanent immobilization of one or more of the intervertebral joints. Because the anchoring of bone screws, hooks and other types of anchors directly to a vertebra can result in significant forces being placed on the vertebra, and such forces may ultimately result in the loosening of the bone screw or other anchor from the vertebra, fusion allows for the growth and development of a bone counterpart to the longitudinal connecting member that can maintain the spine in the desired position even if the implants ultimately fail or are removed. Because fusion has been a desired component of spinal stabilization procedures, longitudinal connecting members have been designed that are of a material, size and shape to largely resist bending (flexion, extension and sideways), twisting (torsion), compression and distraction, and thus substantially immobilize the portion of the spine that is to be fused. Thus, longitudinal connecting members are typically uniform along an entire length thereof, and usually made from a single or integral piece of material having a uniform diameter or width of a size to provide substantially rigid support.

Fusion, however, has some undesirable side effects. One apparent side effect is the immobilization of a portion of the spine. Furthermore, although fusion may result in a strengthened portion of the spine, it also has been linked to more rapid degeneration and even hyper-mobility and collapse of spinal motion segments that are adjacent to the portion of the spine being fused, reducing or eliminating the ability of such spinal joints to move in a more normal relation to one another. In certain instances, fusion has also failed to provide pain relief.

An alternative to fusion and the use of more rigid longitudinal connecting members or other rigid structure has been a "soft" or "dynamic" stabilization approach in which more elastic materials and/or shapes are utilized for a longitudinal connecting member fixed between a pair of bone anchors, such as pedicle screws, in an attempt to create, as much as possible, a more normal loading pattern between the vertebrae in flexion, extension, compression, distraction, side bending and torsion. Tools utilized with traditional rods or other more rigid structure may not be appropriate for manipulating more flexible and variously sized connecting members and cooperating bone attachment structures. The dynamic conditions associated with spinal movement therefore provide a challenge not only for the design of more flexible or elastic longitudinal connecting members, but also for the design of cooperating tooling.

SUMMARY OF THE INVENTION

A tool assembly and a set of tools according to the invention is provided for percutaneous or less invasive methods of implanting bone screws and an associated spinal connecting member in a patient. The tool assembly includes an elongate guide tool having structure at a lower end thereof that is operably mateable with opposed sides of a bone attachment receiver. The elongate guide tool includes first and second discreet, independently attachable and movable parts or members. The independent members allow for movement toward and away from one another, aiding insertion and manipulation of manipulation tools and other bone attachment structure.

Also according to the invention, a stabilizer is provided for placing the first and second members into a set spaced relation with one another when desired, for example, during driving of a bone screw shank into a vertebra and/or reducing a longitudinal connecting member and closure structure down between the first and second members and into the bone attachment structure. Both an independent stabilizer and a stabilizer attached to a bone screw driver may be included in a tool set according to the invention. Further tools include a cooperating bone screw driver with an attached stabilizer, a closure starter/reduction tool, a closure driver and a counter torque tool.

Objects and Advantages of the Invention

Therefore, the objects of the present invention include: to provide a compact tool assembly for supporting and installing bone attachment structures, such as bone screws, hooks and dynamic stabilization connecting members and other spinal implants with minimal or less surgical invasion to the patient; to provide such an assembly in which elongate holding members may be independently manipulated and form an open, expandable channel when desired and may also be placed into set spacial relation when desired; to provide a set of tools for implanting a dynamic spinal fixation connecting member for support or alignment along a human spine with minimal or less surgical invasion of the patient; to provide such a set of tools including an insertion tool, driving, reduction and manipulation tools for use in implanting a bone attachment implant, directing a longitudinal connecting member downwardly into such an implant and capturing the longitudinal connecting member within a receiver of the bone attachment implant; to provide such a set of tools including a closure reduction and installation tool for securing the dynamic fixation connecting member to the bone attachment implant; to provide such a set of tools wherein the insertion, driving and manipulation tools are easily attached to and disengaged from the bone attachment implants; to provide such a set of tools wherein the insertion tools, supports or stabilizers, deployment tools, reduction tools, bone implant installation tools and closure installation tools are all easily aligned, positioned, and engaged, if necessary, with respect to the bone implants and are disengaged from the bone implants and other tools in the installation assembly by manual manipulation of the surgeon; to provide a method of implanting a dynamic stabilization connecting member into bone implants within a patient with minimal or less surgical invasion of the patient; to provide such a method utilizing the previously described tools for implantation of such a connecting member; and to provide such a set of tools and methods that are easy to use and especially adapted for the intended use thereof and wherein the tools are comparatively inexpensive to produce.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is an exploded perspective view of a portion of a tool assembly according to the present invention showing a first elongate member of an open guide tool, a pair of lock pins and a cooperating polyaxial bone screw.

FIG. 2 is a reduced side elevational view of the portion of the tool assembly and the polyaxial bone screw of FIG. 1, shown assembled.

FIG. 3 is an enlarged and partial side elevational view of the assembly of FIG. 2 with portions broken away to show the detail thereof.

FIG. 4 is a reduced front elevational view of the tool assembly and the polyaxial bone screw of FIG. 1, shown assembled.

FIG. 5 is a reduced rear elevational view of the tool assembly and the polyaxial bone screw of FIG. 1, shown assembled.

FIG. 6 is an enlarged and partial perspective view of the first elongate member of FIG. 1.

FIG. 7 is an enlarged top plan view of the polyaxial bone screw of FIG. 1.

FIG. 8 is an enlarged and partial side elevational view of the assembly shown in FIG. 2.

FIG. 9 is an enlarged and partial perspective view of the assembly shown in FIG. 8.

FIG. 10 is an enlarged top plan view of the assembly and polyaxial bone screw shown in FIG. 2.

FIG. 11 is a perspective view of the tool assembly of FIG. 1 and further showing a second elongate member of the open guide tool and a second pair of lock pins cooperating with the polyaxial bone screw.

FIG. 12 is a reduced side elevational view of the assembly of FIG. 11 shown with a cooperating polyaxial bone screw driver and attached elongate member stabilizer.

FIG. 13 is an enlarged and partial perspective view of the driver and stabilizer of FIG. 12.

FIG. 14 is an enlarged and partial opposing side elevational view of the driver and stabilizer of FIG. 12.

FIG. 15 is an enlarged and partial front elevational view of the driver and stabilizer of FIG. 12.

FIG. 16 is an enlarged and partial rear elevational view of the driver and stabilizer of FIG. 12.

FIG. 17 is a cross-sectional view taken along the line 17-17 of FIG. 14.

FIG. 18 is a cross-sectional view taken along the line 18-18 of FIG. 14.

FIG. 22 is a reduced and partial front elevational view of the cooperating driver and guide tool of FIG. 21, shown driving the polyaxial bone screw into a vertebra.

FIG. 23 is a reduced perspective view of the open guide tool and attached bone screw of FIG. 11, the bone screw now implanted in a vertebra as shown in FIG. 22 and further shown with a longitudinal connecting member having an elongate member and a sleeve.

FIG. 24 is a front elevational view of the longitudinal connecting member of FIG. 23.

FIG. 25 is a partial perspective view, similar to FIG. 23, further showing a closure top starter/reduction tool according to the invention holding a closure top.

FIG. 26 is an enlarged and partial perspective view, similar to FIG. 25 further showing a guide stabilizer according to the invention.

FIG. 27 is a cross-sectional view taken along the line 27-27 of FIG. 24.

FIG. 28 is a cross-sectional view taken along the line 28-28 of FIG. 24.

FIG. 33 is a perspective view of the assembly of FIG. 30 shown in a longitudinal connecting member reduction step subsequent to that shown in FIG. 30.

FIG. 34 is a perspective view of the assembly of FIGS. 30 and 33 shown in a subsequent closure top engagement step.

FIG. 35 is a perspective view of the closure top of FIGS. 25, 26, 30, 33 and 34.

FIG. 36 is a cross-sectional view taken along the line 36-36 of FIG. 35.

FIG. 37 is an enlarged and partial side elevational view of the closure starter/reduction tool of FIGS. 25, 26, 29, 30, 33, and 34.

FIG. 38 is an enlarged bottom plan view of the closure starter/reduction tool of FIG. 37.

DETAILED DESCRIPTION OF THE INVENTION

Figure 19:
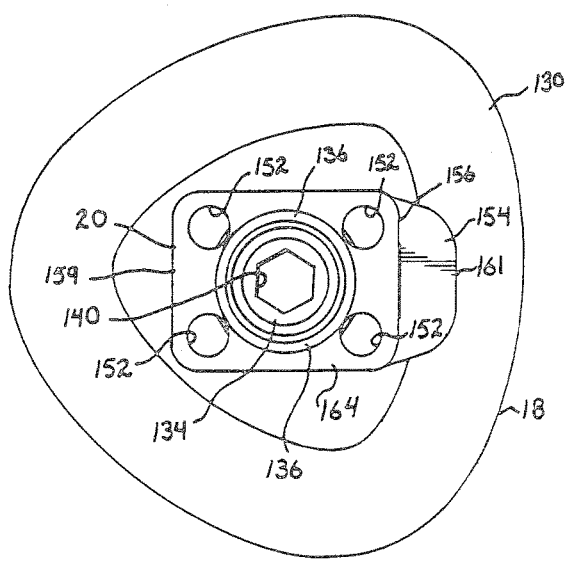
FIG. 19 is an enlarged bottom plan view of the driver and stabilizer of FIG. 12.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

It is also noted that any reference to the words top, bottom, up and down, and the like, in this application refers to the alignment shown in the various drawings, as well as the normal connotations applied to such tools and cooperating devices, and is not intended to restrict positioning of the tools in actual use. It is also noted that reference to words such as front, back, anterior and posterior used in this application also refer to the alignment shown in the various drawings, and in particular, when possible, with reference to the human spine and human body, but also is not intended to restrict positioning of the tools in actual use.

With particular reference to FIGS. 1-11, the reference numeral 1 generally designates a guide tool assembly according to the present invention that may be used alone or in combination with a variety of cooperating tools described herein that may make up a tool set 2 (see, e.g., FIGS. 12, 22, 25, 33 and 43) according to the invention for use in installing at least one and up to a plurality of bone screws 4 into a patient's spine 6, followed by the installation of a longitudinal member, such as the member generally 8 and up to a plurality of closure members or tops 9, into the bone screws 4 in a process according to the present invention.

The guide tool assembly 1 is open, having a first elongate member 10 and a separate or discrete second elongate member 12, each of the members 10 and 12 being engageable with the bone screw 4 as will be described more fully below. The open arrangement of the guide tool assembly 1 allows for independent manipulation of the elongate members 10 and 12 and insertion of a variety of tools, implants and longitudinal connecting members, some with sleeves or spacers having various widths or diameters. When more stability is desired, for example, during installation of the bone screw 4 into a vertebra 16 of the patient's spine 6, a driver 18 or other manipulating tool being used in connection with the guide tool assembly 1 may include a stabilizer 20 (described more fully below) for keeping the elongate members 10 and 12 in fixed spaced relation to one another.

Furthermore, according to the invention, the assembly 1 may include a discrete or independent stabilizer 22 for use with a variety of tools, including, but not limited to the following illustrated tools: a closure starter/connecting member reducer 24, a closure driver 26 and a counter torque tool 28, all of which will be described more fully below.

The guide tool assembly 1 elongate members 10 and 12 are substantially similar to one another, sized and shaped for attachment to respective first and second arms 30 and 32 of the bone screw 4, the first arm having a top surface 31 and the second arm having a top surface 33. The elongate members 10 and 12 are generally sized and shaped to be sufficiently long to extend from an implanted bone screw 4 through an exterior of a patient's skin so as to provide an outwardly extending and upper handling portion that allows and provides for gripping by a surgeon during procedures utilizing the guide tool assembly 1, with or without the other cooperating tools. Specifically, the elongate member 10 is a singular discrete structure generally including an inner wall or surface 40 and an opposed outer wall or surface 42. The member 10 further includes opposed substantially parallel sides 44 and 46. The member 10 has a substantially constant width as measured between the sides 44 and 46, such width being substantially the same as a width of a cooperating bone screw arm 30. The sides 44 and 46 may be beveled along an entire length thereof as illustrated in the drawing figures. The back wall 42 is substantially planar along an entire length thereof. The front wall 40 has a concave curvature that substantially matches or corresponds to the inner curvature of the bone screw arm 30 that is in turn sized and shaped for mating cooperation with the substantially cylindrical closure member or top 9. The front wall 40 also is sized and shaped to receive and allow passage of both tools and implants as will be described more fully below. Running along a length of the member 10 and near respective sides 44 and 46 are a pair of substantially cylindrical through channels 47 and 48, each sized and shaped to receive one of a pair of cooperating lock pins 49.

The elongate members 10 and 12, stabilizer 22, lock pins 49 and other cooperating tooling may be made from a variety of suitable materials, including but not limited to metals, metal alloys, plastics, polymers, composites and blends thereof. For example, the tool components may be made from stainless steel, titanium, polymer blends that may be carbon reinforced, such as a polyetheretherketone (PEEK) and or other radiolucent or non-radiolucent materials. In certain embodiments the members 10 and 12 may be rigid and in other embodiments, more flexible, allowing for bending of the members 10 and 12 and associated pins 49 without compromising strength of the components or attachment to a cooperating bone anchor.

The member 10 may further be described as having an upper, handling portion 50, an intermediate portion 52 and a lower implant engaging portion 54. The upper handling portion 50 includes a top surface 56 and a cut-out or recessed portion 58 substantially formed in the front wall or surface 40 and sized and shaped to provide access for tools and/or bone attachment components, the recessed portion 58 cooperating with a similar or identical recessed portion 58a on the member 12 as illustrated, for example, in FIGS. 11, 25 and 26. The channels 47 and 48 open to the top surface 56. Also, near the top surface, wall portions 60 forming the channels 47 and 48 are threaded for mating cooperation with a threaded portion of the lock pin 49 as will be described in greater detail below.

The lower implant engaging portion 54 includes a bottom surface 64 and a cut-out or recess 66 near such bottom surface that is formed in the wall 40 and also extends through a portion of the sides 44 and 46. With particular reference to FIGS. 6, 8 and 9, the cut-out 66 is defined by an upper surface 70 disposed substantially perpendicular to the outer surface 42, an inner planar surface 72 disposed substantially parallel to the outer surface 42 and a substantially planar lip surface 74 disposed at an acute angle with respect to the surface 72. With particular reference to FIG. 8, in the illustrated embodiment, the lip surface 74 is substantially parallel with the bottom surface 64, forming a narrow strip that projects away from the inner wall 40 and is sized and shaped to engage and fit within a groove 76 of the arm 30 of the bone screw 4.

With particular reference to FIGS. 6 and 7, the inner surface 72 further includes a raised strip or projection 78 that runs perpendicular to the lip surface 74 and is sized, shaped and positioned to slidingly engage with a slit 80 in a ledge 82 that partially defines the groove 76 disposed on the arm 30 of the bone screw 4. The raised strip 78 and the slit 80 are designed to ensure proper mating of the insertion tool 10 and the bone screw arm 30 and differentiate between the elongate member 10 and the elongate member 12 such that the member 10 only fits on the bone screw arm 30 and the member 12 only fits on the bone screw arm 32. The member 12 also includes a raised strip (not shown), similar to the strip 78, that is sized, shaped and positioned to slidingly engage with a slit 86 of the arm 32. The slits 80 and 86 may be disposed indirectly opposite of one another and the cooperating strips positioned on the tool 1 such that the member 10 only mates with the arm 30 and the member 12 only mates with the arm 32. The cooperation between the strip 78 and the slit 80 and the similar strip on the member 12 and the slit 86 ensures proper overall alignment and mating of the tool 1 and the bone screw 4 when both members 10 and 12 are in engagement with the bone screw 4, and further prohibits front to back movement of the bone screw 4 with respect to the insertion tool 1 when the members 10 and 12 are mounted on the screw 4 and the lock pins 49 are in contact with the bone screw 4. With reference to FIG. 5, the back wall 42 of the member 10 may include a laser etched alignment stripe 90 that aids a surgeon in properly aligning and mating the member 10 with the arm 30 by simply aligning the stripe 90 with a stripe 92 that is located on only the arm 30. It is noted that bone screws 4 and members 10 and 12 according to the invention may be configured to include uniform and opposite cooperating strips and slits so that the members 10 and 12 may be engaged with either the arm 30 or the arm 32 of the bone screw 4.

Each lock pin 49 is elongate, having a top surface 94 a curved bottom surface 95, a hex-shaped upper driving portion 96 disposed near the top surface 94 and a threaded portion 97 disposed near the driving portion 96 and on a smooth cylindrical body portion 98 of the lock pin 49. The smooth body portion 98 extends from the driving portion 96 to the bottom surface 95. As illustrated in FIG. 1, near the bottom surface 95, the body portion 98 may be of slightly reduced diameter as shown by the portion 99 to result in the bottom surface 95 being of a size and shape to fully contact the bone screw 4 without overhanging the arm 30 or 32. The lock pin 49 is sized and shaped to be received in either of the cylindrical channels 47 and 48 in either of the members 10 and 12, with the threaded portion 97 rotatably receivable in the threaded inner wall 60. The lock pin 49 is sized and shaped to extend along and completely through the channels 47, 48 until the curved bottom 95 abuts the top surface 31 or 33 of the bone screw 4 with the upper driving portion 96 extending above the top 56 of the member 10 as illustrated, for example, in FIG. 3.

The lock pins 49 are rotated and driven downwardly into the member 10 by a socket driver (not shown). A suitable driver includes a substantially cylindrical elongate body and an elongate hex-shaped aperture or driving socket sized and shaped to receive and mate with the hex-shaped upper driving portion 96 of each of the lock pins 49.

As illustrated in FIGS. 11 and 12, the member 12 is substantially similar to the member 10 in size and shape, having an inner wall 40a, and outer wall 42a, sides 44a and 46a, channels 47a and 48a, upper intermediate and lower portions 50a, 52a and 54a, respectively, a top surface 56a, a recessed portion 58a, a bottom surface 64a and a recess 66a, identical or substantially similar to respective elements 40, 42, 44, 46, 47, 48, 50, 52, 54, 56, 58, 64 and 66, described herein with respect to the member 10. The member 12 channels 47a and 48a cooperate with the lock pins 49 in a manner identical to that described herein with respect to the member 10 with each channel including a threaded portion (not shown) identical or substantially similar to the threaded channel portion 60. The recess 66a is identical to the recess 66 with the exception of the inner strip that is similar to the strip 78 but disposed at a different location to cooperate with the slit 86 of the bone screw arm 32 as already described herein.

With reference to FIGS. 11 and 12, when the members 10 and 12 are mated with respective arms 30 and 32 of the bone screw 4, the members 10 and 12 may be independently manipulated toward and away from one another, as will be described in greater detail below. Also a through channel 101 is formed between the members 10 and 12 extending along the entire length of the tool 1 from the bone screw 4 to the lock pin top surfaces 94. The channel 101 is sized and shaped to receive and allow passage of both tools and implants. As will be discussed more fully below, an opening formed between the recessed portions 58 and 58a provide clearance to readily receive a driving end of the bone screw driver 18 as well as the closure top 9 and the longitudinal connecting member 8.

With reference to FIGS. 12-22, the bone screw driver 18 includes an upper elongate handle 130; an elongate shaft 132; and a driving end portion 134 integral with or fixedly attached to the shaft 132; all extending along an axis of rotation A. The handle 130 is somewhat triangular when viewed on end as shown in FIG. 19. The handle 130 may include shallow apertures to aid a surgeon in gripping and rotating the handle 130. The handle 130 is fixed to and coaxial with the shaft 132. A screw driver lock limit 136 and the stabilizer 20 are disposed on the shaft 132. The driving end portion 134 extends from the shaft 132 and is of reduced diameter. Integral or attached to the end portion 134 is a hex-shaped driving socket 140 sized and shaped to mate with a hex drive 144 formed in a shaft of the bone screw 4. Although a socket type driver is shown, a driver according to the invention may have any of a variety of driving features designed to mate with a driving head, socket, or other external or internal driving feature of a cooperating bone screw. The driving tool 18 may include a longitudinal through bore formed along an entire length thereof to cooperate with cannulated bone screws, allowing for insertion of the driver 18 and cooperating engaged bone screw over guide wires or pins.

With particular reference to FIGS. 13-18, the stabilizer 20 is located on the shaft 132 between the handle 130 and the lock limit 136. The stabilizer 20 includes a substantially central through bore 150 through which the driver shaft 132 extends, the stabilizer 20 being slidingly received on the shaft 132 along the axis A between the handle 130 and the lock limit 136. The stabilizer 20 further includes four smaller, uniformly shaped through bores 152 positioned evenly about the bore 150 and running substantially parallel to the bore 150 (and the shaft 132). The bores 152 are substantially circular in cross-section, being sized, shaped and positioned to slidingly receive four lock pins 49 and hold such pins in spaced alignment when the lock pins 49 are attached to the elongate members 10 and 12 and contact the bone screw 4 and the stabilizer 20 is seated on the members 10 and 12. The stabilizer 20 further includes an upper portion 154 and an attached lower portion 156, the upper and lower portions shaped to engage one another in a dovetail arrangement as shown in FIGS. 16 and 18. As illustrated in FIG. 18, the upper and lower portions are attached by means of an assembly pin 158 that extends through the upper and lower portions 154 and 156 near one side 159 and a laterally loaded spring retainer 160 at an opposite side 161. At the side 161, the upper portion 154 extends beyond the lower portion 156 in a lateral direction perpendicular to the axis A, providing a ledge for ease in moving the stabilizer 20 up and down the shaft 132 along the axis A. It is foreseen that the stabilizer 20 may be constructed in other ways, for example, of singular molded construction. The stabilizer 20 further includes substantially planar parallel top and bottom surfaces 162 and 164, respectively. The bottom surface 164 contacts and seats upon the upper surfaces 56 and 56a of respective members 10 and 12 and in slidable engagement therewith when the stabilizer 20 is slid downwardly along the shaft 132 and received over the lock pins 49, placing the members 10 and 12 into a parallel arrangement with one another, providing control over the device 1 during rotation of the driver 18 about the axis A when the driver 18 is used to implant the bone screw 4 into a vertebra 16.

Figure 20:
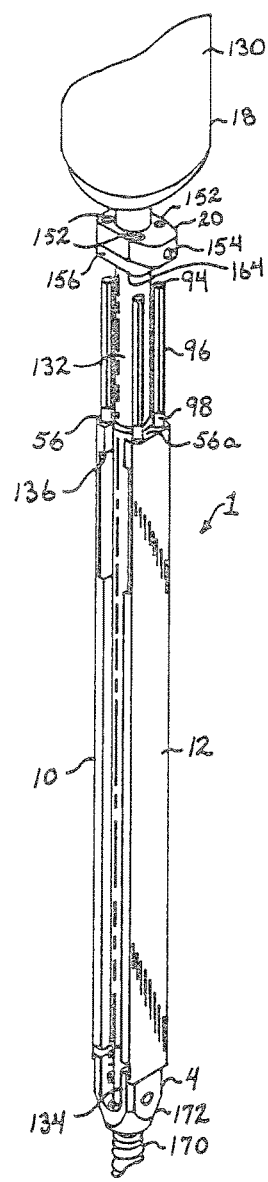
FIG. 20 is a partial perspective view of the assembly and driver of FIG. 12 showing the driver inserted into the assembly.
Figure 21:
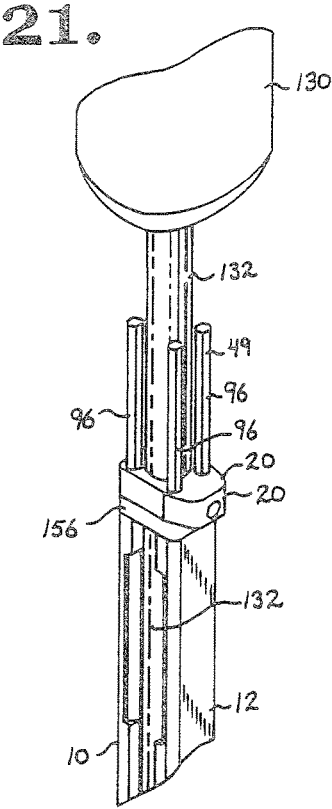
FIG. 21 is an enlarged and partial perspective view similar to FIG. 20, showing the driver stabilizer engaged with both elongate members of the open guide tool.

With reference to FIGS. 13, 14 and 19, for example, the illustrated lock stop 136 is annular and extends outwardly radially from the shaft 132 generally in a direction perpendicular to the axis A and includes a top outwardly and downwardly sloping or conical surface 167. The stop 136 is fixed to the shaft 132 at a location such that the stabilizer 20 does not slide completely down the shaft 132 prior to being positioned between the members 10 and 12 and over the lock pins 49. With reference to FIGS. 20 and 21, the stop 136 is also positioned at a location along the shaft 132 so that when the stabilizer 20 abuts against the slanted surface 167 of the lock stop 136, the stabilizer 20 also squarely and evenly seats on the members 10 and 12 with the hex socket driving head 140 being in engagement with the bone screw hex drive 144 of the bone screw 4 that is attached to the members 10 and 12. When in such position, the stabilizer 20 places the members 10 and 12 into set spacial relationship with one another, preventing outward or inward movement of the members 10 and 12 away or toward the axis A, allowing for ease in rotation of the driver 18 during implantation of the bone screw 4.

It is noted that the present invention is not intended to be restricted for use with a particular type of bone screw 4 or other bone attachment structure, bone screw closure mechanism, or longitudinal connecting member. It is foreseen that the guide tool assembly 1 and the tool set 2 of the present invention can be used with virtually any type of bone screw, including, but not limited to, fixed monoaxial, hinged and polyaxial bone screws and hooks of many different types that include features for engagement with the members 10 and 12 as described herein.

With respect to the illustrated polyaxial bone screw 4 shown in FIGS. 1, 2, 7, 9 and 10, in addition to the arms 30 and 32, the bone screw 4 further includes a threaded shank 170 in pivotal relationship with a receiver 172. The previously described arms 30 and 32 define a portion of the receiver 172. As previously described herein, the arm 30 includes the V-shaped or undercut tool engagement groove 76 that engages the lip surface 74 of the elongate member 10. The arm 32 includes a similar undercut or groove 76*a* that engages the lip surface 74*a* of the elongate member 12. The arms 30 and 32 also define a longitudinal connecting member receiving channel 174 passing therethrough between outer substantially planar surfaces 175 and 175*a*. The bone screw shank 170 includes an upper portion 176 that extends into the receiver 172 and is operationally secured therein, so that the receiver 172 is rotatable on the shank 170 until locked in position through engagement with the longitudinal connecting member 8 or compression insert (not shown) disposed between the connecting member 8 and the upper portion 176 under pressure. For example, the shank 170 may be connected to the head utilizing a spline capture connection as illustrated in the drawing figures and disclosed in U.S. Pat. No. 6,716,214 from U.S. patent application Ser. No. 10/464,633, which is incorporated by reference herein. The illustrated bone screw 4 is also cannulated, having a through bore 178 extending from a top of the shank upper portion 176 to a bottom or tip 179 of the shank.

With reference to FIGS. 25, 35 and 36, the illustrated closure structure, top or fastener 9 closes between the spaced bone screw arms 30 and 32 to secure the longitudinal connecting member 8 in the channel 174. The closure top 9 can be any of many different plug type closures. Preferably the closure top 9 has a cylindrical body 180 with a helically wound mating guide and advancement structure 182. The guide and advancement structure 182 can be of any type, including V-type threads, buttress threads, reverse angle threads, or square threads. Preferably the guide and advancement structure 182 is a helically wound flange form that interlocks with a reciprocal flange form as part of a guide and advancement structure on an interior of the bone screw arms 30 and 32. A suitable locking guide and advancement structure of this type is disclosed in U.S. Pat. No. 6,726,689 from U.S. patent application Ser. No. 10/236,123 which is incorporated by reference herein. The illustrated closure 9 is provided with a non-round driving feature that is illustrated as an opening 184, such as an Allen or Torx type of opening, to receive the similarly shaped closure starter/reduction tool 24 and closure driver 26, as will be described more fully below, to advance the closure top 9 into the receiver 172. Alternatively, the closure top 9 may be equipped with a break-off head (not shown) that breaks from the threaded cylindrical body 180 upon the application of a preselected torque, such as 95 to 120 inch-pounds. Such a break-off head would include an inner drive feature or a faceted exterior configured to mate with a similarly shaped driver of a final closure driving or torquing tool (not shown). The closure top 9 further includes a bottom surface 185 having a point 186 and outer rim 187 extending therefrom. In some embodiments an insert may be provided for placement between the closure top 9 and the longitudinal connecting member 8, such as a compression insert having a curved surface to closely grip a cooperating curved surface of the member 8.

Figure 49:
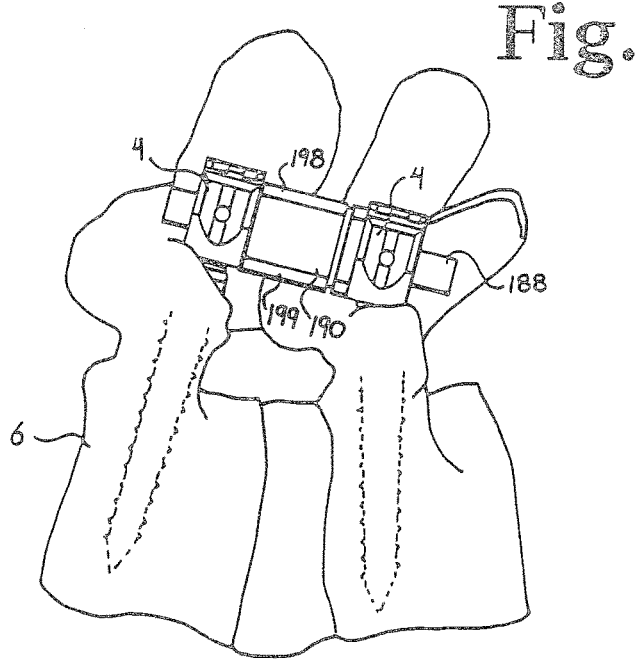
FIG. 49 is a partial and generally schematic view of a patient's spine, showing an implanted polyaxial bone screw and connecting member, similar to that shown in FIG. 48 and further connected to a second polyaxial bone screw.
Figure 50:
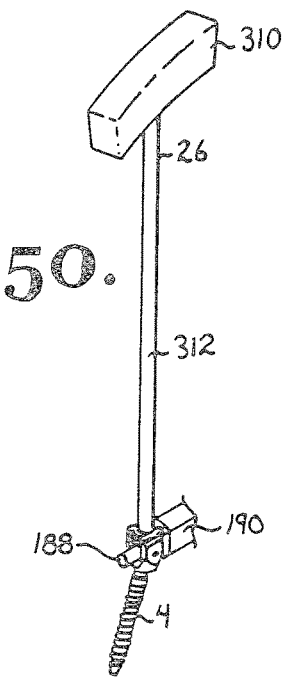
FIG. 50 is a reduced perspective view similar to FIG. 48 further showing the closure top driver of FIG. 41 being used to remove the closure top.

With particular reference to FIGS. 23-29, the illustrated longitudinal connecting member 8 cooperates with two or more bone screws 4 and is a non-fusion dynamic stabilization longitudinal connecting member assembly having an elongate flexible rod-like inner core 188 and at least one and up to a plurality of cannulated outer spacers or sleeves 190 slidably received on the core 188 and placable between implanted bone screws 4 as illustrated, for example, in FIG. 49. The longitudinal connecting member 8 is elongate, with the inner core 188 being an elastic substantially solid, smooth and uniform cylinder or rod having an outer cylindrical surface 192 and a substantially circular cross-section. However, it is foreseen that the core may be of a variety of different cross-sections, including but not limited to oval, rectangular or other curved or polygonal configurations. The illustrated core 188 is made from natural or synthetic elastomers, including, but not limited to polyisoprene (natural rubber), and synthetic polymers, copolymers, and thermoplastic elastomers, for example, polyurethane elastomers. The illustrated sleeve 190 is also made from a plastic, such as a thermoplastic elastomer, for example, polycarbonate-urethane having a greater stiffness than the elastomer of the core 188. In order to have low or no wear debris, the sleeve 190 inner surfaces and/or cooperating core 188 outer surfaces may be coated with an ultra thin, ultra hard, ultra slick and ultra smooth coating, such as may be obtained from ion bonding techniques and/or other gas or chemical treatments.

The illustrated core 188 is sized and shaped to be received in the U-shaped channel 174 of the bone screw receiver 172 with the sleeves 190 sized and shaped to extend between bone screws 4, providing limitation and protection of movement of the core 188 at such location. Thus, the sleeve 190 is sized and shaped for substantially even and precise alignment and substantial frictional contact between flat end surfaces 194 and 195 of the sleeve 190 and cooperating flat side surfaces 175 and 175*a* of bone screws 4.

Furthermore, when the longitudinal connecting member 8 is implanted with the sleeves 190 disposed between bone screws 4, and the closure structures 9 are tightened in place in the receivers 172, the implantation tool assembly 1 may be manipulated to direct the pair of adjacent receivers 172 toward one another so as to axially compress the elastic sleeve 190 between facing side surfaces 175 and 175*a* of the adjacent receivers 172. Such compression due to frictional engagement and compression of the sleeve 190 between the bone screws 4 during installation results in some tension and distraction of the core 188 when the implantation tools are removed from the bone screws 4, as the sleeve end surfaces 194 and 195 then press against the facing bone screw surfaces 175 and 175*a*, but the core 188 is otherwise fixed with respect to each of the bone screws 4 within respective receiver channels 174. Such dynamic tension/compression relationship between the sleeve 190 and the elastic core 188 provides further strength and stability to the overall assembly and also allows for the entire connecting member assembly 8 to elongate, if needed, in response to spinal movement. The increased stability and strength of the assembly advantageously allows for use of a smaller, more compact, reduced volume, lower profile longitudinal connecting member 8 and cooperating bone anchors than, for example, flexible cord and spacer type longitudinal connecting member assemblies.

The sleeve 190 further includes a pair of substantially flat parallel and opposite lateral surfaces 196 and 197 and a pair of curved opposite posterior/anterior surfaces 198 and 199. Each of the surfaces 196, 197, 198 and 199 extend between the flat end surfaces 194 and 195. The geometry of the sleeve 190 allows for a narrower width between the parallel surfaces 196 and 197 than a distance or diameter between the curved surfaces 198 and 199. Such geometry provides adequate stiffness or support for the flexible core 188 in flexing due to the distance between the posterior/anterior curved surfaces 198 and 199, while the more narrow width or distance between the flat surfaces 196 and 197 allows for placement of the sleeve 190 between adjacent vertebrae without engagement with such vertebrae. Stated in another way, a cylindrical sleeve having a diameter large enough to produce a desired limit of bending or flexing movement of the core 188 would most likely have a diameter large enough to result in interference of the sleeve cylindrical surface with portions of adjacent vertebrae. The flat surfaces 196 and 197 allow for adequate clearance but do not detract from an overall strength of the sleeve 190.

Extending along the substantially central axis of the sleeve 190 is an internal substantially cylindrical and smooth surface that defines a bore 200 with a circular cross section, the bore 200 extending through the sleeve 190 and sized and shaped to receive the core 188. The internal surface defining the bore 200 is of a slightly greater diameter than an outer diameter of the cylindrical surface 192 of the core 188, allowing for axially directed sliding movement of the sleeve 190 with respect to the core 188 during installation of the core 188 into the sleeve 190 and also when both the core 188 and the sleeve 190 are implanted with the sleeve 190 located between adjacent bone screws 4.

In the illustrated embodiment, the sleeve 190 further includes a compression groove 201. Sleeves 190 according to the invention may include one, none or any desired number of grooves 201. The groove 201 extends substantially uniformly about the sleeve 190, being formed in the external surfaces 196, 197, 198 and 199 of the sleeve 190. The groove or grooves 201 may be added as desired to advantageously increase a longitudinal compressibility of the sleeve 190 during installation between a pair of bone screws 4.

It is foreseen that the core 188 may be sized and made from such materials as to provide for a relatively more rigid longitudinal connecting member 8 or a relatively more flexible member 8 with respect to flex or bendability along the member 8. Also, since the distance between the bone screw receivers or heads 172 can vary, the core 188 may be desirably more or less stiff. As stated above, the illustrated longitudinal connecting member 8 is one of a variety of connecting members, including, but not limited to, rigid rods, rod/coil combinations and chord and spacer combinations, that may cooperate with tools according to the invention.

Figure 29:
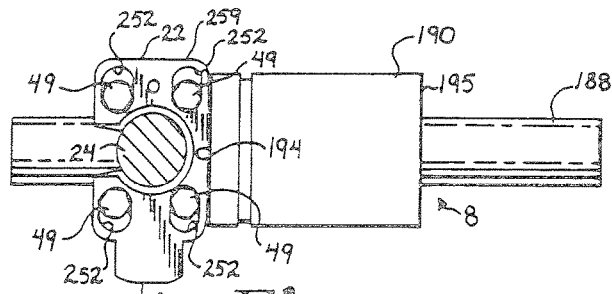
FIG. 29 is a cross-sectional view taken along the line 29-29 of FIG. 26.

With reference to FIGS. 26 and 29-34, the independent stabilizer 22 according to the invention is similar to the stabilizer 20, including a central bore 250, four uniformly sized small bores 252 for receiving lock pins 49, an upper portion 254, a lower portion 256, an assembly pin 258, a first side 259, a spring retainer 260, a second side 261, a top 262 and a bottom 264 for seating on the elongate members 10 and 12, such features being substantially similar in shape and function to the respective central bore 150, four uniformly sized small bores 152, upper portion 154, lower portion 156, assembly pin 158, first side 159, spring retainer 160, second side 162, top 162 and bottom 164 of the driver stabilizer 20. Furthermore, the central bore 250 communicates with a lateral channel 270 that opens to a discontinuous face 272 of the stabilizer 22, the channel 270 being defined by substantially parallel spaced walls 274 and 275. As will be described in greater detail below, the walls 274 and 275 are spaced a distance to provide clearance for receiving selected upper and lower portions of the shaft of the closure starter/reduction tool 24 therebetween. Also, a substantially cylindrical surface 278 that defines the central bore 250 includes a discontinuous guide and advancement structure 280 designed for rotational mating engagement with a cooperating guide and advancement structure 282 of the closure starter/reduction tool 24. The guide and advancement structures 280 and 282 may be a v-thread as illustrated in the drawing figures or other guide and advancement structures known in the art. As compared to the through bores 152 formed in the stabilizer 20 that are circular and function to closely set or lock the members 10 and 12 in a particular spaced relation to one another during rotation of the bone screw driver 18, in the illustrated stabilizer 22, the four through bores 252 that are sized and shaped to receive lock pins 49 therethrough are oval, each being wider in a direction running between the sides 259 and 261, allowing some movement of the members 10 and 12 toward and away from one another when the stabilizer 22 is mounted on the guide tool assembly 1 as illustrated in FIG. 29 with the bottom surface 264 in contact with upper surfaces 56 and 56a of the members 10 and 12, respectively, and thus providing for some additional width of the through channel 101 formed between the members 10 and 12 to allow some play and additional clearance when manipulating the members 10 and 12 and inserting tools and implants utilizing the tool assembly 1.

Figure 30:
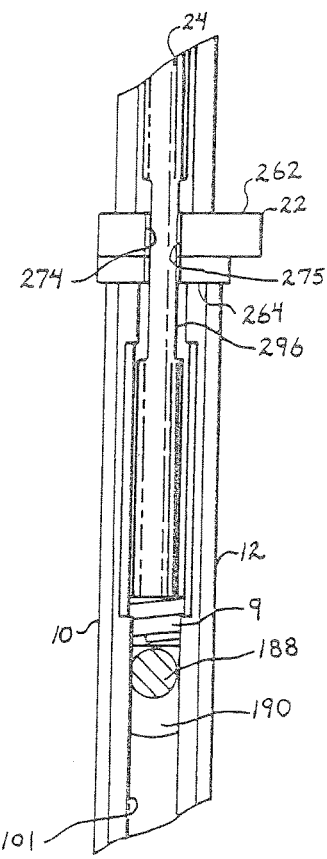
FIG. 30 is an enlarged and partial side elevational view of the assembly of FIG. 26 shown using the closure top starter/reduction tool to reduce the longitudinal connecting member and the closure top toward the polyaxial bone screw.
Figure 31:
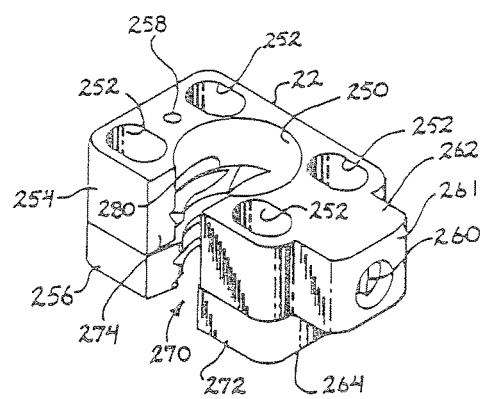
FIG. 31 is an enlarged perspective view of the guide stabilizer of FIG. 26.
Figure 32:
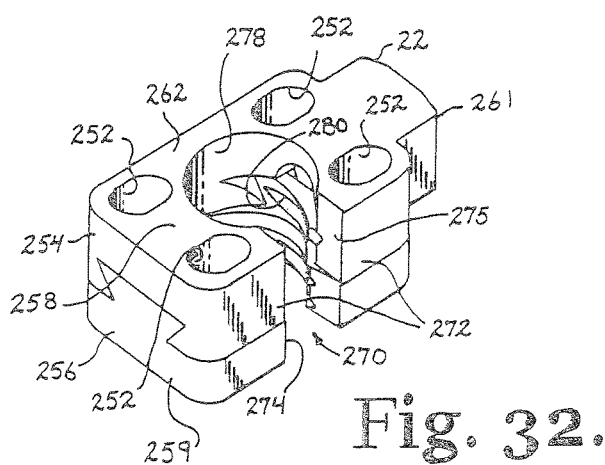
FIG. 32 is a second enlarged perspective view of the guide stabilizer of FIG. 26.
Figure 39:
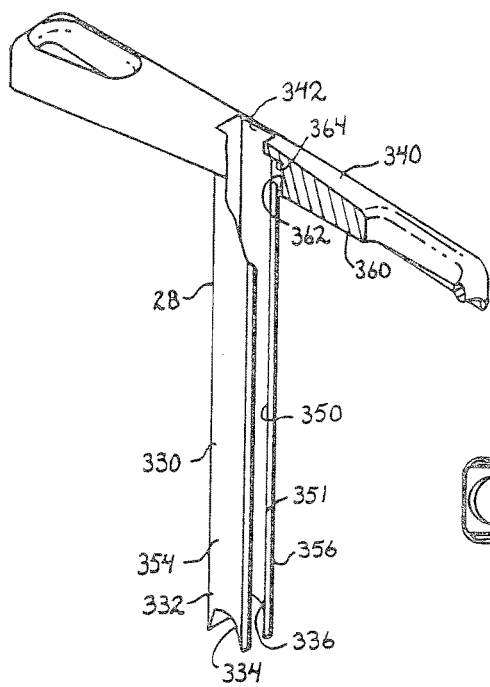
FIG. 39 is a perspective view of a counter-torque tool of the invention with a portion broken away to show the detail thereof.
Figure 40:
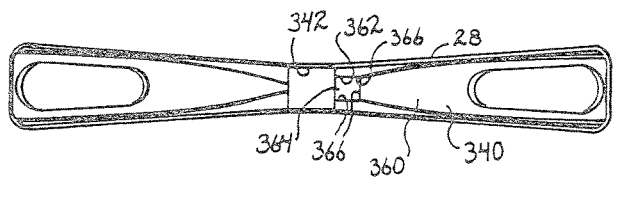
FIG. 40 is a bottom plan view of the counter-torque tool of FIG. 39.

With reference to FIGS. 25, 26, 29, 30, 33, 34, 37 and 38, the closure starter/reduction tool 24 of the tool set 2 of the invention is elongate, having an axis of rotation C and including a handle 290 fixed to an elongate cylindrical stem or shaft 292 and a driving tip 294 fixed to or integral with the shaft 292. The handle 290, shaft 292 and tip 294 are coaxial along the axis of rotation C. The handle 290 includes grooves or shallow apertures to aid a surgeon in gripping and rotating the starter 24 about the axis C when, for example, the starter/reduction tool 24 is engaged with the guide and advancement structure 280 of the stabilizer 22. The closure starter/reduction tool 24 is sized and shaped to be used in cooperation with the tool assembly 1, with the tip 294 in engagement with the closure top 9 and the starter 24 extending through the tool assembly 1 with the handle 290 initially located laterally of the assembly 1 as illustrated in FIG. 25 and thereafter located above the lock pins 49 to allow for adequate clearance between the handle 290 and the assembly 1 to allow for the rotation of the closure top 9 into the bone screw receiver 172 by turning the handle 290. For insertion and removal of the closure starter/reduction tool 24 into and out of the assembly 1, the shaft 292 is reduced in width at two locations; a lower width reduction portion or length 296 and an upper width reduction portion or length 298. The lower width reduction portion 296 is located between the driving tip 294 and the guide and advancement or threaded portion 282. The upper width reduction portion is located between the threaded portion 282 and the handle 290. With particular reference to FIGS. 25 and 30, both the lower portion 296 and the upper portion 298 have a width running perpendicular to the axis C that is less than a distance between the walls 274 and 275 of the stabilizer 22 that define the lateral channel 270 while a remainder of the shaft 292 has a diameter that is larger than the width of the channel 270. The illustrated reduced portions 296 and 298 are formed by cutouts or recesses that result in a pair of parallel walls formed in the otherwise cylindrical shaft 292. It is foreseen that the reduced portions 296 and 298 may also be made by reducing the diameter of the shaft 292 in the desired locations. The reduced portion 296 allows for insertion of the closure starter/reduction tool 24 into the stabilizer 22 and between the members 10 and 12 during a process of inserting the closure top 9 between the members 10 and 12 between the cut-out surfaces 58 and 58a as shown in FIGS. 25, 26 and 30. The reduced portion 298 allows for removal of the tool 24 from the members 10 and 12 after reduction of the longitudinal connecting member 8 and mating of the closure top 9 to the receiver of the bone screw 4 as evident from FIGS. 33 and 34. During a process of reduction of the longitudinal connecting member 8 down the assembly 1, the remainder of the shaft 292 is of a diameter large enough to keep the tool 24 between the members 10 and 12 as desired for reduction of the longitudinal connecting member 8 into the receiver 172 and attachment of the closure top 9 to the bone screw 4.

The driving tip 294 includes a slot 300 and faceted geometry 301 for capturing and holding the closure structure 9 driving feature 184 prior to and during insertion of the structure 9 into the receiver 172. In some embodiments, the tip 294 may further include a lateral projection or key (not shown) sized and shaped to mate with a key slot of the closure structure drive 184 for precise positioning of the closure structure 9 into the insertion tool 1 and the receiver 172 by the closure starter/reduction tool 24. Specifically, as the outer thread 282 formed on the closure starter/reduction tool 24 is sized and shaped to rotatably mate with the guide and advancement structure 280 of the stabilizer 22, a position of a leading surface of the thread 282 and the leading surface of the guide and advancement structure 280 may be synchronized along with the positioning of a key of the driving tip 294 so that a controlled, exact mating of the closure top 9 with the receiver 172 may be consistently accomplished. As will be described in greater detail below, according to the invention, the thread 282 of the tool 24 is of sufficient length that the longitudinal connecting member 8 (or other type of connecting member, such as a coil or rod) is moved downwardly in a controlled manner into the receiver 172 by rotating the tool 24.

Figure 41:
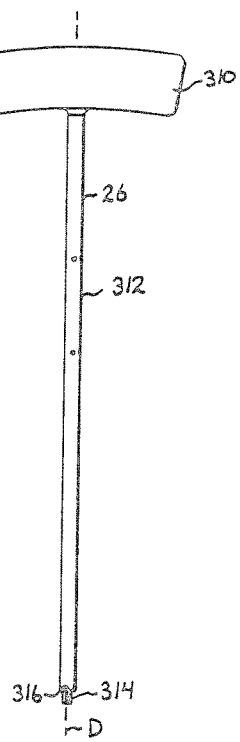
FIG. 41 is a reduced side elevational view of a closure top driver.
Figure 42:
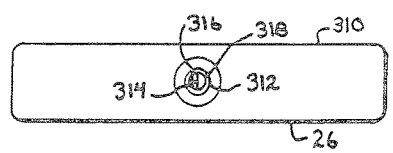
FIG. 42 is an enlarged bottom plan view of the closure top driver of FIG. 41.
Figure 43:
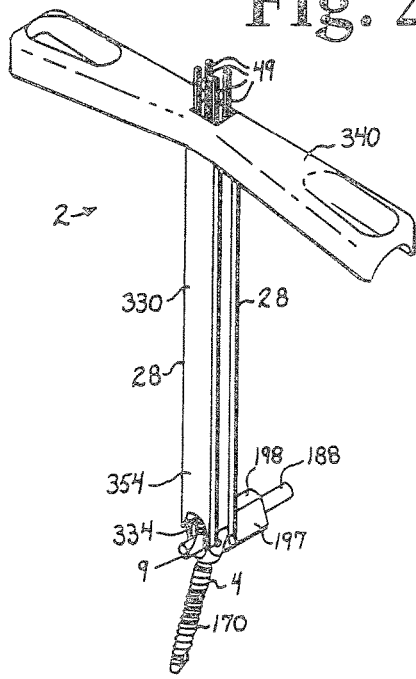
FIG. 43 is a reduced perspective view of the assembly of FIG. 34 with the closure top starter removed and further shown received in the counter-torque tool of FIG. 39.
Figure 47:
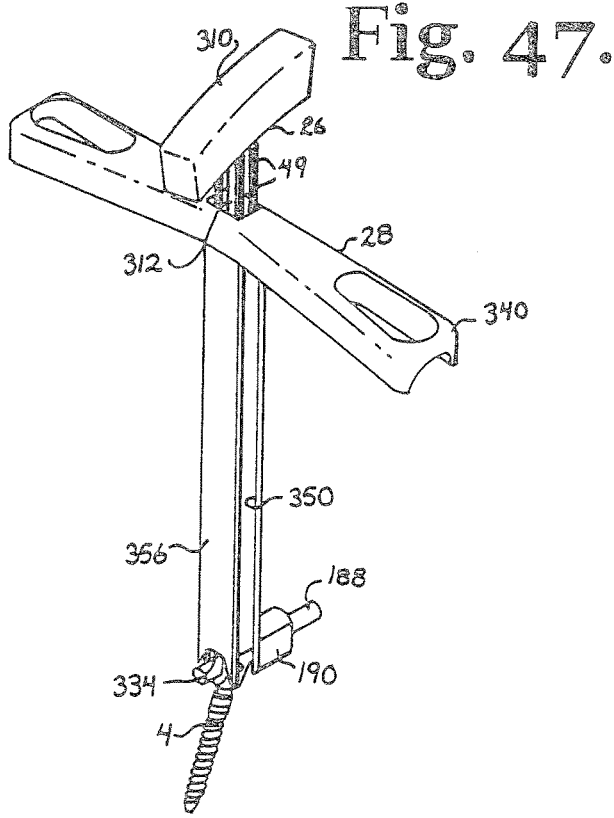
FIG. 47 is a reduced perspective view similar to FIG. 45 and further showing the closure top driver of FIG. 41 inserted into the counter-torque tool for tightening of the closure top.

The illustrated closure driver 26 according to the invention is sized and shaped to cooperate with the assembly 1 and the illustrated counter torque tool 28. As will be described in greater detail below, the closure driver 26 is inserted into the assembly 1 and engages the closure top 9 for tightening the same after removal of the closure starter/reduction tool 24 from the assembly 1. With particular reference to FIGS. 41, 42 and 47, the driver 26 includes a somewhat curved, T-shaped handle 310 fixed to an elongate cylindrical stem or shaft 312 and a driving tip 314 fixed to or integral with the shaft 312. The handle 310, shaft 312 and tip 324 are coaxial along an axis of rotation D. The handle 310 is sized and shaped to aid a surgeon in gripping and rotating the driver 26 about the axis D during tightening of the closure top 9 in the bone screw 4. The shaft 312 is of a desired length so that the tool 26 may be used in cooperation with the tool assembly 1, with the tip 314 in engagement with the closure top 9 and the shaft 312 extending through the tool assembly 1 with the handle 310 located above the lock pins 49 and the counter torque tool 28 with adequate clearance between the handle 310 and the assembly 1 to allow for the rotation of the closure top 9 in the bone screw receiver 172 by rotation of the handle 310 about the axis D. The driving tip 314 includes a slot 316 and faceted geometry 318 for engaging the closure structure 9 driving feature 184 during tightening of the structure 9 into the receiver 172.

Figure 45:
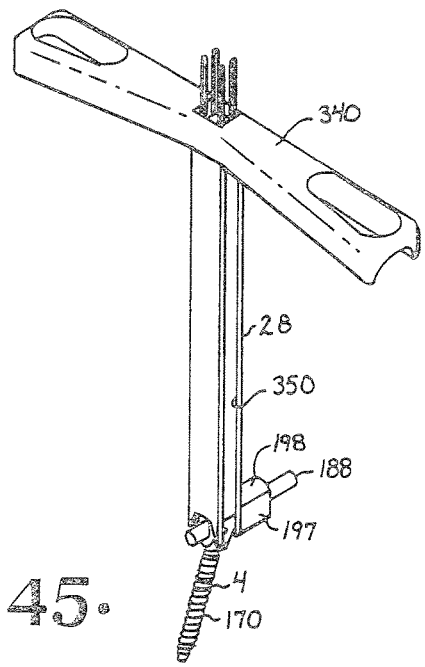
FIG. 45 is a reduced perspective view similar to FIG. 44, showing the counter-torque tool engaging and aligning the sleeve of the longitudinal connecting member.
Figure 44:
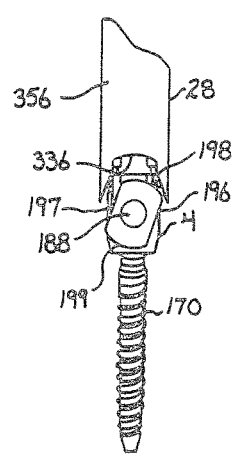
FIG. 44 is an enlarged and partial side elevational view of the assembly and counter-torque tool combination of FIG. 43.
Figure 46:
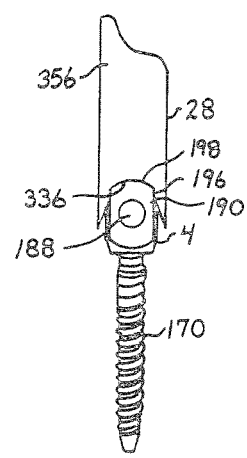
FIG. 46 is an enlarged and partial side elevational view of the assembly and counter-torque alignment of FIG. 45.

With particular reference to FIGS. 39, 40 and 43-47, the illustrated counter torque tool 28 includes a hollow shaft 330 that is sized and shaped to be slidably received over the tool assembly 1. The shaft 330 has a lower end portion 332 that has a pair of diametrically spaced, curved bridges 334 and 336. With particular reference to FIGS. 44 and 46, each of the bridges 334 and 336 is sized and shaped to closely fit over the curved surface 198 and portions of the opposed flat surfaces 196 and 197 of the sleeve 190 and thus align the sleeve 190 of the longitudinal connecting member 8 with respect to the bone screw 4 in a desired orientation with the sides 196 and 197 parallel to the outer surfaces of the arms 30 and 32 of the bone screw 4. When seated squarely on at least one sleeve 190, as illustrated in FIGS. 46 and 47, the counter torque tool 28 allows a surgeon to counter a torque applied by the driver 26 during rotation and tightening of the closure top 9 in the receiver 172. The counter torque tool 28 also has an upper handle 340 disposed substantially perpendicular to the shaft 330 and having an upper opening 342 communicating with the hollow shaft through which the holding assembly 1 and the driver 26 passes in the manner suggested by FIGS. 43-47. The illustrated counter torque tool 28 further includes a lateral opening or side channel 350 formed in a surface 351, the channel 350 communicating with the hollow interior of the shaft 330 along an entire length of the shaft 330. The opening or channel 350 is disposed between substantially parallel walls 354 and 356 that define respective alignment bridges 334 and 336. The channel 350 is sized to receive the upper portion 254 of the stabilizer 22 that forms a ledge or overhang of the lower portion 256 at the side 261. Furthermore, the handle 340 includes a lower surface 360. Formed in the lower surface 360 is a recess 362 sized and shaped to receive the upper portion 254 of the stabilizer 22. The shaft 330 and the handle 340 are sized and shaped such that when the bridges 334 and/or 336 properly seat upon and align with one or two longitudinal connecting member sleeves 190 as illustrated in FIGS. 45 and 46, the top 262 of the stabilizer 22 makes contact with a substantially flat surface 362 that partially defines the recess 362. Lateral walls 366 that also define the recess 363 surround the stabilizer upper portion 254 near the side 261, limiting side to side and front to back movement of the stabilizer 22 and thus of the entire holding tool assembly 1 with respect to the counter torque tool 28.

In use, the previously described tools are utilized to attach one or more longitudinal connecting members 8 to the human spinal column 6. The procedure is begun by selection of a bone screw 4 in accordance with the size of the patient's vertebra 16 and the requirements of the spinal support needed. Bone screws 4 having a rotatable or polyaxial heads or receivers 172 are preferred but not required for the procedure, as such allow relatively easy adjustment of the longitudinal connecting member 8 in the tool assembly 1 and with respect to other tools included in the tool set 2 during placement and for movement of the tool assembly 1 or individual members 10 and 12, as described below. The bone screw 4 is also preferably cannulated so as to be receivable over and guided by a guide pin or wire as discussed more fully below.

Alternative polyaxial, hinged and monoaxial bone screws, for example, such as those described in U.S. patent application Ser. No. 11/328,481 filed Jan. 9, 2006, the disclosure of which is incorporated by reference herein, may also be used with tools according to the present invention. Furthermore, other types of longitudinal connecting members may be used according to the invention including, for example, chord/spacer combinations, rods and coils.

With particular reference to FIGS. 1-11, the tool assembly 1 may be placed into engagement with the polyaxial bone screw 4 as follows: With particular reference to FIG. 1, a pair of lock pins 49 are inserted in the elongate member 10 cylindrical channels 47 and 48 with each lock pin tip or bottom 95 being inserted into the channels at the top surface 56 and guided downwardly toward the bottom 64 of the tool 10. Once the threaded portion 97 makes contact with the threaded inner wall 60, the particular lock pin 49 is rotated and driven downwardly slightly, enough to place the lock pin 49 into engagement with the member 10. The bone screw receiver 172 is then aligned with an elongate tool member 10 by aligning the laser etched stripe 92 of the receiver arm 30 with the laser etched stripe 90 of the tool member 10. The lip surface 74 is then placed next to the bone screw arm 30 slightly beneath the groove 76 and then moved up into the groove as shown in FIGS. 8 and 9. The lock pin bottoms 95 are moved toward the receiver arm top surface 31 by mounting a lock pin driver socket (not shown) on a lock pin 49 with the driving portion 96 of the pin 49 received in an elongate socket of the driver. The lock pin driver is rotated about a center axis thereof until the bottom surface 95 of the pin 49 frictionally engages with the receiver surface 31 and the lip surface 74 is fully engaged with the bone screw arm 30 at the groove 76. The raised strip 78 disposed in the slit 80 of the receiver advantageously prohibits movement of the pin 49 between the surfaces 175 and 175a, but some movement toward and away from the channel 174 is possible. The lock pins 49 are inserted into the channels 47a and 48a of the member 12 in a similar fashion to what has been described herein with respect to the lock pins and channels 47 and 48 of the member 10. The member 12 is then engaged with the bone screw arm 32 at the groove 76a, with the lock pins 49 driven downward into engagement with the top surface 33 and the arm 32. It is noted that in certain embodiments according to the invention that do not include offset slits 80 and 86 in the bone screw arms 30 and 32, respectively, or cooperating offset alignment strips, such as the strip 78, the members 10 and 12 may be attached to either of the bone screw arms 30 or 32 as previously described herein. With reference to FIG. 11, both the members 10 and 12 are thus attached to the bone screw 4, forming the guide tool assembly 1 that provides some freedom of movement of the members 10 and 12 toward and away from the receiver channel 174 allowing for ease in insertion of longitudinal connecting members, tools and any other bone attachment structures.

With reference to FIGS. 12-22, after installation of the members 10 and 12 on the bone screw receiver 172, the driver 18 is inserted into the tool assembly 1 by downward or lateral insertion of the driving end portion 134 and a portion of the shaft 132 into the channel 101 formed between the members 10 and 12 with the stabilizer 20 initially disposed above the lock pins 49 as shown in FIG. 20. Thereafter, the driver 18 is moved downwardly toward the receiver 172 until the driving head 140 engages the drive feature 144 of the bone screw 4. The stabilizer 20 is then moved downwardly toward the members 10 and 12 with each of the lock pins 49 being received in a through bore 152 of the stabilizer 20. The stabilizer is moved toward the members 10 and 12 until the bottom surface 164 seats on top surfaces 56 and 56a of respective elongate members 10 and 12 and also upon the surface 167 of the lock limit 136. With reference to FIG. 22, the driver 18 is manually rotated about the axis A thereof to rotate and drive the bone screw shank 170 into the vertebra 16. The driver 18 may be removed by simply sliding the shaft 132 upwardly away from the receiver 172 until the stabilizer 20 clears the pins 49 and the driving end 140 is out of the incision, and then the driver 18 may be moved laterally out of the tool assembly 1 in either direction out of the through channel 101.

With further reference to FIG. 22, in a method according to the invention, a relatively minimally invasive incision or incisions 368 may be made in a patient's skin 369 and stretched so as to snugly receive the guide tool assembly 1 and other tools of the invention. A drill (not shown) is utilized to form a first guide bore in the vertebra 16 under guidance of non invasive imaging techniques, which procedure is well known and established. A thin pin or guide wire may then be inserted in the first guide bore, the pin and guide bore functioning to minimize stress on the vertebra 16 and providing an eventual guide for the placement and angle of the bone screw shank 170 with respect to the vertebra 16. Then the guide bore is enlarged utilizing a cannulated drilling tool or tap having an integral or otherwise attached cannulated and threaded bit with an outer surface sized and shaped to correspond to the size and shape of the chosen threaded bone screw 1.

With the pin fixed to the vertebra 16 and in place in an enlarged guide bore and extending upwardly through the bore and out of the incision 368, the pin is threaded into the bore 178 at the tip 179 of the shank 170 and out of the opening at the top surface 176 of the bone screw shank 170. The pin is then threaded through the driver 18. With the driver 18 installed in the tool assembly 1 as illustrated in FIG. 22 and as previously described herein, the bone screw 4 is then rotated and driven into the tapped bore in the vertebra 16. Depending upon the type of bone screw 4 utilized in connection with the tool assembly of the invention, the surgeon may drive the bone screw shank 170 independently of the receiver 172 and attached tool 1, or the surgeon may drive the bone screw shank 170 and the receiver 172 and attached tool 1 until the shank body 170 is disposed at a desired depth in the tapped bore of the respective vertebra 16. At least two and up to a plurality of bone screws 4 with attached insertion tool assemblies 1 are installed in each vertebra 16 to be attached to the longitudinal connecting member 8.

With reference to FIGS. 23-38, the closure starter/reduction tool 24 is then used to insert the closure top 9 between the members 10 and 12 and press or reduce the longitudinal connecting member 8 or other type of longitudinal connecting member, such as a rod or coil, downwardly into the receivers 172 of the implanted bone screws 4. With reference to FIG. 23, in the embodiment shown, a spacer or sleeve 190 is cut to length for engagement with each of two adjacent bone screws 4 and pre-loaded onto the inner core 188 then the core 188 of the longitudinal connecting member 8 is inserted into and through the channel 101 at the recessed portions 58 and 58a formed by the members 10 and 12 with a tail or end of the cord core 188 extending out of the channel 101. The core 188 is then manipulated downwardly manually to a location below the recessed portions 58 and 58a where the channel 101 narrows, thus generally aligning the core 188 with the bone screw channel with the sleeve 190 being in sliding contact with outer planar surfaces of the members 10 and 12 as illustrated in FIGS. 25, 26 and 29. A closure top 9 is placed upon and frictionally engaged with the closure starter/reduction tool 24 by inserting the driving tip 294 into the closure driving feature 184. Then, the closure top 9 may be laterally inserted between the members 10 and 12 through the channel 101 at the recessed portions 58 and 58a as illustrated in FIG. 25. To stabilize the members 10 and 12, the stabilizer 22 may then be engaged with the members 10 and 12 by downward insertion of the stabilizer 22 over the lock pins 49 as shown in FIGS. 26, 29 and 30, with each lock pin 49 being received in a bore 252 of the stabilizer 22. The stabilizer 22 is moved toward the members 10 and 12 until the bottom surface 264 seats on top surfaces 56 and 56a of respective elongate members 10 and 12. With further reference to FIGS. 26 and 30, thereafter, the closure starter/reduction tool 24 may be laterally angularly inserted into the channel 101, angled upwardly into a position parallel and centrally located between the members 10 and 12, with the reduced portion 296 of the tool 24 being receivable in and through the channel 270 of the stabilizer 22 as best illustrated in FIG. 30.

The tool 24 is then manually pushed downwardly along the channel 101 between the members 10 and 12 with the closure top 9 bottom surface 185 engaging and pressing the inner core 188 downwardly toward the bone screw 4 until the threaded portion 282 of the tool 24 makes contact with the guide and advancement structure 280 of the stabilizer 22. At the same time, the sleeve 190 is manually pressed downwardly through the incision 368 or along an extension thereof. Back muscle tissue separates to allow the insertion of the core and sleeve combination of the connecting member 8 and can be further separated by finger separation or cutting through of one or more incisions, if required.

With particular reference to FIG. 33, the closure starter/reduction tool 24 is then rotated about the axis C by rotating the handle 290, mating the threads 280 and 282, providing mechanical advantage to move the closure top 9 and core 188 toward the receiver 172 in a controlled manner. During such rotation, the closure structure bottom surface makes contact with the core 188, moving and also holding the core 188 in a controlled manner at intermediate positions along the assembly 1, allowing for manipulation of the sleeve 190 in a downward direction without the need for manual pressure on the starter/reduction tool 24 as both the core 188 and the sleeve 190 are reduced downwardly toward the bone screw 4 and also as other portions of the core 188 and other sleeves 190 are being moved downwardly toward other cooperating bone screws 4 also utilizing the tool assembly 1 and other cooperating tools of the invention disclosed herein. Subsequent rotation of the tool 24 also rotates the closure top 9 into engagement with the guide and advancement structure located on inner surfaces of the bone screw arms 30 and 32, capturing the core 188 in the receiver 172 as illustrated in FIG. 34.

It is foreseen that in certain embodiments according to the invention, starting locations of the respective mating guide and advancement structures 280 and 282, as well as a projection or key on the driving tip 294 and a key slot on the closure top drive 184 may be positioned to precisely mate the closure structure guide and advancement structure 182 with a guide and advancement structure formed on inner surfaces of the arms 30 and 32 of the receiver 172. Also, such an embodiment may include cooperating guide and advancement structures sized and positioned such that once the closure top 9 is threaded fully into the receiver 172, but not otherwise tightened therein, further rotation of the tool 24 may be prohibited by abutment with a thread run out stop.

With reference to FIG. 34, the driving tip 294 of the closure starter/reduction tool 24 is then retracted by simply pulling the tool 24 upwardly away from the receiver 172. Then, the tool 24 may be removed from the assembly 1 by lifting the tool 24 upwardly between the members 10 and 12 or by lateral and angular movement, with the reduced portion 298 passing through the lateral channel 270 and the larger threaded portion 282 passing through the larger recess created by the cooperating recessed portions 58 and 58a of respective members 10 and 12.

With reference to FIGS. 39-47, once all of the closure tops 9 are in a seated position in respective bone screws 4 and the surgeon is satisfied with the position of all of the elements, the closure tops 9 may be locked into place with the elongate driving tool 26 and the counter torque tool 28. With particular reference to FIGS. 43-46, the counter torque tool 28 is inserted over the assembly 1 and moved downwardly toward the bone screw 4 with the end or side 261 of the stabilizer 22 extending through the side channel 350. With particular reference to FIGS. 44 and 46, as the tool 28 is pressed downwardly against the sleeve 190, contact between the bridge 336 and the spacer surfaces 196, 197 and 198 straightens the sleeve 190, aligning the surfaces 196 and 197 into substantially parallel relationship with outer surfaces of the receiver arms 30 and 32. Also, with reference to FIGS. 39 and 40, as the sleeve 190 becomes straightened, the stabilizer 22 top surface 262 makes contact with the surface 364 of the counter torque tool 28 ensuring alignment between the sleeve 190 and the bone screw receiver 172 without excess pressure being placed on the longitudinal connecting member 8 or the bone screw 4. With reference to FIGS. 41, 42 and 47, the closure driver 26 is then inserted into the upper opening 342 of the counter torque tool 28 and moved downwardly until the driving tip 314 engages the driving feature 184 of the closure top 9. The tool 28 is then rotated to tighten the closure top 9 in the receiver 172 by rotating the T-shaped handle 310 while the counter torque tool 28 is held stationary using the handle 340. By rotating the handle 310, a surgeon applies adequate tightening force, typically 70-120 inch pounds, to fully tighten and set the closure top 9 within the receiver 172 so that the bottom surface point 186 and rim 187 dig into the cylindrical surface 192 of the core 188.

As indicated previously herein, as the closure tops 9 are rotated and then tightened against the core 188 in a pair of cooperating bone screws 4, such bone screws 4 may be pressed toward one another by moving attached assemblies 1 toward one another, thereby frictionally engaging and then compressing the sleeve 190 between the adjacent bone screws 4. When all tooling is removed, the sleeve 190, pressing against facing surfaces of the cooperating bone screw receivers 172, stretches the elastic core 188. The resulting bone attachment assembly is thus substantially dynamically loaded and oriented relative to the cooperating vertebrae to provide relief (e.g., shock absorption) and protected movement with respect to flexion, extension, distraction and compressive forces placed on the longitudinal connecting member 8 and the two connected bone screws 4. The elasticity of the core 188 may also allow the core 188 to twist or turn, providing relief for torsional stresses. The sleeve 190 limits such torsional movement as well as bending movement of the core 188, providing spinal support. Furthermore, because the sleeve 190 is compressed during installation, the sleeve advantageously allows for some protected extension or distraction of both the core 188 and the sleeve 190.

Figure 48:
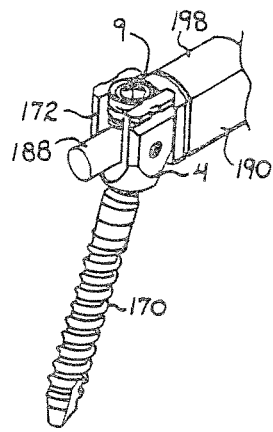
FIG. 48 is an enlarged perspective view similar to FIG. 47, showing the closure top driver and counter-torque tool removed subsequent to tightening of the closure top.

After all of the closure tops 9 have been locked into place, the driver 26 and counter torque tools 28 are removed, followed by removal of each of the tool assemblies 1. The stabilizer 22 is first removed by sliding the stabilizer 22 upwardly and away from the member 10 and 12 and off of the lock pins 49. The lock pin driver (not shown) is then used on each lock pin 49 to loosen each pin 40 from the members 10 and 12 by rotating the driver to rotate each pin upwardly and away from the surface 31 or 33. Slight downward force is then placed on each of the members 10 and 12 by the surgeon to move the lip surfaces 74 and 74a out of the respective grooves 76 and 76a of the receiver 172. Then the members 10 and 12 are moved upwardly away from the receiver 172 and out of the incision 368. Such procedure is followed to remove each tool member 10 and 12 out of the incision or various incisions utilized to implant the bone screws 4 and longitudinal connecting member 8 after which the incision or incisions 368 are closed. Examples of fully assembled and implanted bone screw or screws 4 with a cooperating longitudinal connecting member 8 are illustrated in FIGS. 48 and 49.

If removal of the longitudinal connecting member 8 from any of the bone screws 4 is necessary, or if it is desired to release the member 8 at a particular location, disassembly is then accomplished in reverse order to the procedure described previously herein for assembly.

Figure 52:
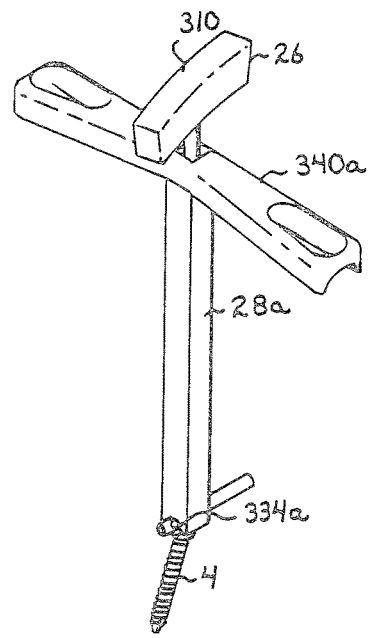
FIG. 52 is a perspective view similar to FIG. 51 further showing a second counter-torque tool and the closure top driver of FIG. 41.
Figure 51:
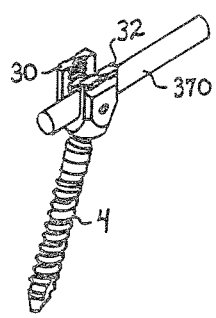
FIG. 51 is an enlarged perspective view similar to FIG. 50 showing the longitudinal connecting member and sleeve removed and replaced by a replacement connecting member.
Figure 53:
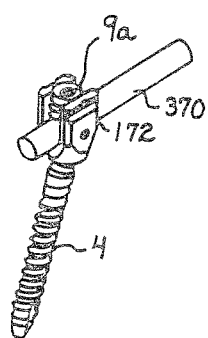
FIG. 53 is a perspective view similar to FIG. 52, showing the counter-torque tool and driver removed and further showing a closure top engaging the replacement connecting member.

With reference to FIGS. 50-53, eventually, if the spine requires more rigid support, the longitudinal connecting member 8 may be removed and replaced with another longitudinal connecting member, such as a solid rigid rod 370, having the same diameter as the inner core 188, utilizing the same or same sized closure tops 9. Such is accomplished by using the driving tool 26 inserted in the aperture 184 to rotate and remove the closure tops 9 from the receivers 172 followed by removal of the connecting member 8. The replacement rod 370 is then implanted, followed by closure top 9a insertion and tightening using the same or similar tools previously described herein. With reference to FIG. 52, it is noted that the illustrated embodiment includes a counter torque tool 28a that includes curved bridges 334a sized and shaped to closely engage the replacement rod 370.

Alternatively, if less support is eventually required, a less rigid, more flexible assembly, for example, including a longitudinal connecting member made with a more flexible core, but otherwise having the same diameter as the inner core 188, may replace the connector 8 also utilizing the same bone screws 4.

It is to be understood that while certain forms of the present invention have been illustrated and described herein, it is not to be limited to the specific forms or arrangement of parts described and shown.

What is claimed and desired to be secured by Letters Patent is as follows:

1. An implant assembly comprising:
   (a) a receiver for a bone anchor and including:
      (1) a pair of laterally spaced upstanding arms forming a rod-receiving channel therebetween;
      (2) each arm having an outwardly facing tool attachment structure thereon, each outwardly facing tool attachment structure including:
         (i) a horizontally extending groove which forms a downwardly facing surface, the groove located near a top of its respective arm of the receiver; and
         (ii) each of the grooves extending along an outer surface of the receiver from a front surface to a back surface of its respective arm of the receiver; and
   (b) a tool for releasably holding the receiver and including:
      (1) a pair of discrete elongated members being spaced apart from each other from a top end thereof to a bottom end thereof to form a through channel therebetween, the through channel extending an entire length of the tool, and each elongated member is free from contact with respect to one another and independently manipulatable with respect to one another;
      (2) each elongated member is independently attachable to each receiver arm and each elongated member having an inward facing receiver attachment structure thereon positioned near a lower portion thereof for vertically slidable mating engagement with each receiver arm tool attachment structure; and wherein
      (3) each elongated member receiver attachment structure completely covers the outwardly facing tool attachment structure on each receiver arm.

2. An implant assembly as set forth in claim 1 wherein the receiver includes:
   (a) a threaded bone screw shank extending from a lower end thereof.

3. An implant assembly as set forth in claim 1 wherein the receiver includes:
   (a) a threaded bone screw shank polyaxially engaged therewith and extending from a lower end thereof.

4. A bone anchor receiver in combination with a tool for inserting a rod comprising:
   a) the receiver having a pair of laterally spaced upwardly extending arms with respective side surfaces on an exterior thereof, the arms forming a rod-receiving channel therebetween;
   b) each arm having an outwardly facing tool attachment structure near a top thereof, the outwardly facing tool attachment structure including:
      1) a horizontally extending groove which forms a downwardly facing surface, the groove located near the top of its respective arm of the receiver; and
      2) each of the grooves extending along an outer surface of the receiver from a front surface to a back surface of its respective arm of the receiver;
   c) the tool having two discrete parts, each part being spaced apart from the other from an upper end thereof to a lower end thereof to form a through channel therebetween, the through channel extending an entire length of the tool, and each part is independently manipulatable with respect to one another and the lower end thereof having a mating tool attachment structure having an inwardly projecting member to detachably mate with the receiver tool attachment structure; and
   d) wherein each tool part is independently and separately attached to each receiver arm by vertical sliding engagement so as to form a side opening tool channel, said tool channel being alignable with the receiver rod-receiving channel, so as to receive a rod therebetween.

5. A receiver for a bone anchor in combination with an elongate tool assembly for releasably holding the receiver near a lower end thereof:
   a) the receiver having a pair of laterally spaced upwardly extending arms with lateral surfaces, each having a tool attachment structure, wherein the tool assembly can be vertically slidably attachable thereto, the tool attachment structure including:
      1) a horizontally extending groove which forms a downwardly facing surface, the groove located near the top of its respective arm of the receiver; and
      2) each of the grooves extending along an outer surface of the receiver from a front surface to a back surface of its respective arm of the receiver;
   b) the tool assembly having a pair of discrete elongated members spaced apart from each other from an upper end thereof to a lower end thereof to form a through channel therebetween, the through channel extending an entire length of the tool and each elongated member being independently manipulatable with respect to one another, each member independently and separately attachable to the receiver, one after the other, each of the members including an inwardly projecting structure for releasably mating with a respective receiver arm tool attachment structure; and c) the receiver having a central axis such that the through channel and the receiver central axis are aligned when connected.

6. A bone anchor receiver in combination with a tool for inserting a rod comprising:
- a) the receiver having a pair of laterally spaced upwardly extending arms forming a rod-receiving channel therebetween;
- b) each arm having a vertically slideably engageable tool attachment structure thereon, the vertically slideably engageable tool attachment structure including:
  1) a horizontally extending groove which forms a downwardly facing surface, the groove located near a top of its respective arm of the receiver; and
  2) each of the grooves extending along an outer surface of the receiver from a front surface to a back surface of its respective arm of the receiver;
- c) the tool having two discrete parts being spaced apart from each other from an upper end thereof to a lower end thereof to form a through channel therebetween, the through channel extending an entire length of the tool, the lower end of each part having a mating tool attachment structure having inwardly facing projections to detachably mate with, and completely cover, the receiver tool attachment structure; and
- d) wherein each tool part is independently manipulatable with respect to one another and separately attached to each receiver arm so as to form a side opening tool channel along a length thereof, said tool channel being alignable with the receiver rod-receiving channel, so as to receive a rod therebetween and guide the rod into the rod receiving channel;
- e) wherein each tool part is individually attachable to one receiver arm, one after the other.

7. The combination of claim 6, wherein each tool has a outward facing planar surface.

\* \* \* \* \*